US008895000B2

(12) United States Patent
Zhou et al.

(10) Patent No.: US 8,895,000 B2
(45) Date of Patent: Nov. 25, 2014

(54) METHODS FOR INHIBITING THE BINDING OF ENDOSIALIN TO LIGANDS

(75) Inventors: Yuhong Zhou, Phoenixville, PA (US); Brian Tomkowicz, Philadelphia, PA (US); Luigi Grasso, Bryn Mawr, PA (US); Nicholas C. Nicolaides, Audubon, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 1115 days.

(21) Appl. No.: 12/873,667

(22) Filed: Sep. 1, 2010

(65) Prior Publication Data
US 2011/0033455 A1  Feb. 10, 2011

Related U.S. Application Data

(62) Division of application No. 12/062,630, filed on Apr. 4, 2008, now Pat. No. 7,807,382.

(60) Provisional application No. 60/910,362, filed on Apr. 5, 2007, provisional application No. 60/980,026, filed on Oct. 15, 2007.

(51) Int. Cl.
*A61K 39/00* (2006.01)
*A61K 39/395* (2006.01)
*C07K 16/28* (2006.01)

(52) U.S. Cl.
CPC .......... *C07K 16/2851* (2013.01); *C07K 2319/30* (2013.01); *C07K 2316/96* (2013.01); *C07K 2317/24* (2013.01); *C07K 2317/56* (2013.01); *A61K 2039/505* (2013.01)
USPC ................... 424/133.1; 424/172.1; 424/141.1; 424/143.1

(58) Field of Classification Search
None
See application file for complete search history.

(56) References Cited

U.S. PATENT DOCUMENTS

| | | | |
|---|---|---|---|
| 5,342,757 A | 8/1994 | Garin-Chesa et al. | |
| 5,437,865 A | 8/1995 | Garin-Chesa et al. | |
| 5,693,763 A | 12/1997 | Codington et al. | |
| 5,789,650 A | 8/1998 | Lonberg et al. | |
| 5,798,230 A | 8/1998 | Bornkamm et al. | |
| 5,811,522 A | 9/1998 | Wallace et al. | |
| 6,090,930 A | 7/2000 | Wallace et al. | |
| 6,146,894 A | 11/2000 | Nicolaides et al. | |
| 6,217,868 B1 | 4/2001 | Wallace et al. | |
| 6,261,535 B1 | 7/2001 | Thorpe et al. | |
| 6,391,302 B1* | 5/2002 | Wallace et al. | 424/181.1 |
| 7,358,351 B2 | 4/2008 | St. Croix | |
| 7,615,372 B2 | 11/2009 | Nicolaides et al. | |
| 7,807,382 B2 | 10/2010 | Zhou et al. | |
| 8,524,237 B2* | 9/2013 | Nicolaides et al. | 424/156.1 |
| 2003/0124579 A1 | 7/2003 | Mack et al. | |
| 2004/0014058 A1 | 1/2004 | Alsobrook et al. | |
| 2004/0043928 A1 | 3/2004 | Kekuda et al. | |
| 2004/0048254 A1 | 3/2004 | Olek et al. | |
| 2004/0253606 A1 | 12/2004 | Aziz et al. | |
| 2005/0142138 A1 | 6/2005 | St. Croix | |
| 2006/0121541 A1 | 6/2006 | Grasso et al. | |
| 2006/0127902 A1 | 6/2006 | Madden et al. | |
| 2006/0239911 A1 | 10/2006 | Nicolaides et al. | |
| 2007/0020271 A1 | 1/2007 | Teicher et al. | |
| 2007/0141066 A1 | 6/2007 | Phillips et al. | |
| 2007/0161022 A1 | 7/2007 | Kim et al. | |
| 2007/0292354 A1 | 12/2007 | Port | |
| 2008/0248034 A1 | 10/2008 | Zhou | |
| 2008/0300170 A1 | 12/2008 | Gelber et al. | |
| 2009/0017030 A1 | 1/2009 | St. Croix et al. | |
| 2009/0175844 A1 | 7/2009 | Nakamura et al. | |
| 2009/0176656 A1 | 7/2009 | Halloran | |
| 2009/0203534 A1 | 8/2009 | Hossain et al. | |
| 2009/0239223 A1 | 9/2009 | Gehrmann et al. | |
| 2010/0021454 A1 | 1/2010 | Nicolaides et al. | |
| 2010/0062002 A1 | 3/2010 | Madden et al. | |
| 2010/0092470 A1 | 4/2010 | Bhatt et al. | |
| 2010/0092476 A1 | 4/2010 | Hanash et al. | |
| 2010/0136584 A1 | 6/2010 | Bhatt et al. | |
| 2010/0196426 A1 | 8/2010 | Skog et al. | |
| 2010/0260769 A1 | 10/2010 | Sass et al. | |

FOREIGN PATENT DOCUMENTS

| | | |
|---|---|---|
| EP | 0 239 400 B1 | 8/1994 |
| WO | WO 90/07861 A1 | 7/1990 |
| WO | WO 94/11023 A1 | 5/1994 |
| WO | WO 95/24483 | 9/1995 |
| WO | WO 00/13575 | 3/2000 |
| WO | WO 02/10217 A2 | 2/2002 |
| WO | WO 02/054856 A1 | 7/2002 |
| WO | WO2004/078942 * | 9/2004 |

(Continued)

OTHER PUBLICATIONS

Becker et al. Tumor stroma marker endosialin (Tem1) is a binding partner of metastasis-related protein Mac-2 BP/90K. FASEB Journal. 2008;22:3059-3067.*
Nanda et al. Tumor endothelial marker 1 (Tem1) functions in the growth and progression of abdominal tumors. Proc Natl Acad Sci U S A. Feb. 28, 2006;103(9):3351-6.*
"FY2009 Product Creation Meeting, Dramatic Leap Plan 2011", Eisai Co., Ltd., Power Point Presentation, Dec. 18, 2009, 121 pages.
Asahara et al., "Endothelial progenitor cells for postnatal vasculogenesis", Am. J. Physiol. Cell Physiol., Sep. 2004, 287, C572-C579.
Bagley et al., "Endosialin/TEM 1/CD248 is a pericyte marker of embryonic and tumor neovascularization", Microvascular Research, Nov. 2008, 76(3), 180-188.
Bagley et al., "Human endothelial precursor cells express tumor endothelial marker 1/endothesialin/CD248", Mol Cancer Ther., Aug. 2008, 7(8) 2536-2546.
Bagley et al., "Human mesenchymal stem cells from bone marrow express tumor endothelial and stromal markers", International Journal of Oncology, Mar. 2009, 34(3), 619-627.

(Continued)

*Primary Examiner* — Maher Haddad
(74) *Attorney, Agent, or Firm* — Baker & Hostetler LLP

(57) ABSTRACT

The invention provides methods for inhibiting the interaction of endosialin with endosialin ligands. The inhibition is effectuated on the genetic level, by inhibiting endosialin gene expression, and on the protein level, by blocking the interaction of cell-surface expressed endosialin with ligands such as fibronectin and collagen. The invention provides methods for identifying inhibitors of the interaction of endosialin with endosialin ligands. Also provided are methods for inhibiting angiogenesis and neovascularization in vivo and in vitro.

28 Claims, 17 Drawing Sheets

(56) References Cited

FOREIGN PATENT DOCUMENTS

| WO | WO 2004/078942 A2 | 9/2004 |
|---|---|---|
| WO | WO 2005/086713 | 9/2005 |
| WO | WO 2005/086713 A2 | 9/2005 |
| WO | WO2006/017759 * | 2/2006 |
| WO | WO 2006/017759 A2 | 2/2006 |
| WO | WO 2006/029045 | 3/2006 |
| WO | WO 2006/060719 A2 | 6/2006 |
| WO | WO 2006/116451 A2 | 11/2006 |
| WO | WO 2008/021288 | 2/2008 |
| WO | WO 2008/084331 | 7/2008 |
| WO | WO 2008/097908 | 8/2008 |
| WO | WO 2008/101118 | 8/2008 |
| WO | WO 2008/122936 | 10/2008 |
| WO | WO 2009/021322 | 2/2009 |
| WO | WO 2009/105549 | 8/2009 |
| WO | WO 2009/120877 | 10/2009 |
| WO | WO 2010/045714 | 4/2010 |
| WO | WO 2010/083252 | 7/2010 |

OTHER PUBLICATIONS

Bagley et al., "Endothelial precursor cells as a model of tumor endothelium: characterization and comparison with mature endothelial cells", Cancer Res., Sep. 15, 2003, 63, 5866-5873.

Banapour et al., "Characterization and epitope mapping of a human monoclonal antibody reactive with the envelope glycoprotein of human immunodeficiency virus", J. Immunol., Dec. 15, 1987, 139(12), 4027-4033.

Battle et al., "TEM1/Endosialin participates in cell-matrix and cell-cell adhesion interactions", abstract presented Apr. 16, 2007, Exhibit Hall, Los Angeles Convention Center.

Becker et al., "Tumor Stroma Marker Endosialin (Term1) is a Binding Partner of Metatasis-Related Protein Mac-2 BP/90K", The FASEB Journal, May 19, 2008, 22, 3059-3067.

Betsholtz, "Insight into the physiological functions of PDGF through genetic studies in mice", Cytokine Growth Factor Rev., Aug. 2004, 15(4), 215-228.

Boerner et al., "Production of antigen-specific human monoclonal antibodies from in vitro-primed human splenocytes", J. Immunol., Jul. 1, 1991, 147, 86-95.

Brady et al., "Human endosialin (tumor endothelial marker 1) is abundantly expressed in highly malignant and invasive brain tumors", JNL of Neuropatholgy and Experimental Neurology, Dec. 2004, 63(12), 1274-1283.

Bühring et al., "Expression of novel surface antigens on early hematopoietic cells", Ann. N.Y. Acad. Sci., Apr. 30, 1999, 872, 25-38.

Carson-Walter et al., "Characterization of TEM1/endosialin in human and murine brain tumors", BMC Cancer, 2009, Epub: Nov. 30, 2009, 9, 417, 1-13.

Carson-Walter et al., "Cell surface tumor endothelial markers are conserved in mice and humans", Cancer Res., Sep. 15, 2001, 61, 6649-6655.

Chothia et al., "Canonical Structures for the Hypervariable Regions of Immunoglobulins", J. Mol. Biol., Apr. 1987, 196, 901-917.

Choudhury et al., "c-Src couples PI 3 kinase/Akt and MAPK signaling to PDGF-induced DNA synthesis in mesangial cells", Cell Signal., Nov. 2006, 18(11), 1854-1864.

Christian et al., "Endosialin (Tem1) is a marker of tumor-associated myofibroblasts and tumor vessel-associated mural cells", The American Journal of Pathology, Feb. 2008, 172(2), 486-494.

Christian et al. "Molecular cloning and characterization of endosialin, a c-type lectin-like cell surface receptor of tumor endothelium", J. Bio Chem., American Soc of Biol chem Biologists, Mar. 2001, 276 (10) 7408-7414.

Christian et al., "Molecular cloning and characterization of EndoGlyx-1, an EMILIN-like multisubunit glycoprotein of vascular endothelium", J. Biol. Chem., Dec. 21, 2001, 276(10), 48588-48595.

Cole et al., (Reisfeld and Sell, Eds.), "The EBV-hybridoma technique and its application to human lung cancer", Monoclonal Antibodies and Cancer Therapy, UCLA Symposia on Molecular and Cellular Biology, New Series, Alan R. Liss, Inc., NY, 1985, 27, 77-96.

Conejo-Garcia et al., "Vascular leukocytes contribute to tumor vascularization", Blood, Jan. 15, 2005, 105(2), 679-681.

Das et al., "Retinal and choroidal angiogenesis: pathophysiology and strategies for inhibition", Prog. Retin. Eye Res., Nov. 2003, 22(6), 721-748.

Davies et al., "Levels of expression of endothelial markers specific to tumour-associated endothelial cells and their correlation with prognosis in patients with breast cancer", Clin. Exp. Metastasis, Sep. 2004, 21(1), 31-37.

Dhanabal, "Anti-angiogenic therapy as a cancer treatment paradigm", Curr. Med. Chem. Anti-Canc. Agents, Mar. 2005, 5, 115-130.

Dillman, "Monoclonal Antibodies for Treating Cancer", Ann. Internal Med., Oct. 1, 1989, 111, 592-603.

Dolznig et al., "Characterization of cancer stroma markers: in silico analysis of an mRNA expression database for fibroblast activation protein and endosialin", Cancer Immun., Aug. 2005, 5, 10.

Florell et al., "Preservation of RNA for functional genomic studies: a multidisciplinary tumor bank protocol", Mod. Pathol., Feb. 2001, 14(2), 116-128.

Foote et al., "Antibody Framework Residues Affecting the Conformation of the Hypervariable Loops", J. Mol. Biol., Mar. 1992, 224, 487-499.

Galiano et al., "Topical vascular endothelial growth factor accelerates diabetic wound healing through increased angiogenesis and by mobilizing and recruiting bone marrow-derived cells", Am. J. Pathol., Jun. 2004, 164(6), 1935-1947.

Garmestani et al., "Synthesis and evaluation of a macrocyclic bifunctional chelating agent for use with bismuth radionuclides", Nucl. Med. Biol., May 2001, 28, 409-418.

GenBank Accession No. AF279142, "*Homo sapiens* tumor endothelial marker 1 precursor (TEM1) mRAN, complete cds", Aug. 23, 2000.

Gerhardt & Betsholtz, "Endothelial-pericyte interactions in angiogenesis", Cell Tissue Res, Oct. 2003, Epub: Jul. 22, 2003, 314(1), 15-23.

Hanahan et al., "The hallmarks of cancer", Cell, Jan. 7, 2000, 100(1), 57-70.

Hauck et al., "Focal adhesion kinase facilitates platelet-derived growth factor-BB-stimulated ERK2 activation required for chemotaxis migration of vascular smooth muscle cells", J Biol. Chem., Dec. 29, 2000, 275(52), 41092-41099.

Heldin & Westermark, "Mechanism of action and in vivo role of platelet-derived growth factor", Physiol Rev., Oct. 1999, 79(4), 1283-1316.

Hellstrom et al., "Role of PDGF-B and PDGFR-beta in recruitment of vascular smooth muscle cells and pericytes during embryonic blood vessel formation in the mouse", Development, Jun. 1999, 126(14), 3047-3055.

Hollenbeck et al., "Type I collagen synergistically enhances PDGF-induced smooth muscle cell proliferation through pp60src-dependent crosstalk between the alpha2beta1 integrin and PDGFbeta receptor", Biochem. Biophys. Res Commun., Dec. 3, 2004, 325(1), 328-337.

Homandberg, "Potential regulation of cartilage metabolism in osteoarthritis by fibronectin fragments", Front Biosci., Oct. 15, 1999, 4, D713-730.

Huang et al., "Construction of representative immunoglobulin variable region cDNA libraries from human peripheral blood lymphocytes without in vitro stimulation", J. Immunol. Methods, Aug. 1991, 141, 227-236.

Huber et al., "Expression of stromal cell markers in distinct compartments of human skin cancers", J. Cutan. Pathol., Apr. 2006, 33, 145-155.

Hynes, "Integrins: Bidirectional, Allosteric Signaling Machines", Cell, Sep. 2002, 110, 673.

Jones et al., "Replacing the complementarity-determining regions in a human antibody with those from a mouse", Nature, May 1986, 321, 522-525.

Kala et al., "Phage Displayed Antibodies to Heat Stable Alkaline Phosphatase: Framework Region as a Determinant of Specificity", J. Biochem., Jun. 2002, 132, 535-541.

(56) References Cited

OTHER PUBLICATIONS

Khazaeli et al., "Human immune response to monoclonal antibodies", J. of Immunother., Jan. 1994, 15, 42-52.
Kikuchi et al., "Apoptosis inducing bivalent single-chain antibody fragments against CD47 showed antitumor potency for multiple myeloma", Leuk. Res., Apr. 2005, 29, 445-450.
Köhler et al., "Continuous cultures of fused cells secreting antibody of predefined specificity", Nature, Aug. 7, 1975, 256(5517), 495-497.
Kozbor et al., "The production of monoclonal antibodies from human lymphocytes", Immunol. Today, Mar. 1983, 4(3), 72-79.
Kreitman et al., "Immunotoxins for targeted cancer therapy", Adv. Drug Del. Rev., Apr. 1998, 31, 53-88.
Kuntz, "Structure-Based Strategies for Drug Design and Discovery", Science, Aug. 21, 1992, 257(5073), 1078-1082.
Kurosawa et al., "Genomic analysis of a murine cell-surface sialomucin, MGC-24/CD163", Eur. J. Biochem., Aug. 1999, 265, 466-472.
Kusano et al., "Immunocytochemical study on internalization of anti-carbohydrate monoclonal antibodies", Anticancer Res., Nov.-Dec. 1993, 13(6A), 2207-2212.
Kyriakos et al., "The fate of antibodies bound to the surface of tumor cells in vitro", Cancer Research, Feb. 15, 1992, 52(4), 835-842.
Labat-Robert, "Fibronectin in malignancy Effect on aging", Semin. Cancer Biol., Jun. 2002, 12, 187-195.
Leveen et al., "Mice deficient for PDGF B show renal, cardiovascular, and hematological abnormalities", Genes Dev., Aug. 1994, 8(16), 1875-1887.
Li et al., "Differential effects of imatinib on PDGF-induced proliferation and PDGF receptor signaling in human arterial and venous smooth muscle cells", J Cell Biochem., Dec. 15, 2006, 99(6), 1553-1563.
Lindahl et al., "Pericyte loss and microaneurysm formation in PDGF-B-deficient mice", Science, Jul. 11, 1997, 277(5323), 242-245.
MacFadyen et al., "Endosialin is expressed on stromal fibroblasts and CNS pericytes in mouse embryos and is downregulated during development", Gene Expression Patterns, Epub: Jul. 27, 2006, Jan. 2007, 7(3), 363-369.
MacFadyen et al., "Endosialin (TEM1, CD248) is a marker of stromal fibroblasts and is not selectively expressed on tumour endothelium", FEBS, Apr. 2005, 579, 2569-2575.
Magnusson & Mosher, "Fibronectin: structure, assembly, and cardiovascular implications", Arterioscler. Thromb. Vasc. Biol., May 1998, 18, 1363-1370.
Marks et al., "By-passing immunization. Human antibodies from V-gene libraries displayed on phage", J. Mol. Biol., Dec. 5, 1991, 222(3), 581-597.
Marty et al., "Isolation and characterization of a scfv antibody specific for tumor endothelial marker 1 (tem1), a new reagent for targeted tumor therapy", Cancer Letters, Apr. 28, 2006, 235(2), 298-308.
McKeown-Longo & Mosher, "Binding of plasma fibronectin to cell layers of human skin fibroblasts", J. Cell Biol., Aug. 1983, 97, 466-472.
McKeown-Longo & Mosher, "Interaction of the 70,000-mol-wt amino-terminal fragment of fibronectin with the matrix-assembly receptor of fibroblasts", J. Cell Biol., Feb. 1985, 100, 364-374.
Miller et al, "Ligand binding to proteins: the binding landscape model", Protein Sci., Oct. 1997, 6(10), 2166-2179.
Millette et al., "Platelet-derived growth factor-BB transactivates the fibroblast growth factor receptor to induce proliferation in human smooth muscle cells", Trends Cardiovasc. Med., Jan. 2006, 16(1), 25-28.
Modzelewski et al., "Isolation and Identification of Fresh Tumor-derived Endothelial Cells from a Murine RIF-1 Fibrosarcoma", Cancer Res., Jan. 1994, 54, 336-339.
Morea et al., "Conformations of the Third Hypervariable Region in the VH Domain of Immunoglobulins", J. Mol. Biol., Jan. 1998, 275, 269-294.
Morrison et al., "Chimeric human antibody molecules: mouse antigen-binding domains with human constant region domains", Proc. Natl. Acad. Sci. USA, Nov. 1984, 81(21), 6851-6855.
Naito et al., "Ets-1 is an early response gene activated by ET-1 and PDGF-BB in vascular smooth muscle cells", Am. J Physiol, Feb. 1998, 274(2 pt. 1), C472-C480.
Nanda et al., "Tumor endothelial marker 1 (Tem1) functions in the growth and progression of abdominal tumors", Proc. Natl. Acad. Sci. USA, Feb. 28, 2006, 103, 3351-3356.
Niwa et al., "Defucosylated chimeric anti-CC chemokine receptor 4 IgG1 with enhanced antibody-dependent cellular cytotoxicity shows potent therapeutic activity to T-cell leukemia and lymphoma", Cancer Res., Mar. 15, 2004, 64, 2127-2133.
Ohradanova et al., "Hypoxia upregulates expression of human endosialin gene via hypoxia-inducible factor 2", Br J Cancer, Oct. 21, 2008, Epub: Sep. 23, 2008, 99(8), 1348-1356.
Opavsky et al., "Molecular characterization of the mouse Tem1/endosialin gene regulated by cell density in vitro and expressed in normal tissues in vivo", J. Biol. Chem., Oct. 2001, 276(42), 38795-38807.
Orlandi et al., "Cloning immunoglobulin variable domains for expression by the polymerase chain reaction", Proc. Natl. Acad. Sci. USA, May 1, 1989, 86, 3833-3837.
Paleolog and Miotla, "Angiogenesis in arthritis: role in disease pathogenesis and as a potential therapeutic target", Angiogenesis, Dec. 1998, 2(4), 295-307.
Panka et al., "Variable region framework differences result in decreased or increased affinity of variant anti-digoxin antibodies", Proc. Natl. Acad. Sci. USA, May 1988, 85, 3080-3084.
Persson et al., "Generation of diverse high-affinity human monoclonal antibodies by repertoire cloning", Proc. Natl. Acad. Sci. USA, Mar. 1991, 88, 2432-2436.
Peters et al., "Contribution of bone marrow-derived endothelial cells to human tumor vasculature," Nat. Med., Feb. 2005, 11, 261-262.
Presta, "Antibody Engineering", Curr. Op. Struct. Biol., Aug. 1992, 3(4), 593-596.
Queen et al., "A humanized antibody that binds to the interleukin 2 receptor", Proc. Nat. Acad. Sci. USA, Dec. 1989, 86(24), 10029-10033.
Reichmann et al., "Reshaping human antibodies for therapy", Nature, Mar. 1988, 332(6162), 323-327.
Rettig et al., "Identification of endosialin, a cell surface glycoprotein of vascular endothelial cells in human cancer", Proc. Natl. Acad. Sci. USA, Nov. 1992, 89, 10832-10836.
Rmali et al., "Prognostic values of tumor endothelial markers in patients with colorectal cancer", World J. Gastroenterol., Mar. 2005, 11, 1283-1286.
Ruoslahti et al., "Alignment of biologically active domains in the fibronectin molecule", J. Biol. Chem., Jul. 1981, 256, 7277-7281.
Rupp et al., "Mouse endosialin, a C-type lectin-like cell surface receptor: expression during embryonic development and induction in experimental cancer neoangiogenesis", Cancer Immun, Jul. 31, 2006, 6, 10.
Scott et al., "Immunological effects of chimeric anti-GD3 monoclonal antibody KM871 in patients with metastatic melanoma", Cancer Immun., Feb. 2005, 22, 5(3), 1-12.
SIGMA® Product Information Sheet, Product No. F 0162, Fibronectin Proteolytic Fragment, 45 kDa from human plasma, 1 page, No date available.
SIGMA® Product Information Sheet, Product No. F 0287, Fibronectin Proteolytic Fragment, 70 kDa from human plasma, 1 page, No date available.
SIGMA® Product Information Sheet, Product No. F 9911, Fibronectin Proteolytic Fragment, 30 kDa from human plasma, 1 page, No date available.
Song et al., "PDGFRbeta+ perivascular progenitor cells in tumours regulate pericyte differentiation and vascular survival", Nat Cell Biol, Sep. 2005, Epub: Aug. 21, 2005, 7(9), 870-879.
Soriano, "Abnormal kidney development and hematological disorders in PDGF beta-receptor mutant mice", Genes Dev., Aug. 15, 1994, 8(16), 1888-1896.
St. Croix et al., MPsrch search result, ABB90271, "Human Tumor Endothelial Marker Polypeptide", May 30, 2002, 5 pages.

(56) References Cited

OTHER PUBLICATIONS

St. Croix et al., "Genes expressed in human tumor endothelium", Science, Aug. 2000, 289(5482), 1197-1202.

Sun et al., "Antitumor activity of a chimeric antibody against the leucocyte antigen CD48", Cancer Immunol. Immunther., Jan. 2000, 48(10), 595-602.

Tempest et al., "Reshaping a human monoclonal antibody to inhibit human respiratory syncytial virus infection in vivo", Biotechnology, Mar. 1991, 9(3), 266-271.

Tomasini-Johansson et al., "The N-terminal 70-kDa fragment of fibronectin binds to cell surface fibronectin assembly sites in the absence of intact fibronectin", Matrix Biol., Jul. 2006, 25, 282-293.

Tomkowicz et al., "Interaction of endosialin.tem1 with extracellular matrix proteins medicates cell adhesion and migration", Proceedings of the Natl. Acad. of Sci, USA, Nov. 13, 2007, Epub: Nov. 6, 2007, 104(46), 17965-17970.

Trail et al., "Monoclonal antibody drug immunoconjugates for targeted treatment of cancer", Cancer Immunology, Jan. 2003, 328-337.

Verhoeyen et al., "Reshaping human antibodies: grafting an antilysozyme activity", Science, Mar. 1988, 239, 1534-1536.

Virgintino et al., "An intimate interplay between precocious, migrating pericytes and endothelial cells governs human fetal brain angiogenesis", Angiogenesis, Jan. 2007, 10, 35-45.

Watt et al., "CD164, a novel sialomucin on CD34(+) and erythroid subsets, is located on human chromosome 6q21", Blood, Aug. 1998, 92(3), 849-866.

Watt et al., "CD164—a novel sialomucin on CD34+ cells", Leuk. Lymphoma., Mar. 2000, 37(1-2), 1-25.

Wierzbicka-Patynowski & Schwarzbauer, "The ins and outs of fibronectin matrix assembly", J. Cell Sci., Aug. 15, 2003, 116(Pt 16), 3269-3276.

Wilkinson-Berka, "Vasoactive factors and diabetic retinopathy: vascular endothelial growth factor, cycoloxygenase-2 and nitric oxide", Curr. Pharm. Des., Oct. 2004, 10(27), 3331-3348.

Wolff et al., "Monoclonal antibody homodimers: enhanced antitumor activity in nude mice", Cancer Res., Jun. 1993, 53(11), 2560-2565.

Yancopoulos et al., "Vascular-specific growth factors and blood vessel formation", Nature, Sep. 2000, 407(6801), 242-248.

Zafiropoulos et al., "Induction of antigen-specific isotype switching by in vitro immunization of human naïve B lymphocytes", J. Immunological Methods, Jan. 15, 1997, 200(1-2), 181-190.

Zannettino et al., "The sialomucin CD164 (MGC-24v) is an adhesive glycoprotein expressed by human hematopoietic progenitors and bone marrow stromal cells that serves as a potent negative regulator of hematopoiesis", Blood, Oct. 15, 1998, 92(8), 2613-2628.

Ruoslahti et al., "Targeting of Drugs and Nanoparticles to Tumors", The Journal of Cell Biology, Mar. 15, 2010, 188(6), 759-768.

Tomkowicz et al., "Endosialin/TEM-1/CD248 Regulates Pericyte Proliferation Through PDGF Receptor Signaling", Cancer Biology and Therapy, Jun. 1, 2010, 9(11), 1-8.

Rouleau et al., "Endosialin Protein Expression and Therapeutic Target Potential in Human Solid Tumors; Sarcoma Versus Carcinoma", Clinical Cancer Research, Nov. 14, 2008, 14(22), 7223-7226.

Rupp et al., "Laser Capture Microdissection of Epithelial Cancers Guided by Antibodies Against Fibroblast Activation Protein and Endosialin", Diagnostic Molecular Pathology, Mar. 2006, 15(1), 35-42.

European Application No. EP 13162773: Extended European Search Report dated Jun. 24, 2013, 6 pages.

\* cited by examiner

FN Protein Fragments

Treatment

SEQUENCE LISTING

<160> NUMBER OF SEQ ID NOS: 35

<210> SEQ ID NO 1
<211> LENGTH: 2660
<212> TYPE: DNA
<213> ORGANISM: Mus musculus

<400> SEQUENCE: 1

```
gtcaagagca gcggcaggcc cgagccgggc cagtcggggg gcgtcgcgat gctgctgcgc      60
ctgctgctgg cctgggtggc cgcggtgccc gcactgggcc aggtcccctg gacgccggag     120
cctcgagccg cgtgcggccc cagcagctgc tacgcgctct ttccccggcg ccgcacattc     180
ctggaagctt ggcgggcgtg ccgcgaattg ggggcaacc tggccacacc gcggacccca     240
gaggaggccc agcgtgtgga cagcctggtg ggggtcgggc cggccaacgg gctgctatgg     300
attgggttgc agcggcaggc taggcaatgc cagccgcagc gcccactgcg gggcttcata     360
tggaccacgg gagaccagga caccgccttc accaactggg cccagccggc tacggaagga     420
ccctgcccag cccagcgctg tgcagcccct gaggccagcg gagagcatcg ctggctcgaa     480
ggctcgtgca cactggctgt cgatggctac ctctgccagt ttggttttga gggtgcctgc     540
cctgccttgc cgcttgaggt gggtcaggcc ggtcccgctg tctacaccac acccttcaac     600
ctggtttcca gcgagttcga atggctgccc tttggctccg tggcagctgt gcagtgccaa     660
gctggcaggg gagcttctct gctgtgcgtg aaacagcctt caggtggcgt gggctggtcc     720
```

```
cagactggcc cgctgtgccc agggactggc tgtggtcctg acaatggggg ttgcgaacat    780
gagtgtgtgg aagaggtgga cggtgctgtg tcctgccgct gcagtgaagg cttccgtcta    840
gcagcagatg ggcacagttg tgaagacccc tgtgcccagg cccctgtga gcagcagtgt     900
gaacctggag ggccacaagg ctatagctgc cactgtcgcc ttggcttccg gccagctgag    960
gatgatccac accgctgcgt ggacacggat gagtgccaga ttgctggtgt gtgccagcag   1020
atgtgtgtca actatgttgg tggctttgag tgttactgca gcgagggtca cgagcttgag   1080
gcagatggta tcagctgtag ccctgcagga gccatgggtg cccaggcttc ccaggatctc   1140
agagatgagt gctggatga tggagaagaa ggggaggatg aagaggagcc ctgggaggac    1200
tttgatggca cctggacaga ggaacagggg atcctatggc tggcacctac acatccacct   1260
gactttggcc tgccctatag gcccaacttc ccacaggatg agagcctca gagattgcac    1320
ctggagccta cctggccacc cccacttagt gcccccaggg gcccctacca ctcctcagtg   1380
gtgtctgcca cacggcccat ggtgatctct gccactcgac ccacactacc ttctgcccac   1440
aagacctctg ttatttcagc tacacgccca ccctgagcc ctgtccaccc acctgccatg    1500
gcccctgcca cacctccagc tgtgttctct gagcaccaga tccccaaaat caaggccaat   1560
tatccagacc tgccttttgg ccacaagcct gggataacct cggccactca cccagcacgg   1620
tctcctccgt accagccccc cattatctca accaactatc cccaagtctt ccctccccac   1680
caggcccta tgtctccaga tacccacact atcacttatt gcctccagt cccccctcac     1740
cttgatcctg gggataccac ttctaaagcc catcaacacc ctttgctccc agatgctcca   1800
ggtatcagaa cccaggcccc ccagctttct gtctcagctc tccagccccc tcttcctacc   1860
aactccaggt cttctgtcca tgaaactcct gtgcctgctg ccaaccagcc cccagccttc   1920
ccttcttctc ccctccccc tcagaggccc actaaccaga cctcatctat cagccctaca   1980
cattcctatt ccagagcccc tctagtccca agggaaggag ttcccagtcc caaatcagtg   2040
ccacagctgc cctcggtgcc ctccacagca gctccaacag ccctggcaga gtcaggtctt   2100
gcaggccaaa gccaaaggga tgaccgctgg ctgctggtgg cactcctggt gccaacatgt   2160
gtcttcttgg tggtgctgct tgccctgggc attgtgtact gcactcgctg tggctcccac   2220
gcacccaaca gcggatcac ggactgctat cgctgggtca cacatgctgg aacaagagc    2280
tcaacagaac ccatgccccc cagaggcagc cttacagggg tacagacctg tagaaccagt   2340
gtgtgatggg gtgcagatgc ccctttgtgg gatagaagaa aaggacttgc tttggacaca   2400
tggctgagac cacaccaagg acttatgggg gctgcccagc tgcagagga ggttctgttc    2460
tttgagccca gcatccatgg caaaggacac accaggactc caggacctca aggggtgggt   2520
gctgggatct tctccaataa atggggtgcc aacctcacccc aaaaaaaaaa aaaaaaaaa   2580
aaaaaaaaa aaaaaaaaa aaaaaaaaa aaaaaaaaa aaaaaaaaa aaaaaaaaa        2640
aaaaaaaaa aaaaaaaaa                                                  2660

<210> SEQ ID NO 2
<211> LENGTH: 765
<212> TYPE: PRT
<213> ORGANISM: Mus musculus

<400> SEQUENCE: 2

Met Leu Leu Arg Leu Leu Leu Ala Trp Val Ala Ala Val Pro Ala Leu
1               5                   10                  15

Gly Gln Val Pro Trp Thr Pro Glu Pro Arg Ala Ala Cys Gly Pro Ser
```

```
                    20                  25                  30
Ser Cys Tyr Ala Leu Phe Pro Arg Arg Thr Phe Leu Glu Ala Trp
                35                  40                  45

Arg Ala Cys Arg Glu Leu Gly Gly Asn Leu Ala Thr Pro Arg Thr Pro
        50                  55                  60

Glu Glu Ala Gln Arg Val Asp Ser Leu Val Gly Val Gly Pro Ala Asn
65                  70                  75                  80

Gly Leu Leu Trp Ile Gly Leu Gln Arg Gln Ala Arg Gln Cys Gln Pro
                85                  90                  95

Gln Arg Pro Leu Arg Gly Phe Ile Trp Thr Thr Gly Asp Gln Asp Thr
            100                 105                 110

Ala Phe Thr Asn Trp Ala Gln Pro Ala Thr Glu Gly Pro Cys Pro Ala
            115                 120                 125

Gln Arg Cys Ala Ala Leu Glu Ala Ser Gly Glu His Arg Trp Leu Glu
            130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Pro Leu Glu Val Gly Gln Ala Gly Pro
                165                 170                 175

Ala Val Tyr Thr Thr Pro Phe Asn Leu Val Ser Ser Glu Phe Glu Trp
            180                 185                 190

Leu Pro Phe Gly Ser Val Ala Ala Val Gln Cys Gln Ala Gly Arg Gly
            195                 200                 205

Ala Ser Leu Leu Cys Val Lys Gln Pro Ser Gly Gly Val Gly Trp Ser
            210                 215                 220

Gln Thr Gly Pro Leu Cys Pro Gly Thr Gly Cys Gly Pro Asp Asn Gly
225                 230                 235                 240

Gly Cys Glu His Glu Cys Val Glu Val Asp Gly Ala Val Ser Cys
                245                 250                 255

Arg Cys Ser Glu Gly Phe Arg Leu Ala Ala Asp Gly His Ser Cys Glu
            260                 265                 270

Asp Pro Cys Ala Gln Ala Pro Cys Glu Gln Cys Glu Pro Gly Gly
            275                 280                 285

Pro Gln Gly Tyr Ser Cys His Cys Arg Leu Gly Phe Arg Pro Ala Glu
            290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
            340                 345                 350

Ala Gly Ala Met Gly Ala Gln Ala Ser Gln Asp Leu Arg Asp Glu Leu
            355                 360                 365

Leu Asp Asp Gly Glu Gly Glu Asp Glu Glu Pro Trp Glu Asp
            370                 375                 380

Phe Asp Gly Thr Trp Thr Glu Glu Gln Gly Ile Leu Trp Leu Ala Pro
385                 390                 395                 400

Thr His Pro Pro Asp Phe Gly Leu Pro Tyr Arg Pro Asn Phe Pro Gln
                405                 410                 415

Asp Gly Glu Pro Gln Arg Leu His Leu Glu Pro Thr Trp Pro Pro Pro
            420                 425                 430

Leu Ser Ala Pro Arg Gly Pro Tyr His Ser Ser Val Val Ser Ala Thr
            435                 440                 445
```

```
Arg Pro Met Val Ile Ser Ala Thr Arg Pro Thr Leu Pro Ser Ala His
    450                 455                 460

Lys Thr Ser Val Ile Ser Ala Thr Arg Pro Pro Leu Ser Pro Val His
465                 470                 475                 480

Pro Pro Ala Met Ala Pro Ala Thr Pro Pro Ala Val Phe Ser Glu His
                485                 490                 495

Gln Ile Pro Lys Ile Lys Ala Asn Tyr Pro Asp Leu Pro Phe Gly His
                500                 505                 510

Lys Pro Gly Ile Thr Ser Ala Thr His Pro Ala Arg Ser Pro Pro Tyr
            515                 520                 525

Gln Pro Pro Ile Ile Ser Thr Asn Tyr Pro Gln Val Phe Pro Pro His
            530                 535                 540

Gln Ala Pro Met Ser Pro Asp Thr His Thr Ile Thr Tyr Leu Pro Pro
545                 550                 555                 560

Val Pro Pro His Leu Asp Pro Gly Asp Thr Thr Ser Lys Ala His Gln
                565                 570                 575

His Pro Leu Leu Pro Asp Ala Pro Gly Ile Arg Thr Gln Ala Pro Gln
                580                 585                 590

Leu Ser Val Ser Ala Leu Gln Pro Pro Leu Pro Thr Asn Ser Arg Ser
            595                 600                 605

Ser Val His Glu Thr Pro Val Pro Ala Ala Asn Gln Pro Pro Ala Phe
            610                 615                 620

Pro Ser Ser Pro Leu Pro Pro Gln Arg Pro Thr Asn Gln Thr Ser Ser
625                 630                 635                 640

Ile Ser Pro Thr His Ser Tyr Ser Arg Ala Pro Leu Val Pro Arg Glu
                645                 650                 655

Gly Val Pro Ser Pro Lys Ser Val Pro Gln Leu Pro Ser Val Pro Ser
                660                 665                 670

Thr Ala Ala Pro Thr Ala Leu Ala Glu Ser Gly Leu Ala Gly Gln Ser
            675                 680                 685

Gln Arg Asp Asp Arg Trp Leu Leu Val Ala Leu Leu Val Pro Thr Cys
            690                 695                 700

Val Phe Leu Val Val Leu Leu Ala Leu Gly Ile Val Tyr Cys Thr Arg
705                 710                 715                 720

Cys Gly Ser His Ala Pro Asn Lys Arg Ile Thr Asp Cys Tyr Arg Trp
                725                 730                 735

Val Thr His Ala Gly Asn Lys Ser Ser Thr Glu Pro Met Pro Pro Arg
            740                 745                 750

Gly Ser Leu Thr Gly Val Gln Thr Cys Arg Thr Ser Val
            755                 760                 765

<210> SEQ ID NO 3
<211> LENGTH: 2576
<212> TYPE: DNA
<213> ORGANISM: Homo sapiens

<400> SEQUENCE: 3
agtccggggg catcgcgatg ctgctgcgcc tgttgctggc ctgggcggcc gcagggccca      60
cactgggcca ggaccctgg gctgctgagc cccgtgccgc ctgcggcccc agcagctgct     120
acgctctctt cccacggcgc cgcaccttcc tggaggcctg gcgggcctgc cgcgagctgg     180
ggggcgacct ggccactcct cggaccccccg aggaggccca gcgtgtggac agcctggtgg    240
gtgcgggccc agcagccgg ctgctgtgga tcgggctgca gcggcaggcc cggcaatgcc     300
```

```
agctgcagcg cccactgcgc ggcttcacgt ggaccacagg ggaccaggac acggctttca    360
ccaactgggc ccagccagcc tctggaggcc cctgcccggc ccagcgctgt gtggccctgg    420
aggcaagtgg cgagcaccgc tggctggagg gctcgtgcac gctggctgtc gacggctacc    480
tgtgccagtt tggcttcgag ggcgcctgcc cggcgctgca agatgaggcg ggccaggccg    540
gcccagccgt gtataccacg cccttccacc tggtctccac agagtttgag tggctgccct    600
tcggctctgt ggccgctgtg cagtgccagg ctggcagggg agcctctctg ctctgcgtga    660
agcagcctga gggaggtgtg ggctggtcac gggctgggcc cctgtgcctg gggactggct    720
gcagccctga caacgggggc tgcgaacacg aatgtgtgga ggaggtggat ggtcacgtgt    780
cctgccgctg cactgagggc ttccggctgg cagcagacgg gcgcagttgc gaggacccct    840
gtgcccaggc tccgtgcgag cagcagtgtg agcccgtgg ggccacaaggc tacagctgcc    900
actgtcgcct gggtttccgg ccagcggagg atgatccgca ccgctgtgtg gacacagatg    960
agtgccagat tgccggtgtg tgccagcaga tgtgtgtcaa ctacgttggt ggcttcgagt   1020
gttattgtag cgagggacat gagctggagg ctgatgcat cagctgcagc cctgcagggg   1080
ccatgggtgc ccaggcttcc caggacctcg gagatgagtt gctggatgac ggggaggatg   1140
aggaagatga agacgaggcc tggaaggcct tcaacggtgg ctggacggag atgcctggga   1200
tcctgtggat ggagcctacg cagccgcctg actttgccct ggcctataga ccgagcttcc   1260
cagaggacag agagccacag ataccctacc cggagcccac ctggccaccc ccgctcagtg   1320
cccccagggt cccctaccac tcctcagtgc tctccgtcac ccggcctgtg gtggtctctg   1380
ccacgcatcc cacactgcct tctgcccacc agcctcctgt gatccctgcc acacacccag   1440
ctttgtcccg tgaccaccag atccccgtga tcgcagccaa ctatccagat ctgccttctg   1500
cctaccaacc cggtattctc tctgtctctc attcagcaca gcctcctgcc caccagcccc   1560
ctatgatctc aaccaaatat ccggagctct ccctgcccca ccagtccccc atgtttccag   1620
acacccgggt cgctggcacc cagaccacca ctcatttgcc tggaatccca cctaaccatg   1680
cccctctggt caccacccctc ggtgcccagc tacccctca agccccagat gcccttgtcc   1740
tcagaaccca ggcacccag cttcccatta tcccaactgc ccagccctct ctgaccacca   1800
cctccaggtc ccctgtgtct cctgcccatc aaatctctgt gcctgctgcc acccagcccg   1860
cagccctccc caccctcctg ccctctcaga gccccactaa ccagacctca cccatcagcc   1920
ctacacatcc ccattccaaa gcccccaaa tcccaaggga gatggcccc agtcccaagt   1980
tggccctgtg gctgccctca ccagctccca gcagcccc aacagccctg ggggaggctg   2040
gtcttgccga gcacagccag agggatgacc ggtggctgct ggtggcactc ctggtgccaa   2100
cgtgtgtctt tttggtggtc ctgcttgcac tgggcatcgt gtactgcacc cgctgtggcc   2160
cccatgcacc caacaagcgc atcactgact gctatcgctg ggtcatccat gctgggagca   2220
agagcccaac agaacccatg cccccaggg gcagcctcac aggggtgcag acctgcagaa   2280
ccagcgtgtg atggggtgca gaccccctc atggagtatg ggcgctgga cacatggccg   2340
gggctgcacc agggacccat gggggctgcc cagctggaca gatggcttcc tgctccccag   2400
gcccagccag ggtcctctct caaccactag acttggctct caggaactct gcttcctggc   2460
ccagcgctcg tgaccaagga taccaaaag cccttaagac ctcaggggc gggtgctggg   2520
gtcttctcca ataaatgggg tgtcaacctt acccaaggaa aaaaaaaaa aaaaaa         2576

<210> SEQ ID NO 4
<211> LENGTH: 757
```

<212> TYPE: PRT
<213> ORGANISM: Homo sapiens

<400> SEQUENCE: 4

Met Leu Leu Arg Leu Leu Ala Trp Ala Ala Gly Pro Thr Leu
1               5                   10                  15

Gly Gln Asp Pro Trp Ala Ala Glu Pro Arg Ala Ala Cys Gly Pro Ser
            20                  25                  30

Ser Cys Tyr Ala Leu Phe Pro Arg Arg Thr Phe Leu Glu Ala Trp
        35                  40                  45

Arg Ala Cys Arg Glu Leu Gly Gly Asp Leu Ala Thr Pro Arg Thr Pro
50                  55                  60

Glu Glu Ala Gln Arg Val Asp Ser Leu Val Gly Ala Gly Pro Ala Ser
65                  70                  75                  80

Arg Leu Leu Trp Ile Gly Leu Gln Arg Gln Ala Arg Gln Cys Gln Leu
                85                  90                  95

Gln Arg Pro Leu Arg Gly Phe Thr Trp Thr Thr Gly Asp Gln Asp Thr
            100                 105                 110

Ala Phe Thr Asn Trp Ala Gln Pro Ala Ser Gly Gly Pro Cys Pro Ala
        115                 120                 125

Gln Arg Cys Val Ala Leu Glu Ala Ser Gly Glu His Arg Trp Leu Glu
130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Gln Asp Glu Ala Gly Gln Ala Gly Pro
                165                 170                 175

Ala Val Tyr Thr Thr Pro Phe His Leu Val Ser Thr Glu Phe Glu Trp
            180                 185                 190

Leu Pro Phe Gly Ser Val Ala Ala Val Gln Cys Gln Ala Gly Arg Gly
        195                 200                 205

Ala Ser Leu Leu Cys Val Lys Gln Pro Glu Gly Gly Val Gly Trp Ser
210                 215                 220

Arg Ala Gly Pro Leu Cys Leu Gly Thr Gly Cys Ser Pro Asp Asn Gly
225                 230                 235                 240

Gly Cys Glu His Glu Cys Val Glu Glu Val Asp Gly His Val Ser Cys
                245                 250                 255

Arg Cys Thr Glu Gly Phe Arg Leu Ala Ala Asp Gly Arg Ser Cys Glu
            260                 265                 270

Asp Pro Cys Ala Gln Ala Pro Cys Glu Gln Gln Cys Glu Pro Gly Gly
        275                 280                 285

Pro Gln Gly Tyr Ser Cys His Cys Arg Leu Gly Phe Arg Pro Ala Glu
290                 295                 300

Asp Asp Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Ser Glu Gly His Glu Leu Glu Ala Asp Gly Ile Ser Cys Ser Pro
            340                 345                 350

Ala Gly Ala Met Gly Ala Gln Ala Ser Gln Asp Leu Gly Asp Glu Leu
        355                 360                 365

Leu Asp Asp Gly Glu Asp Glu Glu Asp Glu Asp Glu Ala Trp Lys Ala
370                 375                 380

Phe Asn Gly Gly Trp Thr Glu Met Pro Gly Ile Leu Trp Met Glu Pro
385                 390                 395                 400

```
Thr Gln Pro Pro Asp Phe Ala Leu Ala Tyr Arg Pro Ser Phe Pro Glu
                405                 410                 415

Asp Arg Glu Pro Gln Ile Pro Tyr Pro Glu Pro Thr Trp Pro Pro Pro
            420                 425                 430

Leu Ser Ala Pro Arg Val Pro Tyr His Ser Ser Val Leu Ser Val Thr
        435                 440                 445

Arg Pro Val Val Ser Ala Thr His Pro Thr Leu Pro Ser Ala His
    450                 455                 460

Gln Pro Pro Val Ile Pro Ala Thr His Pro Ala Leu Ser Arg Asp His
465                 470                 475                 480

Gln Ile Pro Val Ile Ala Ala Asn Tyr Pro Asp Leu Pro Ser Ala Tyr
                485                 490                 495

Gln Pro Gly Ile Leu Ser Val Ser His Ser Ala Gln Pro Pro Ala His
            500                 505                 510

Gln Pro Pro Met Ile Ser Thr Lys Tyr Pro Glu Leu Phe Pro Ala His
        515                 520                 525

Gln Ser Pro Met Phe Pro Asp Thr Arg Val Ala Gly Thr Gln Thr Thr
    530                 535                 540

Thr His Leu Pro Gly Ile Pro Pro Asn His Ala Pro Leu Val Thr Thr
545                 550                 555                 560

Leu Gly Ala Gln Leu Pro Pro Gln Ala Pro Asp Ala Leu Val Leu Arg
                565                 570                 575

Thr Gln Ala Thr Gln Leu Pro Ile Ile Pro Thr Ala Gln Pro Ser Leu
            580                 585                 590

Thr Thr Thr Ser Arg Ser Pro Val Ser Pro Ala His Gln Ile Ser Val
        595                 600                 605

Pro Ala Ala Thr Gln Pro Ala Ala Leu Pro Thr Leu Leu Pro Ser Gln
    610                 615                 620

Ser Pro Thr Asn Gln Thr Ser Pro Ile Ser Pro Thr His Pro His Ser
625                 630                 635                 640

Lys Ala Pro Gln Ile Pro Arg Glu Asp Gly Pro Ser Pro Lys Leu Ala
                645                 650                 655

Leu Trp Leu Pro Ser Pro Ala Pro Thr Ala Ala Pro Thr Ala Leu Gly
            660                 665                 670

Glu Ala Gly Leu Ala Glu His Ser Gln Arg Asp Asp Arg Trp Leu Leu
        675                 680                 685

Val Ala Leu Leu Val Pro Thr Cys Val Phe Leu Val Val Leu Leu Ala
    690                 695                 700

Leu Gly Ile Val Tyr Cys Thr Arg Cys Gly Pro His Ala Pro Asn Lys
705                 710                 715                 720

Arg Ile Thr Asp Cys Tyr Arg Trp Val Ile His Ala Gly Ser Lys Ser
                725                 730                 735

Pro Thr Glu Pro Met Pro Pro Arg Gly Ser Leu Thr Gly Val Gln Thr
            740                 745                 750

Cys Arg Thr Ser Val
        755

<210> SEQ ID NO 5
<211> LENGTH: 2397
<212> TYPE: DNA
<213> ORGANISM: Rattus rattus

<400> SEQUENCE: 5
atgctgctgc gcctgctgct ggcctgggcg gcgcggtgc ccgcactggg ccaggccccc      60
```

| | |
|---|---|
| tggacgccgg agcctagagc cgcctgcggc cccagcagct gctacgctct ctttccccgg | 120 |
| cgccgcacat tcctggaggc ttggcggtcg tgccgcgaat tgggggggcaa cctggccaca | 180 |
| ccgaggaccc cggaggaggc ccgacgtgtg gacagcctgg tgggcgtcgg acccgccaac | 240 |
| gggctgctat ggattgggtt gcagcggcag gctcggcaat gccagccaca cgcccactg | 300 |
| cggggcttca tatggaccac gggagaccag gacaccgcct tcactaactg ggcccagccg | 360 |
| gctacggaag gaccctgccc ggcccagcgc tgtgctgccc ttgaggccag cggagaacat | 420 |
| cgctggctcg aaggctcgtg cacactggct gtcgatggct acctctgcca gtttggtttt | 480 |
| gagggtgcct gtcctgcctt gccgcttgag gtgggccaag ccgtccagc tatctacacc | 540 |
| acacccttca acctggtttc cagtgagttc gaatggctac cctttggctc cgtggcagct | 600 |
| gtgcagtgcc aagctggcag ggaacgtctc tgttgtgtg tgaaacaacc ttcaggtggc | 660 |
| gttggctggt cccagactgg cccactgtgt ccagggactg gctgtggtcc tgacaatggg | 720 |
| ggttgcgaac atgaatgtgt ggaagagttg gatggcggta tgtcctgccg ctgcagtgaa | 780 |
| ggcttccgtc tagcagcaga tgggcacagt tgtgaagacc cttgtgccca ggcccctgt | 840 |
| gagcagcagt gtgagcctgg tgggccacaa ggctacagct gccactgtcg cctaggcttc | 900 |
| cggccagctg aggatgagcc acaccgctgc gtggacacgg atgagtgcca gattgctggt | 960 |
| gtgtgccagc agatgtgtgt caactatgtt ggtggctttg agtgttactg cagggagggt | 1020 |
| catgagcttg aggcagatgg tatcagttgt agccctgcag gagctatggg tgcccaggct | 1080 |
| tcccaggatc ttagagacga gttgctggat gatggagaag aagggagga tgaagaggag | 1140 |
| ccctgggagg acttcgatgg cacctggaca gaggagcagg ggaccctatg gatggcacct | 1200 |
| acacatccgc ctgactttgg cctgccctat aggcccaact tcccacagga tggagagcct | 1260 |
| cagagattgc acctggagcc tacctggcca cccccactta gcgccccag ggcccctac | 1320 |
| cactcctcag tggtgtctgc cacacggcc atggtaatct ctgccactcg acccacacaa | 1380 |
| ccttctgccc gaaagacctc tgttatttca gccacacacc taccccttaa ccctgtccac | 1440 |
| ccacctgccc tagcccctac cacacctcca gccgtgctcc ctgagcacca gatccccaaa | 1500 |
| atcaaggcca gttatccaga cttgcctttt ggccacaagc ctgggataac ctcagccact | 1560 |
| cacccagcac agcctcctcc tcaccagccc cccatcatct caacgaaata tcccaagtc | 1620 |
| ttccctcccc agcaggcccc tatgtctcca gacacccaca ctatcactaa tttgcctcta | 1680 |
| atcccatctc accttgaccc tggggatacc acttcccaag ccggtcacca tcctttgctc | 1740 |
| ccagatgttc caggtatcag aacccaggct ccccaggttt ctgtctcagc tctccagccc | 1800 |
| tctctgccta ccaactccag gtcttctgtc catgaacccc ctgtgcctac tgccaaccag | 1860 |
| cccccagcct tccttctcc cctgcccct cagagcccca ttaaccagac ctcatctatc | 1920 |
| agccctacac actcctattc cagagcccct caggtcccaa gggaaggagc tcccagtccc | 1980 |
| aaatcagtgc caaggctgca ctcagtggcc cccacagcag ctccaacagc cctggcagag | 2040 |
| ttgggtcttg caggccaaag ccagagagat gaccgatggc tgctggtggc actcttggta | 2100 |
| ccaacgtgtg tcttcttggt ggtcctgctc gcattgggca ttgtgtactg cactcgctgt | 2160 |
| ggctcccata cgcccaacaa gcgtatcact gactgctatc gctgggtcac gcatgctggg | 2220 |
| aacaagagct caacagaacc catgcccccc agatggacag agaaggttct gttccttgaa | 2280 |
| cccagcattc atggcaaagg acacactgaa ggactccagg acctcaaggg gtgggtgctg | 2340 |
| ggatcttctc caataaatgg cgtgccaacc tcacccaaag tccgtgatcc ccgctga | 2397 |

<210> SEQ ID NO 6
<211> LENGTH: 798
<212> TYPE: PRT
<213> ORGANISM: Rattus rattus

<400> SEQUENCE: 6

Met Leu Leu Arg Leu Leu Ala Trp Ala Ala Val Pro Ala Leu
1               5                   10                  15

Gly Gln Ala Pro Trp Thr Pro Glu Pro Arg Ala Ala Cys Gly Pro Ser
            20                  25                  30

Ser Cys Tyr Ala Leu Phe Pro Arg Arg Thr Phe Leu Glu Ala Trp
        35                  40                  45

Arg Ser Cys Arg Glu Leu Gly Gly Asn Leu Ala Thr Pro Arg Thr Pro
50                  55                  60

Glu Glu Ala Arg Arg Val Asp Ser Leu Val Gly Val Pro Ala Asn
65                  70                  75                  80

Gly Leu Leu Trp Ile Gly Leu Gln Arg Gln Ala Arg Gln Cys Gln Pro
                85                  90                  95

Gln Arg Pro Leu Arg Gly Phe Ile Trp Thr Thr Gly Asp Gln Asp Thr
            100                 105                 110

Ala Phe Thr Asn Trp Ala Gln Pro Ala Thr Glu Gly Pro Cys Pro Ala
        115                 120                 125

Gln Arg Cys Ala Ala Leu Glu Ala Ser Gly Glu His Arg Trp Leu Glu
130                 135                 140

Gly Ser Cys Thr Leu Ala Val Asp Gly Tyr Leu Cys Gln Phe Gly Phe
145                 150                 155                 160

Glu Gly Ala Cys Pro Ala Leu Pro Leu Glu Val Gly Gln Ala Gly Pro
                165                 170                 175

Ala Ile Tyr Thr Thr Pro Phe Asn Leu Val Ser Ser Glu Phe Glu Trp
            180                 185                 190

Leu Pro Phe Gly Ser Val Ala Ala Val Gln Cys Gln Ala Gly Arg Gly
        195                 200                 205

Thr Ser Leu Leu Cys Val Lys Gln Pro Ser Gly Gly Val Gly Trp Ser
210                 215                 220

Gln Thr Gly Pro Leu Cys Pro Gly Thr Gly Cys Gly Pro Asp Asn Gly
225                 230                 235                 240

Gly Cys Glu His Glu Cys Val Glu Glu Leu Asp Gly Gly Met Ser Cys
                245                 250                 255

Arg Cys Ser Glu Gly Phe Arg Leu Ala Ala Asp Gly His Ser Cys Glu
            260                 265                 270

Asp Pro Cys Ala Gln Ala Pro Cys Glu Gln Gln Cys Glu Pro Gly Gly
        275                 280                 285

Pro Gln Gly Tyr Ser Cys His Cys Arg Leu Gly Phe Arg Pro Ala Glu
    290                 295                 300

Asp Glu Pro His Arg Cys Val Asp Thr Asp Glu Cys Gln Ile Ala Gly
305                 310                 315                 320

Val Cys Gln Gln Met Cys Val Asn Tyr Val Gly Gly Phe Glu Cys Tyr
                325                 330                 335

Cys Arg Glu Gly His Glu Leu Glu Ala Asp Gly Ile Ser Cys Ser Pro
            340                 345                 350

Ala Gly Ala Met Gly Ala Gln Ala Ser Gln Asp Leu Arg Asp Glu Leu
        355                 360                 365

Leu Asp Asp Gly Glu Glu Gly Glu Asp Glu Glu Glu Pro Trp Glu Asp
    370                 375                 380

-continued

```
Phe Asp Gly Thr Trp Thr Glu Glu Gln Gly Thr Leu Trp Met Ala Pro
385                 390                 395                 400

Thr His Pro Pro Asp Phe Gly Leu Pro Tyr Arg Pro Asn Phe Pro Gln
            405                 410                 415

Asp Gly Glu Pro Gln Arg Leu His Leu Glu Pro Thr Trp Pro Pro Pro
        420                 425                 430

Leu Ser Ala Pro Arg Gly Pro Tyr His Ser Val Val Ser Ala Thr
        435                 440                 445

Arg Pro Met Val Ile Ser Ala Thr Arg Pro Thr Gln Pro Ser Ala Arg
    450                 455                 460

Lys Thr Ser Val Ile Ser Ala Thr His Leu Leu Asn Pro Val His
465                 470                 475                 480

Pro Pro Ala Leu Ala Pro Thr Thr Pro Ala Val Leu Pro Glu His
                485                 490                 495

Gln Ile Pro Lys Ile Lys Ala Ser Tyr Pro Asp Leu Pro Phe Gly His
            500                 505                 510

Lys Pro Gly Ile Thr Ser Ala Thr His Pro Ala Gln Pro Pro His
        515                 520                 525

Gln Pro Pro Ile Ile Ser Thr Lys Tyr Pro Gln Val Phe Pro Pro Gln
530                 535                 540

Gln Ala Pro Met Ser Pro Asp Thr His Thr Ile Thr Asn Leu Pro Leu
545                 550                 555                 560

Ile Pro Ser His Leu Asp Pro Gly Asp Thr Thr Ser Gln Ala Gly His
                565                 570                 575

His Pro Leu Leu Pro Asp Val Pro Gly Ile Arg Thr Gln Ala Pro Gln
            580                 585                 590

Val Ser Val Ser Ala Leu Gln Pro Ser Leu Pro Thr Asn Ser Arg Ser
            595                 600                 605

Ser Val His Glu Pro Pro Val Pro Thr Ala Asn Gln Pro Pro Ala Phe
            610                 615                 620

Pro Ser Pro Leu Pro Pro Gln Ser Pro Ile Asn Gln Thr Ser Ser Ile
625                 630                 635                 640

Ser Pro Thr His Ser Tyr Ser Arg Ala Pro Gln Val Pro Arg Glu Gly
                645                 650                 655

Ala Pro Ser Pro Lys Ser Val Pro Arg Leu His Ser Val Ala Pro Thr
            660                 665                 670

Ala Ala Pro Thr Ala Leu Ala Glu Leu Gly Leu Ala Gly Gln Ser Gln
        675                 680                 685

Arg Asp Asp Arg Trp Leu Leu Val Ala Leu Leu Val Pro Thr Cys Val
    690                 695                 700

Phe Leu Val Val Leu Leu Ala Leu Gly Ile Val Tyr Cys Thr Arg Cys
705                 710                 715                 720

Gly Ser His Thr Pro Asn Lys Arg Ile Thr Asp Cys Tyr Arg Trp Val
                725                 730                 735

Thr His Ala Gly Asn Lys Ser Ser Thr Glu Pro Met Pro Pro Arg Trp
            740                 745                 750

Thr Glu Lys Val Leu Phe Leu Glu Pro Ser Ile His Gly Lys Gly His
        755                 760                 765

Thr Glu Gly Leu Gln Asp Leu Lys Gly Trp Val Leu Gly Ser Ser Pro
    770                 775                 780

Ile Asn Gly Val Pro Thr Ser Pro Lys Val Arg Asp Pro Arg
785                 790                 795
```

<210> SEQ ID NO 7
<211> LENGTH: 705
<212> TYPE: DNA
<213> ORGANISM: Artificial Sequence
<220> FEATURE:
<223> OTHER INFORMATION: Nucleic Acid Sequence encoding light chain of
      antibodies M4 and M4.1 with leader sequence

<400> SEQUENCE: 7

```
atgggatgga gctgtatcat cctcttcttg gtagcaacag ctacaggtgt ccactccgac      60
atccagatga cccagagccc aagcagcctg agcgccagcg tgggtgacag agtgaccatc     120
acctgtagag ccagccagaa tgtgggtact gctgtagcct ggctacagca gccccaggt     180
aaggctccaa agctgctgat ctactcggca tcgaatcggt acactggtgt gccaagcaga     240
ttcagcggta gcgtagcgg taccgactac accttcacca tcagcagcct ccagccagag     300
gacatcgcca cctactactg ccagcaatat accaactatc ccatgtacac gttcggccaa     360
gggaccaagg tgcaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg ataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttaa                     705
```

<210> SEQ ID NO 8
<211> LENGTH: 1422
<212> TYPE: DNA
<213> ORGANISM: Artificial Sequence
<220> FEATURE:
<223> OTHER INFORMATION: Nucleic Acid Sequence encoding heavy chain of
      antibody M4 with leader sequence

<400> SEQUENCE: 8

```
atgggatgga gctgtatcat cctcttcttg gtagcaacag ctacaggtgt ccactcccag      60
gtccaactgc aggagagcgg tccaggtctt gtgagaccta gccagaccct gagcctgacc     120
tgcaccgcgt ctggctacac cttcactgac tatgttatac actgggtgaa acagccacct     180
ggacgaggtc ttgagtggat tggatatatt aatccttatg atgatgatac tacctacaac     240
cagaagttca agggcagagt gacaatgctg gtagacacca gctccaacac agcctacctg     300
agactcagca gcgtgacagc cgaggacacc gcggtctatt attgtgcaag aaggggggaat     360
tcctatgatg gttactttga ctactctatg gactactggg gatccgggac cccggtcacc     420
gtctcctcag cctccaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
cagtcctcag gactctactc cctcagcagc gtggtgaccg tgccctccag cagcttgggc     660
acccagacct acatctgcaa cgtgaatcac aagcccagca acaccaaggt ggacaagaaa     720
gttgagccca aatcttgtga caaaactcac acatgcccac cgtgcccagc acctgaactc     780
ctggggggac cgtcagtctt cctcttcccc ccaaaaccca aggacaccct catgatctcc     840
cggacccctg aggtcacatg cgtggtggtg gacgtgagcc acgaagaccc tgaggtcaag     900
ttcaactggt acgtggacgg cgtggaggtg cataatgcca agacaaagcc gcgggaggag     960
cagtacaaca gcacgtaccg tgtggtcagc gtcctcaccg tcctgcacca ggactggctg    1020
```

```
aatggcaagg agtacaagtg caaggtctcc aacaaagccc tcccagcccc catcgagaaa    1080
accatctcca agccaaagg gcagccccga gaaccacagg tgtacaccct gcccccatcc    1140
cgggatgagc tgaccaagaa ccaggtcagc ctgacctgcc tggtcaaagg cttctatccc    1200
agcgacatcg ccgtggagtg ggagagcaat gggcagccgg agaacaacta caagaccacg    1260
cctcccgtgc tggactccga cggctccttc ttcctctaca gcaagctcac cgtggacaag    1320
agcaggtggc agcaggggaa cgtcttctca tgctccgtga tgcatgaggc tctgcacaac    1380
cactacacgc agaagagcct ctccctgtct cccgggaaat ga    1422
```

<210> SEQ ID NO 9
<211> LENGTH: 234
<212> TYPE: PRT
<213> ORGANISM: Artificial Sequence
<220> FEATURE:
<223> OTHER INFORMATION: Amino Acid Sequence of light chain of
      antibodies M4 and M4.1 with leader sequence

<400> SEQUENCE: 9

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
            20                  25                  30

Ser Val Gly Asp Arg Val Thr Ile Thr Cys Arg Ala Ser Gln Asn Val
        35                  40                  45

Gly Thr Ala Val Ala Trp Leu Gln Gln Thr Pro Gly Lys Ala Pro Lys
    50                  55                  60

Leu Leu Ile Tyr Ser Ala Ser Asn Arg Tyr Thr Gly Val Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Tyr Thr Asn
            100                 105                 110

Tyr Pro Met Tyr Thr Phe Gly Gln Gly Thr Lys Val Gln Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 10
<211> LENGTH: 648
<212> TYPE: DNA
<213> ORGANISM: Artificial Sequence
<220> FEATURE:
<223> OTHER INFORMATION: Nucleotide Sequence encoding light chain of
      antibodies M4 and M4.1 without leader sequence

<400> SEQUENCE: 10

```
gacatccaga tgacccagag cccaagcagc ctgagcgcca gcgtgggtga cagagtgacc        60
atcacctgta gagccagcca gaatgtgggt actgctgtag cctggctaca gcagacccca       120
ggtaaggctc caaagctgct gatctactcg gcatcgaatc ggtacactgg tgtgccaagc       180
agattcagcg gtagcggtag cggtaccgac tacaccttca ccatcagcag cctccagcca       240
gaggacatcg ccacctacta ctgccagcaa tataccaact atcccatgta cacgttcggc       300
caagggacca aggtgcaaat caaacgaact gtggctgcac catctgtctt catcttcccg       360
ccatctgatg agcagttgaa atctggaact gcctctgttg tgtgcctgct gaataacttc       420
tatcccagag aggccaaagt acagtggaag gtggataacg ccctccaatc gggtaactcc       480
caggagagtg tcacagagca ggacagcaag gacagcacct acagcctcag cagcaccctg       540
acgctgagca aagcagacta cgagaaacac aaagtctacg cctgcgaagt cacccatcag       600
ggcctgagct cgcccgtcac aaagagcttc aacaggggag agtgttaa                    648
```

<210> SEQ ID NO 11
<211> LENGTH: 215
<212> TYPE: PRT
<213> ORGANISM: Artificial Sequence
<220> FEATURE:
<223> OTHER INFORMATION: Amino Acid Sequence of light chain of
      antibodies M4 and M4.1 without leader sequence

<400> SEQUENCE: 11

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asn Val Gly Thr Ala
            20                  25                  30

Val Ala Trp Leu Gln Gln Thr Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Thr Asn Tyr Pro Met
                85                  90                  95

Tyr Thr Phe Gly Gln Gly Thr Lys Val Gln Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 12
<211> LENGTH: 33
<212> TYPE: DNA
<213> ORGANISM: Artificial Sequence
<220> FEATURE:
<223> OTHER INFORMATION: Nucleic Acid Sequence encoding CDR1 of light
      chain of antibodies M4 and M4.1

<400> SEQUENCE: 12
agagccagcc agaatgtggg tactgctgta gcc                                   33

<210> SEQ ID NO 13
<211> LENGTH: 11
<212> TYPE: PRT
<213> ORGANISM: Artificial Sequence
<220> FEATURE:
<223> OTHER INFORMATION: Amino Acid Sequence of CDR1 of light chain of
      antibodies M4 and M4.1

<400> SEQUENCE: 13

Arg Ala Ser Gln Asn Val Gly Thr Ala Val Ala
1               5                   10

<210> SEQ ID NO 14
<211> LENGTH: 21
<212> TYPE: DNA
<213> ORGANISM: Artificial Sequence
<220> FEATURE:
<223> OTHER INFORMATION: Nucleotide Sequence encoding CDR2 of light
      chain of antibodies M4 and M4.1

<400> SEQUENCE: 14
tcggcatcga atcggtacac t                                                21

<210> SEQ ID NO 15
<211> LENGTH: 7
<212> TYPE: PRT
<213> ORGANISM: Artificial Sequence
<220> FEATURE:
<223> OTHER INFORMATION: Amino Acid Sequence of CDR2 of light chain of
      antibodies M4 and M4.1

<400> SEQUENCE: 15

Ser Ala Ser Asn Arg Tyr Thr
1               5

<210> SEQ ID NO 16
<211> LENGTH: 30
<212> TYPE: DNA
<213> ORGANISM: Artificial Sequence
<220> FEATURE:
<223> OTHER INFORMATION: Nucleotide Sequence encoding CDR3 of light
      chain of antibodies M4 and M4.1

<400> SEQUENCE: 16
cagcaatata ccaactatcc catgtacacg                                       30

<210> SEQ ID NO 17
<211> LENGTH: 10
<212> TYPE: PRT
<213> ORGANISM: Artificial Sequence
<220> FEATURE:
<223> OTHER INFORMATION: Amino Acid Sequence of CDR3 of light chain of
      antibodies M4 and M4.1

<400> SEQUENCE: 17

Gln Gln Tyr Thr Asn Tyr Pro Met Tyr Thr
1               5                   10

<210> SEQ ID NO 18
<211> LENGTH: 294
<212> TYPE: DNA
<213> ORGANISM: Artificial Sequence
<220> FEATURE:
<223> OTHER INFORMATION: Nucleotide Sequence encoding variable domain of
      light chain of antibodies M4 and M4.1

<400> SEQUENCE: 18

```
gacatccaga tgacccagag cccaagcagc ctgagcgcca gcgtgggtga cagagtgacc        60
atcacctgta gagccagcca gaatgtgggt actgctgtag cctggctaca gcagacccca       120
ggtaaggctc caaagctgct gatctactcg gcatcgaatc ggtacactgg tgtgccaagc       180
agattcagcg gtagcggtag cggtaccgac tacaccttca ccatcagcag cctccagcca       240
gaggacatcg ccacctacta ctgccagcaa tataccaact atcccatgta cacg             294
```

<210> SEQ ID NO 19
<211> LENGTH: 98
<212> TYPE: PRT
<213> ORGANISM: Artificial Sequence
<220> FEATURE:
<223> OTHER INFORMATION: Amino Acid Sequence of variable domain of light
      chain of antibodies M4 and M4.1

<400> SEQUENCE: 19

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asn Val Gly Thr Ala
            20                  25                  30

Val Ala Trp Leu Gln Gln Thr Pro Gly Lys Ala Pro Lys Leu Leu Ile
        35                  40                  45

Tyr Ser Ala Ser Asn Arg Tyr Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Thr Asn Tyr Pro Met
                85                  90                  95

Tyr Thr
```

<210> SEQ ID NO 20
<211> LENGTH: 473
<212> TYPE: PRT
<213> ORGANISM: Artificial Sequence
<220> FEATURE:
<223> OTHER INFORMATION: Amino Acid Sequence of heavy chain of antibody
      M4 plus leader sequence

<400> SEQUENCE: 20

```
Met Gly Trp Ser Cys Ile Ile Leu Phe Leu Val Ala Thr Ala Thr Gly
1               5                  10                  15

Val His Ser Gln Val Gln Leu Gln Glu Ser Gly Pro Gly Leu Val Arg
            20                  25                  30

Pro Ser Gln Thr Leu Ser Leu Thr Cys Thr Ala Ser Gly Tyr Thr Phe
        35                  40                  45

Thr Asp Tyr Val Ile His Trp Val Lys Gln Pro Pro Gly Arg Gly Leu
    50                  55                  60

Glu Trp Ile Gly Tyr Ile Asn Pro Tyr Asp Asp Thr Thr Tyr Asn
65                  70                  75                  80
```

Gln Lys Phe Lys Gly Arg Val Thr Met Leu Val Asp Thr Ser Ser Asn
                85                  90                  95

Thr Ala Tyr Leu Arg Leu Ser Ser Val Thr Ala Glu Asp Thr Ala Val
            100                 105                 110

Tyr Tyr Cys Ala Arg Arg Gly Asn Ser Tyr Asp Gly Tyr Phe Asp Tyr
        115                 120                 125

Ser Met Asp Tyr Trp Gly Ser Gly Thr Pro Val Thr Val Ser Ser Ala
130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
450                 455                 460

Lys Ser Leu Ser Leu Ser Pro Gly Lys
465                 470

<210> SEQ ID NO 21
<211> LENGTH: 1365
<212> TYPE: DNA

<213> ORGANISM: Artificial Sequence
<220> FEATURE:
<223> OTHER INFORMATION: Nucleotide Sequence encoding heavy chain of
     antibody M4 without leader sequence

<400> SEQUENCE: 21

```
caggtccaac tgcaggagag cggtccaggt cttgtgagac ctagccagac cctgagcctg      60
acctgcaccg cgtctggcta caccttcact gactatgtta tacactgggt gaaacagcca     120
cctggacgag gtcttgagtg gattggatat attaatcctt atgatgatga tactacctac     180
aaccagaagt tcaagggcag agtgacaatg ctggtagaca ccagctccaa cacagcctac     240
ctgagactca gcagcgtgac agccgaggac accgcggtct attattgtgc aagaaggggg     300
aattcctatg atggttactt tgactactct atggactact ggggatccgg accccggtc      360 accgtctcct cagcctccac caagggccca tcggtcttcc cctggcacc ctcctccaag      420 agcacctctg ggggcacagc ggccctgggc tgcctggtca aggactactt ccccgaaccg     480
gtgacggtgt cgtggaactc aggcgccctg accagcggcg tgcacacctt cccggctgtc     540
ctacagtcct caggactcta ctccctcagc agcgtggtga ccgtgccctc agcagcttg      600 ggcacccaga cctacatctg caacgtgaat cacaagccca gcaacaccaa ggtggacaag     660
aaagttgagc ccaaatcttg tgacaaaact cacacatgcc caccgtgccc agcacctgaa     720
ctcctggggg gaccgtcagt cttcctcttc cccccaaaac ccaaggacac cctcatgatc     780
tcccggaccc ctgaggtcac atgcgtggtg gtggacgtga gccacgaaga ccctgaggtc     840
aagttcaact ggtacgtgga cggcgtggag gtgcataatg ccaagacaaa gccgcgggag     900
gagcagtaca acagcacgta ccgtgtggtc agcgtcctca ccgtcctgca ccaggactgg     960
ctgaatggca aggagtacaa gtgcaaggtc tccaacaaag ccctcccagc ccccatcgag    1020
aaaaccatct ccaaagccaa agggcagccc cgagaaccac aggtgtacac cctgccccca    1080
tcccgggatg agctgaccaa gaaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct acagcaagct caccgtggac    1260
aagagcaggt ggcagcaggg gaacgtcttc tcatgctccg tgatgcatga ggctctgcac    1320
aaccactaca cgcagaagag cctctccctg tctcccggga atga                     1365
```

<210> SEQ ID NO 22
<211> LENGTH: 454
<212> TYPE: PRT
<213> ORGANISM: Artificial Sequence
<220> FEATURE:
<223> OTHER INFORMATION: Amino Acid Sequence of heavy chain of antibody
     M4 without leader sequence

<400> SEQUENCE: 22

```
Gln Val Gln Leu Gln Glu Ser Gly Pro Gly Leu Val Arg Pro Ser Gln
1               5                   10                  15

Thr Leu Ser Leu Thr Cys Thr Ala Ser Gly Tyr Thr Phe Thr Asp Tyr
            20                  25                  30

Val Ile His Trp Val Lys Gln Pro Pro Gly Arg Gly Leu Glu Trp Ile
        35                  40                  45

Gly Tyr Ile Asn Pro Tyr Asp Asp Asp Thr Thr Tyr Asn Gln Lys Phe
    50                  55                  60

Lys Gly Arg Val Thr Met Leu Val Asp Thr Ser Ser Asn Thr Ala Tyr
65                  70                  75                  80
```

```
Leu Arg Leu Ser Ser Val Thr Ala Glu Asp Thr Ala Val Tyr Tyr Cys
            85                  90                  95

Ala Arg Arg Gly Asn Ser Tyr Asp Gly Tyr Phe Asp Tyr Ser Met Asp
        100                 105                 110

Tyr Trp Gly Ser Gly Thr Pro Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 23
<211> LENGTH: 1422
<212> TYPE: DNA
<213> ORGANISM: Artificial Sequence
<220> FEATURE:
<223> OTHER INFORMATION: Nucleotide Sequence encoding heavy chain of
``` antibody M4.1 with leader sequence

<400> SEQUENCE: 23

```
atgggatgga gctgtatcat cctcttcttg gtagcaacag ctacaggtgt ccactcccag      60
gtccaactgc aggagagcgg tccaggtctt gtgagaccta gccagaccct gagcctgacc     120
tgcaccgcgt ctggctacac cttcactgac tatgttatac actgggtgaa acagccacct    180
ggacgaggtc ttgagtggat tggatatatt aatccttatg atgatgatac tacctacaac    240
cagaagttca agggcagagt gacaatgctg gtagacacca gctccaacac agcctacctg    300
agactcagca gcgtgacagc cgaggacacc gcggtctatt attgtgcaag aagggggaat    360
tcctatgatg gttactttga ctactctatg gactactggg gatccgggac cccggtcacc    420
gtctcctcag cctccaccaa gggcccatcg gtcttccccc tggcaccctc ctccaagagc    480
acctctgggg gcacagcggc cctgggctgc ctggtcaagg actacttccc cgaaccggtg    540
acggtgtcgt ggaactcagg cgccctgacc agcggcgtgc acaccttccc ggctgtccta    600
cagtcctcag gactctactc cctcagcagc gtggtgaccg tgccctccag cagcttgggc    660
acccagacct acatctgcaa cgtgaatcac aagcccagca acaccaaggt ggacaagaaa    720
gttgagccca aatcttgtga caaaactcac acatgcccac cgtgcccagc acctgaactc    780
ctggggggac cgtcagtctt cctcttcccc ccaaaaccca aggacaccct catgatctcc    840
cggacccctg aggtcacatg cgtggtggtg gacgtgagcc acgaagaccc tgaggtcaag    900
ttcaactggt acgtggacgg cgtggaggtg cataatgcca agacaaagcc gcgggaggag    960
cagtacaaca gcacgtaccg tgtggtcagc gtcctcaccg tcctgcacca ggactggctg   1020
aatggcaagg agtacaagtg caaggtctcc aacaaagccc tcccagcccc catcgagaaa   1080
accatctcca aagccaaagg gcagccccga gaaccacagg tgtacaccct gcccccatcc   1140
cgggatgagc tgaccaagaa ccaggtcagc ctgacctgcc tggtcaaagg cttctatccc   1200
agcgacatcg ccgtggagtg ggagagcaat gggcagccgg agaacaacta caagaccacg   1260
cctcccgtgc tggactccga cggcttcttc ttcctctaca gcaagctcac cgtggacaag   1320
agcaggtggc agcaggggaa cgtcttctca tgctccgtga tgcatgaggc tctgcacaac   1380
cactacacgc agaagagcct ctccctgtct ccgggaaat  ga                      1422
```

<210> SEQ ID NO 24
<211> LENGTH: 473
<212> TYPE: PRT
<213> ORGANISM: Artificial Sequence
<220> FEATURE:
<223> OTHER INFORMATION: Amino Acid Sequence of heavy chain of antibody M4.1 with leader sequence

<400> SEQUENCE: 24

```
Met Gly Trp Ser Cys Ile Ile Leu Phe Leu Val Ala Thr Ala Thr Gly
1               5                   10                  15

Val His Ser Gln Val Gln Leu Gln Glu Ser Gly Pro Gly Leu Val Arg
            20                  25                  30

Pro Ser Gln Thr Leu Ser Leu Thr Cys Thr Ala Ser Gly Tyr Thr Phe
        35                  40                  45

Thr Asp Tyr Val Ile His Trp Val Lys Gln Pro Pro Gly Arg Gly Leu
    50                  55                  60

Glu Trp Ile Gly Tyr Ile Asn Pro Tyr Asp Asp Asp Thr Thr Tyr Asn
65                  70                  75                  80

Gln Lys Phe Lys Gly Arg Val Thr Met Leu Val Asp Thr Ser Ser Asn
```

```
                        85                  90                  95
Thr Ala Tyr Leu Arg Leu Ser Ser Val Thr Ala Glu Asp Thr Ala Val
            100                 105                 110
Tyr Tyr Cys Ala Arg Arg Gly Asn Ser Tyr Asp Gly Tyr Phe Asp Tyr
            115                 120                 125
Ser Met Asp Tyr Trp Gly Ser Gly Thr Pro Val Thr Val Ser Ser Ala
            130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
            195                 200                 205
Ser Ser Val Val Thr Val Pro Ser Ser Ser Leu Gly Thr Gln Thr Tyr
            210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
            275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
            355                 360                 365
Pro Arg Glu Pro Gln Val Tyr Thr Leu Pro Pro Ser Arg Asp Glu Leu
            370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Phe Phe Leu
            420                 425                 430
Tyr Ser Lys Leu Thr Val Asp Lys Ser Arg Trp Gln Gln Gly Asn Val
            435                 440                 445
Phe Ser Cys Ser Val Met His Glu Ala Leu His Asn His Tyr Thr Gln
            450                 455                 460
Lys Ser Leu Ser Leu Ser Pro Gly Lys
465                 470

<210> SEQ ID NO 25
<211> LENGTH: 1365
<212> TYPE: DNA
<213> ORGANISM: Artificial Sequence
```

<220> FEATURE:
<223> OTHER INFORMATION: Nucleotide Sequence encoding heavy chain of
       antibody M4.1 without leader sequence

<400> SEQUENCE: 25

```
caggtccaac tgcaggagag cggtccaggt cttgtgagac ctagccagac cctgagcctg        60
acctgcaccg cgtctggcta caccttcact gactatgtta tacactgggt gaaacagcca       120
cctggacgag gtcttgagtg gattggatat attaatcctt atgatgatga tactacctac       180
aaccagaagt tcaagggcag agtgacaatg ctggtagaca ccagctccaa cacagcctac       240
ctgagactca gcagcgtgac agccgaggac accgcggtct attattgtgc aagaaggggg       300
aattcctatg atggttactt tgactactct atggactact ggggatccgg accccggtc        360
accgtctcct cagcctccac caagggccca tcggtcttcc cctggcacc ctcctccaag        420
agcacctctg ggggcacagc ggccctgggc tgcctggtca aggactactt ccccgaaccg       480
gtgacggtgt cgtggaactc aggcgccctg accagcggcg tgcacacctt cccggctgtc       540
ctacagtcct caggactcta ctccctcagc agcgtggtga ccgtgcctc cagcagcttg        600
ggcacccaga cctacatctg caacgtgaat cacaagccca gcaacaccaa ggtggacaag       660
aaagttgagc ccaaatcttg tgacaaaact cacacatgcc caccgtgccc agcacctgaa       720
ctcctggggg gaccgtcagt cttcctcttc cccccaaaac ccaaggacac cctcatgatc       780
tcccggaccc ctgaggtcac atgcgtggtg gtggacgtga gccacgaaga ccctgaggtc       840
aagttcaact ggtacgtgga cggcgtggag gtgcataatg ccaagacaaa gccgcgggag       900
gagcagtaca acagcacgta ccgtgtggtc agcgtcctca ccgtcctgca ccaggactgg       960
ctgaatggca aggagtacaa gtgcaaggtc tccaacaaag ccctcccagc ccccatcgag      1020
aaaaccatct ccaaagccaa agggcagccc cgagaaccac aggtgtacac cctgccccca      1080
tcccgggatg agctgaccaa gaaccaggtc agcctgacct gcctggtcaa aggcttctat      1140
cccagcgaca tcgccgtgga gtgggagagc aatgggcagc cggagaacaa ctacaagacc      1200
acgcctcccg tgctggactc cgacggcttc ttcttcctct acagcaagct caccgtggac      1260
aagagcaggt ggcagcaggg gaacgtcttc tcatgctccg tgatgcatga ggctctgcac      1320
aaccactaca cgcagaagag cctctccctg tctcccggga aatga                      1365
```

<210> SEQ ID NO 26
<211> LENGTH: 454
<212> TYPE: PRT
<213> ORGANISM: Artificial Sequence
<220> FEATURE:
<223> OTHER INFORMATION: Amino Acid Sequence of heavy chain of antibody
       M4.1 without leader sequence

<400> SEQUENCE: 26

```
Gln Val Gln Leu Gln Glu Ser Gly Pro Gly Leu Val Arg Pro Ser Gln
1               5                   10                  15

Thr Leu Ser Leu Thr Cys Thr Ala Ser Gly Tyr Thr Phe Thr Asp Tyr
            20                  25                  30

Val Ile His Trp Val Lys Gln Pro Pro Gly Arg Gly Leu Glu Trp Ile
        35                  40                  45

Gly Tyr Ile Asn Pro Tyr Asp Asp Asp Thr Thr Tyr Asn Gln Lys Phe
    50                  55                  60

Lys Gly Arg Val Thr Met Leu Val Asp Thr Ser Ser Asn Thr Ala Tyr
65                  70                  75                  80

Leu Arg Leu Ser Ser Val Thr Ala Glu Asp Thr Ala Val Tyr Tyr Cys
```

```
                85                  90                  95
Ala Arg Arg Gly Asn Ser Tyr Asp Gly Tyr Phe Asp Tyr Ser Met Asp
                        100                 105                 110

Tyr Trp Gly Ser Gly Thr Pro Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 27
<211> LENGTH: 30
<212> TYPE: DNA
<213> ORGANISM: Artificial Sequence
<220> FEATURE:
<223> OTHER INFORMATION: Nucleotide Sequence encoding CDR1 of heavy
      chain of antibodies M4 and M4.1
```

```
<400> SEQUENCE: 27
ggctacacct tcactgacta tgttatacac                                              30

<210> SEQ ID NO 28
<211> LENGTH: 10
<212> TYPE: PRT
<213> ORGANISM: Artificial Sequence
<220> FEATURE:
<223> OTHER INFORMATION: Amino Acid Sequence of CDR1 of heavy chain of
      antibodies M4 and M4.1

<400> SEQUENCE: 28

Gly Tyr Thr Phe Thr Asp Tyr Val Ile His
1               5                   10

<210> SEQ ID NO 29
<211> LENGTH: 51
<212> TYPE: DNA
<213> ORGANISM: Artificial Sequence
<220> FEATURE:
<223> OTHER INFORMATION: Nucleotide Sequence encoding CDR2 of heavy
      chain of antibodies M4 and M4.1

<400> SEQUENCE: 29
tatattaatc cttatgatga tgatactacc tacaaccaga agttcaaggg c              51

<210> SEQ ID NO 30
<211> LENGTH: 17
<212> TYPE: PRT
<213> ORGANISM: Artificial Sequence
<220> FEATURE:
<223> OTHER INFORMATION: Amino Acid Sequence of CDR2 of heavy chain of
      antibodies M4 and M4.1

<400> SEQUENCE: 30

Tyr Ile Asn Pro Tyr Asp Asp Asp Thr Thr Tyr Asn Gln Lys Phe Lys
1               5                   10                  15

Gly

<210> SEQ ID NO 31
<211> LENGTH: 51
<212> TYPE: DNA
<213> ORGANISM: Artificial Sequence
<220> FEATURE:
<223> OTHER INFORMATION: Nucleotide Sequence encoding CDR3 of heavy
      chain of Antibodies M4 and M4.1

<400> SEQUENCE: 31
gcaagaaggg ggaattccta tgatggttac tttgactact ctatggacta c             51

<210> SEQ ID NO 32
<211> LENGTH: 17
<212> TYPE: PRT
<213> ORGANISM: Artificial Sequence
<220> FEATURE:
<223> OTHER INFORMATION: Amino Acid Sequence of heavy chain CDR3 of
      antibodies M4 and M4.1

<400> SEQUENCE: 32

Ala Arg Arg Gly Asn Ser Tyr Asp Gly Tyr Phe Asp Tyr Ser Met Asp
1               5                   10                  15

Tyr

<210> SEQ ID NO 33
```

<211> LENGTH: 339
<212> TYPE: DNA
<213> ORGANISM: Artificial Sequence
<220> FEATURE:
<223> OTHER INFORMATION: Nucleotide Sequence encoding variable domain of
      heavy chain of antibodies M4 and M4.1

<400> SEQUENCE: 33
caggtccaac tgcaggagag cggtccaggt cttgtgagac ctagccagac cctgagcctg        60
acctgcaccg cgtctggcta caccttcact gactatgtta tacactgggt gaaacagcca       120
cctggacgag gtcttgagtg gattggatat attaatcctt atgatgatga tactacctac       180
aaccagaagt tcaagggcag agtgacaatg ctggtagaca ccagctccaa cacagcctac       240
ctgagactca gcagcgtgac agccgaggac accgcggtct attattgtgc aagaaggggg       300
aattcctatg atggttactt tgactactct atggactac                              339

<210> SEQ ID NO 34
<211> LENGTH: 113
<212> TYPE: PRT
<213> ORGANISM: Artificial Sequence
<220> FEATURE:
<223> OTHER INFORMATION: Amino Acid Sequence of variable domain of heavy
      chain of antibodies M4 and M4.1

<400> SEQUENCE: 34

Gln Val Gln Leu Gln Glu Ser Gly Pro Gly Leu Val Arg Pro Ser Gln
1               5                   10                  15

Thr Leu Ser Leu Thr Cys Thr Ala Ser Gly Tyr Thr Phe Thr Asp Tyr
            20                  25                  30

Val Ile His Trp Val Lys Gln Pro Pro Gly Arg Gly Leu Glu Trp Ile
        35                  40                  45

Gly Tyr Ile Asn Pro Tyr Asp Asp Asp Thr Thr Tyr Asn Gln Lys Phe
    50                  55                  60

Lys Gly Arg Val Thr Met Leu Val Asp Thr Ser Ser Asn Thr Ala Tyr
65                  70                  75                  80

Leu Arg Leu Ser Ser Val Thr Ala Glu Asp Thr Ala Val Tyr Tyr Cys
                85                  90                  95

Ala Arg Arg Gly Asn Ser Tyr Asp Gly Tyr Phe Asp Tyr Ser Met Asp
            100                 105                 110

Tyr

<210> SEQ ID NO 35
<211> LENGTH: 2477
<212> TYPE: PRT
<213> ORGANISM: Homo sapiens

<400> SEQUENCE: 35

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr

```
            85                  90                  95
Cys Phe Asp Lys Tyr Thr Gly Asn Thr Tyr Arg Val Gly Asp Thr Tyr
            100                 105                 110
Glu Arg Pro Lys Asp Ser Met Ile Trp Asp Cys Thr Cys Ile Gly Ala
            115                 120                 125
Gly Arg Gly Arg Ile Ser Cys Thr Ile Ala Asn Arg Cys His Glu Gly
            130                 135                 140
Gly Gln Ser Tyr Lys Ile Gly Asp Thr Trp Arg Arg Pro His Glu Thr
145                 150                 155                 160
Gly Gly Tyr Met Leu Glu Cys Val Cys Leu Gly Asn Gly Lys Gly Glu
                165                 170                 175
Trp Thr Cys Lys Pro Ile Ala Glu Lys Cys Phe Asp His Ala Ala Gly
                180                 185                 190
Thr Ser Tyr Val Val Gly Glu Thr Trp Glu Lys Pro Tyr Gln Gly Trp
            195                 200                 205
Met Met Val Asp Cys Thr Cys Leu Gly Glu Gly Ser Gly Arg Ile Thr
        210                 215                 220
Cys Thr Ser Arg Asn Arg Cys Asn Asp Gln Asp Thr Arg Thr Ser Tyr
225                 230                 235                 240
Arg Ile Gly Asp Thr Trp Ser Lys Lys Asp Asn Arg Gly Asn Leu Leu
                245                 250                 255
Gln Cys Ile Cys Thr Gly Asn Gly Arg Gly Glu Trp Lys Cys Glu Arg
                260                 265                 270
His Thr Ser Val Gln Thr Thr Ser Ser Gly Ser Gly Pro Phe Thr Asp
            275                 280                 285
Val Arg Ala Ala Val Tyr Gln Pro Gln Pro His Pro Gln Pro Pro Pro
        290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                325                 330                 335
Gly Asn Gly Val Ser Cys Gln Glu Thr Ala Val Thr Gln Thr Tyr Gly
            340                 345                 350
Gly Asn Ser Asn Gly Glu Pro Cys Val Leu Pro Phe Thr Tyr Asn Gly
            355                 360                 365
Arg Thr Phe Tyr Ser Cys Thr Thr Glu Gly Arg Gln Asp Gly His Leu
        370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                405                 410                 415
Gly Ala Leu Cys His Phe Pro Phe Leu Tyr Asn Asn His Asn Tyr Thr
            420                 425                 430
Asp Cys Thr Ser Glu Gly Arg Arg Asp Asn Met Lys Trp Cys Gly Thr
            435                 440                 445
Thr Gln Asn Tyr Asp Ala Asp Gln Lys Phe Gly Phe Cys Pro Met Ala
        450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                485                 490                 495
Thr Cys Val Gly Asn Gly Arg Gly Glu Trp Thr Cys Ile Ala Tyr Ser
            500                 505                 510
```

```
Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925
```

```
Pro  Pro  Glu  Ser  Ala  Val  Thr  Gly  Tyr  Arg  Val  Asp  Val  Ile  Pro  Val
     930                 935                 940

Asn  Leu  Pro  Gly  Glu  His  Gly  Gln  Arg  Leu  Pro  Ile  Ser  Arg  Asn  Thr
945                      950                 955                      960

Phe  Ala  Glu  Val  Thr  Gly  Leu  Ser  Pro  Gly  Val  Thr  Tyr  Tyr  Phe  Lys
                    965                      970                 975

Val  Phe  Ala  Val  Ser  His  Gly  Arg  Glu  Ser  Lys  Pro  Leu  Thr  Ala  Gln
               980                      985                      990

Gln  Thr  Thr  Lys  Leu  Asp  Ala  Pro  Thr  Asn  Leu  Gln  Phe  Val  Asn  Glu
          995                      1000                     1005

Thr  Asp  Ser  Thr  Val  Leu  Val  Arg  Trp  Thr  Pro  Pro  Arg  Ala  Gln
     1010                 1015                1020

Ile  Thr  Gly  Tyr  Arg  Leu  Thr  Val  Gly  Leu  Thr  Arg  Arg  Gly  Gln
     1025                 1030                1035

Pro  Arg  Gln  Tyr  Asn  Val  Gly  Pro  Ser  Val  Ser  Lys  Tyr  Pro  Leu
     1040                 1045                1050

Arg  Asn  Leu  Gln  Pro  Ala  Ser  Glu  Tyr  Thr  Val  Ser  Leu  Val  Ala
     1055                 1060                1065

Ile  Lys  Gly  Asn  Gln  Glu  Ser  Pro  Lys  Ala  Thr  Gly  Val  Phe  Thr
     1070                 1075                1080

Thr  Leu  Gln  Pro  Gly  Ser  Ser  Ile  Pro  Pro  Tyr  Asn  Thr  Glu  Val
     1085                 1090                1095

Thr  Glu  Thr  Thr  Ile  Val  Ile  Thr  Trp  Thr  Pro  Ala  Pro  Arg  Ile
     1100                 1105                1110

Gly  Phe  Lys  Leu  Gly  Val  Arg  Pro  Ser  Gln  Gly  Gly  Glu  Ala  Pro
     1115                 1120                1125

Arg  Glu  Val  Thr  Ser  Asp  Ser  Gly  Ser  Ile  Val  Val  Ser  Gly  Leu
     1130                 1135                1140

Thr  Pro  Gly  Val  Glu  Tyr  Val  Tyr  Thr  Ile  Gln  Val  Leu  Arg  Asp
     1145                 1150                1155

Gly  Gln  Glu  Arg  Asp  Ala  Pro  Ile  Val  Asn  Lys  Val  Val  Thr  Pro
     1160                 1165                1170

Leu  Ser  Pro  Pro  Thr  Asn  Leu  His  Leu  Glu  Ala  Asn  Pro  Asp  Thr
     1175                 1180                1185

Gly  Val  Leu  Thr  Val  Ser  Trp  Glu  Arg  Ser  Thr  Thr  Pro  Asp  Ile
     1190                 1195                1200

Thr  Gly  Tyr  Arg  Ile  Thr  Thr  Thr  Pro  Thr  Asn  Gly  Gln  Gln  Gly
     1205                 1210                1215

Asn  Ser  Leu  Glu  Glu  Val  Val  His  Ala  Asp  Gln  Ser  Ser  Cys  Thr
     1220                 1225                1230

Phe  Asp  Asn  Leu  Ser  Pro  Gly  Leu  Glu  Tyr  Asn  Val  Ser  Val  Tyr
     1235                 1240                1245

Thr  Val  Lys  Asp  Asp  Lys  Glu  Ser  Val  Pro  Ile  Ser  Asp  Thr  Ile
     1250                 1255                1260

Ile  Pro  Glu  Val  Pro  Gln  Leu  Thr  Asp  Leu  Ser  Phe  Val  Asp  Ile
     1265                 1270                1275

Thr  Asp  Ser  Ser  Ile  Gly  Leu  Arg  Trp  Thr  Pro  Leu  Asn  Ser  Ser
     1280                 1285                1290

Thr  Ile  Ile  Gly  Tyr  Arg  Ile  Thr  Val  Val  Ala  Ala  Gly  Glu  Gly
     1295                 1300                1305

Ile  Pro  Ile  Phe  Glu  Asp  Phe  Val  Asp  Ser  Ser  Val  Gly  Tyr  Tyr
     1310                 1315                1320

Thr  Val  Thr  Gly  Leu  Glu  Pro  Gly  Ile  Asp  Tyr  Asp  Ile  Ser  Val
```

```
            1325                1330                1335
Ile Thr Leu Ile Asn Gly Gly Glu Ser Ala Pro Thr Thr Leu Thr
            1340                1345                1350
Gln Gln Thr Ala Val Pro Pro Thr Asp Leu Arg Phe Thr Asn
    1355                1360                1365
Ile Gly Pro Asp Thr Met Arg Val Thr Trp Ala Pro Pro Ser
    1370                1375                1380
Ile Asp Leu Thr Asn Phe Leu Val Arg Tyr Ser Pro Val Lys Asn
    1385                1390                1395
Glu Glu Asp Val Ala Glu Leu Ser Ile Ser Pro Ser Asp Asn Ala
    1400                1405                1410
Val Val Leu Thr Asn Leu Leu Pro Gly Thr Glu Tyr Val Val Ser
    1415                1420                1425
Val Ser Ser Val Tyr Glu Gln His Glu Ser Thr Pro Leu Arg Gly
    1430                1435                1440
Arg Gln Lys Thr Gly Leu Asp Ser Pro Thr Gly Ile Asp Phe Ser
    1445                1450                1455
Asp Ile Thr Ala Asn Ser Phe Thr Val His Trp Ile Ala Pro Arg
    1460                1465                1470
Ala Thr Ile Thr Gly Tyr Arg Ile Arg His His Pro Glu His Phe
    1475                1480                1485
Ser Gly Arg Pro Arg Glu Asp Arg Val Pro His Ser Arg Asn Ser
    1490                1495                1500
Ile Thr Leu Thr Asn Leu Thr Pro Gly Thr Glu Tyr Val Val Ser
    1505                1510                1515
Ile Val Ala Leu Asn Gly Arg Glu Glu Ser Pro Leu Leu Ile Gly
    1520                1525                1530
Gln Gln Ser Thr Val Ser Asp Val Pro Arg Asp Leu Glu Val Val
    1535                1540                1545
Ala Ala Thr Pro Thr Ser Leu Leu Ile Ser Trp Asp Ala Pro Ala
    1550                1555                1560
Val Thr Val Arg Tyr Tyr Arg Ile Thr Tyr Gly Glu Thr Gly Gly
    1565                1570                1575
Asn Ser Pro Val Gln Glu Phe Thr Val Pro Gly Ser Lys Ser Thr
    1580                1585                1590
Ala Thr Ile Ser Gly Leu Lys Pro Gly Val Asp Tyr Thr Ile Thr
    1595                1600                1605
Val Tyr Ala Val Thr Gly Arg Gly Asp Ser Pro Ala Ser Ser Lys
    1610                1615                1620
Pro Ile Ser Ile Asn Tyr Arg Thr Glu Ile Asp Lys Pro Ser Gln
    1625                1630                1635
Met Gln Val Thr Asp Val Gln Asp Asn Ser Ile Ser Val Lys Trp
    1640                1645                1650
Leu Pro Ser Ser Ser Pro Val Thr Gly Tyr Arg Val Thr Thr Thr
    1655                1660                1665
Pro Lys Asn Gly Pro Gly Pro Thr Lys Thr Lys Thr Ala Gly Pro
    1670                1675                1680
Asp Gln Thr Glu Met Thr Ile Glu Gly Leu Gln Pro Thr Val Glu
    1685                1690                1695
Tyr Val Val Ser Val Tyr Ala Gln Asn Pro Ser Gly Glu Ser Gln
    1700                1705                1710
Pro Leu Val Gln Thr Ala Val Thr Asn Ile Asp Arg Pro Lys Gly
    1715                1720                1725
```

-continued

```
Leu Ala Phe Thr Asp Val Asp Val Asp Ser Ile Lys Ile Ala Trp
    1730            1735                1740

Glu Ser Pro Gln Gly Gln Val Ser Arg Tyr Arg Val Thr Tyr Ser
    1745            1750                1755

Ser Pro Glu Asp Gly Ile His Glu Leu Phe Pro Ala Pro Asp Gly
    1760            1765                1770

Glu Glu Asp Thr Ala Glu Leu Gln Gly Leu Arg Pro Gly Ser Glu
    1775            1780                1785

Tyr Thr Val Ser Val Val Ala Leu His Asp Asp Met Glu Ser Gln
    1790            1795                1800

Pro Leu Ile Gly Thr Gln Ser Thr Ala Ile Pro Ala Pro Thr Asp
    1805            1810                1815

Leu Lys Phe Thr Gln Val Thr Pro Thr Ser Leu Ser Ala Gln Trp
    1820            1825                1830

Thr Pro Pro Asn Val Gln Leu Thr Gly Tyr Arg Val Arg Val Thr
    1835            1840                1845

Pro Lys Glu Lys Thr Gly Pro Met Lys Glu Ile Asn Leu Ala Pro
    1850            1855                1860

Asp Ser Ser Val Val Val Ser Gly Leu Met Val Ala Thr Lys
    1865            1870                1875

Tyr Glu Val Ser Val Tyr Ala Leu Lys Asp Thr Leu Thr Ser Arg
    1880            1885                1890

Pro Ala Gln Gly Val Val Thr Thr Leu Glu Asn Val Ser Pro Pro
    1895            1900                1905

Arg Arg Ala Arg Val Thr Asp Ala Thr Glu Thr Thr Ile Thr Ile
    1910            1915                1920

Ser Trp Arg Thr Lys Thr Glu Thr Ile Thr Gly Phe Gln Val Asp
    1925            1930                1935

Ala Val Pro Ala Asn Gly Gln Thr Pro Ile Gln Arg Thr Ile Lys
    1940            1945                1950

Pro Asp Val Arg Ser Tyr Thr Ile Thr Gly Leu Gln Pro Gly Thr
    1955            1960                1965

Asp Tyr Lys Ile Tyr Leu Tyr Thr Leu Asn Asp Asn Ala Arg Ser
    1970            1975                1980

Ser Pro Val Val Ile Asp Ala Ser Thr Ala Ile Asp Ala Pro Ser
    1985            1990                1995

Asn Leu Arg Phe Leu Ala Thr Thr Pro Asn Ser Leu Leu Val Ser
    2000            2005                2010

Trp Gln Pro Pro Arg Ala Arg Ile Thr Gly Tyr Ile Ile Lys Tyr
    2015            2020                2025

Glu Lys Pro Gly Ser Pro Pro Arg Glu Val Val Pro Arg Pro Arg
    2030            2035                2040

Pro Gly Val Thr Glu Ala Thr Ile Thr Gly Leu Glu Pro Gly Thr
    2045            2050                2055

Glu Tyr Thr Ile Tyr Val Ile Ala Leu Lys Asn Asn Gln Lys Ser
    2060            2065                2070

Glu Pro Leu Ile Gly Arg Lys Lys Thr Asp Glu Leu Pro Gln Leu
    2075            2080                2085

Val Thr Leu Pro His Pro Asn Leu His Gly Pro Glu Ile Leu Asp
    2090            2095                2100

Val Pro Ser Thr Val Gln Lys Thr Pro Phe Val Thr His Pro Gly
    2105            2110                2115
```

-continued

| | | | | | | | | | | |
|---|---|---|---|---|---|---|---|---|---|---|
|Tyr|Asp|Thr|Gly|Asn|Gly|Ile|Gln|Leu|Pro|Gly|Thr|Ser|Gly|Gln|
|2120| | | | |2125| | | | |2130| | | | |

Gln Pro Ser Val Gly Gln Gln Met Ile Phe Glu Glu His Gly Phe
2135 2140 2145

Arg Arg Thr Thr Pro Pro Thr Thr Ala Thr Pro Ile Arg His Arg
2150 2155 2160

Pro Arg Pro Tyr Pro Pro Asn Val Gly Glu Glu Ile Gln Ile Gly
2165 2170 2175

His Ile Pro Arg Glu Asp Val Asp Tyr His Leu Tyr Pro His Gly
2180 2185 2190

Pro Gly Leu Asn Pro Asn Ala Ser Thr Gly Gln Glu Ala Leu Ser
2195 2200 2205

Gln Thr Thr Ile Ser Trp Ala Pro Phe Gln Asp Thr Ser Glu Tyr
2210 2215 2220

Ile Ile Ser Cys His Pro Val Gly Thr Asp Glu Glu Pro Leu Gln
2225 2230 2235

Phe Arg Val Pro Gly Thr Ser Thr Ser Ala Thr Leu Thr Gly Leu
2240 2245 2250

Thr Arg Gly Ala Thr Tyr Asn Ile Ile Val Glu Ala Leu Lys Asp
2255 2260 2265

Gln Gln Arg His Lys Val Arg Glu Glu Val Val Thr Val Gly Asn
2270 2275 2280

Ser Val Asn Glu Gly Leu Asn Gln Pro Thr Asp Asp Ser Cys Phe
2285 2290 2295

Asp Pro Tyr Thr Val Ser His Tyr Ala Val Gly Asp Glu Trp Glu
2300 2305 2310

Arg Met Ser Glu Ser Gly Phe Lys Leu Leu Cys Gln Cys Leu Gly
2315 2320 2325

Phe Gly Ser Gly His Phe Arg Cys Asp Ser Ser Arg Trp Cys His
2330 2335 2340

Asp Asn Gly Val Asn Tyr Lys Ile Gly Glu Lys Trp Asp Arg Gln
2345 2350 2355

Gly Glu Asn Gly Gln Met Met Ser Cys Thr Cys Leu Gly Asn Gly
2360 2365 2370

Lys Gly Glu Phe Lys Cys Asp Pro His Glu Ala Thr Cys Tyr Asp
2375 2380 2385

Asp Gly Lys Thr Tyr His Val Gly Glu Gln Trp Gln Lys Glu Tyr
2390 2395 2400

Leu Gly Ala Ile Cys Ser Cys Thr Cys Phe Gly Gly Gln Arg Gly
2405 2410 2415

Trp Arg Cys Asp Asn Cys Arg Arg Pro Gly Gly Glu Pro Ser Pro
2420 2425 2430

Glu Gly Thr Thr Gly Gln Ser Tyr Asn Gln Tyr Ser Gln Arg Tyr
2435 2440 2445

His Gln Arg Thr Asn Thr Asn Val Asn Cys Pro Ile Glu Cys Phe
2450 2455 2460

Met Pro Leu Asp Val Gln Ala Asp Arg Glu Asp Ser Arg Glu
2465 2470 2475

METHODS FOR INHIBITING THE BINDING OF ENDOSIALIN TO LIGANDS

CROSS-REFERENCE TO RELATED APPLICATIONS

This application is a divisional of U.S. application Ser. No. 12/062,630, filed Apr. 4, 2008, now U.S. Pat. No. 7,807,382, which claims the benefit of U.S. Provisional Application No. 60/910,362, filed Apr. 5, 2007, and of U.S. Provisional Application No. 60/980,026, filed Oct. 15, 2007. This application incorporates by reference each of U.S. application Ser. No. 12/062,630, U.S. Application No. 60/910,362, and U.S. Application No. 60/980,026.

FIELD

The invention relates generally to the field of immunotherapeutics. More specifically, the invention relates to compositions and methods for the disruption of endosialin interaction with its substrates to inhibit cellular functions, including angiogenesis and cell motility.

BACKGROUND

Various publications, including patents, published applications, technical articles and scholarly articles are cited throughout the specification. Each of these cited publications is incorporated by reference herein, in its entirety and for all purposes.

Angiogenesis is a regulated process involving the formation of new blood vessels. It plays an essential role in normal growth, embryonic development, wound healing, and other physiological processes (Yancopoulos et al. (2000) *Nature,* 407:242-8). Within the developing capillary, extracellular matrix (ECM) proteins serve as a structural scaffold for proliferating endothelial and tumor tissues and provide support for the growth of tumor cells. De novo angiogenesis is involved in several disease states including cancer, where the formation of new "embryonic-like" blood vessels (referred to as neovascularization herein) appear that differ from normal vasculature with regards to structure and function (Hanahan et al. (2000) *Cell,* 100:57-70). A number of in vivo and in vitro studies have demonstrated biological differences between normal and disease-associated vasculature using various model systems of angiogenesis, thereby raising the possibility of novel anti-angiogenic compounds that can selectively inhibit vessel formation of the embryonic-type, tumor-associated endothelial cells for therapy of neovascular disease. In light of these opportunities for therapy, an intense search for potential targets that can specifically inhibit tumor and other neovascular disease-associated endothelial or stromal (fibroblasts, pericytes, etc.) cell growth and function is ongoing.

In an attempt to identify such targets, strategies have been designed to identify cell surface antigens of tumor stroma as well as isolate specific proteins or RNA that are expressed in tumor stromal cells (Rettig et al. (1992) *Proc. Natl. Acad. Sci. USA,* 89:10832-6; St. Croix et al. (2000) *Science,* 289:1197-1202). These strategies have identified a cell surface protein that appears to be specifically expressed in tumor stromal cells referred to as endosialin (or tumor endothelial marker 1 (TEM1) or CD248).

Examination of gene expression patterns in normal and neoplastic tissue indicates upregulation of endosialin mRNA expression in tumor neovessels. (St Croix et al. (2000) *Science,* 289:1197-1202). Similar endosialin expression levels were noted in human colorectal cancer (Rmali et al. (2005) *World J. Gastroenterol.,* 11:1283-1286), breast cancer tissues (Davies et al. (2004) *Clin. Exp. Metastasis,* 21:31-37), and histiocytomas (Dolznig et al. (2005) *Cancer Immun.,* 5:10). Human endosialin expression has been observed in highly invasive glioblastoma, anaplastic astrocytomas, and metastatic carcinomas, including melanomas (Brady et al. (2004) *J. Neuropathol. Exp. Neurol.,* 63:1274-1283; Huber et al. (2006) *J. Cutan. Pathol.,* 33:145-155).

The use of antibodies in immunohistochemistry studies have found robust expression of endosialin in a number of neovascular endothelial cells, fibroblasts and/or pericytes (Virgintino et al. (2007) *Angiogenesis,* 10:35-45) in malignant tissues, while expression in cell lines derived from embryonic-like endothelial cultures such as but not limited to HUVEC (Human Umbilical Vein Endothelial Cells) or HMVEC-(Neonatal Dermal Microvascular Endothelial Cells) is limited. Analysis of antibodies, polypeptides or non-protein ligands that can bind to endosialin have identified a subset of such molecules that can suppress the ability of endosialin to bind to its substrate and/or suppress intracellular activities leading to cell stasis or death.

Rettig et al. described monoclonal antibodies that recognize antigens on vessels within various cancer types (Rettig et al. (1992) *Proc. Natl. Acad. Sci. USA,* 89:10832-6). One of these was designated FB5 and was generated through immunization of mice with human embryonic fibroblasts. FB5 recognizes a ~100 kDa protein on the surface of a neuroblastoma cell line, LA1-5s (U.S. Pat. No. 5,342,757). FB5 is a murine antibody (IgG1) that binds to endosialin and has been shown to recognize endothelial cells associated with a variety of different cancer types. Structural evaluation has classified endosialin as a C-type lectin-like, integral membrane protein, comprised of five globular extracellular domains (including a C-type lectin domain, one domain with similarity to the Sushi/ccp/scr pattern, and three EGF repeats). The protein also contains a mucin-like region, a transmembrane segment, and a short cytoplasmic tail. The protein appears to be a glycoprotein. Carbohydrate analysis shows that the endosialin core protein has an abundance of O-linked glycosylation (Christian et al. (2001) *J. Biol. Chem.,* 276:48588-48595). Subsequent work combined the complementarity determining regions (CDRs) of the mouse FB5 into a human IgG1 backbone to create a humanized antibody that binds to vessels within malignant tissues as well as a subset of cells in HMVEC cultures.

Tem1 knockout mice develop normally and exhibit normal wound healing, suggesting that endosialin is not required for neovascularization during fetal development or wound repair. (Nanda et al. (2006) *Proc. Natl. Acad. Sci. USA,* 103:3351-3356). When colorectal cancer cells were implanted in the abdominal sites of Tem1 knockout mice, however, the loss of endosialin expression correlated with a reduction in tumor growth, invasion, and metastases as compared to parental animals. The absence of endosialin expression has been shown to reduce growth, invasion, and metastasis of human tumor xenografts in an endosialin knockout mouse. (Nanda et al. (2006) *Proc. Natl. Acad. Sci. USA,* 103:3351-3356). Additionally, lack of endosialin led to an increase in small immature blood vessels and decreased numbers of medium and large tumor vessels.

Neovascularization is associated with a number of disease states. In cancer it is believed that neovascularization is important to supply tumors with blood. In non-oncology cancer or malignant diseases such as retinopathy and macular degeneration, uncontrolled neovascularization causes loss of sight (Wilkinson-Berka (2004) *Curr. Pharm. Des.,* 10:3331-48; Das and McGuire (2003) *Prog. Retin. Eye Res.,* 22:721-

48). Moreover, several reports have identified a role of neovascularization in inflammatory disease (Paleolog and Miotla (1998) *Angiogenesis*, 2(4):295-307). Methods to better understand molecular pathways in embryonic-like endothelial and precursor cells as well as endothelial-associated cells (pericytes, fibroblasts, etc.) associated with these disease states will lead to the development of novel drugs to treat these diseases. Conversely, neovascularization is associated with wound healing (Galiano et al. (2004) *Am. J. Pathol.*, 164:1935-47). Identification of molecular pathways that promote vascularization for wound healing can offer the ability to identify drugs and factors that can promote these processes for enhancing wound treatment associated with trauma, burns and infection.

A difficult problem in effective antiangiogenic and proangiogenic therapy is the nondefined nature of biological processes of molecules and associated pathways that are important for activating cellular processes associated with neovascularization (Bagley et al. (2003) *Cancer Res.*, 63:5866-73). The ability to identify and elucidate molecules and their function in regulating a given pathway can lead to the isolation of effective compounds that have stimulatory or inhibitory activity in neovascular-associated diseases such as cancer, inflammation, ocular disease, cardiovascular disease, and wound healing. The ability to isolate and study these compounds via molecular-based assays would provide further utility for evaluating their effects to specifically suppress or stimulate the normal biology of cells involved in neovascularization in contrast to adult-like endothelial cells associated with vessels in normal adult tissue (Asahara and Kawamoto (2004) *Am. J. Physiol. Cell Physiol.*, 287:C572-9).

SUMMARY

The invention features methods for inhibiting the interaction of an endosialin-expressing cell with a ligand for endosialin.

In one aspect, the methods comprise inhibiting expression of endosialin in an endosialin-expressing cell at the genetic level. Ligands for endosialin can be extracellular matrix proteins such as collagen or fibronectin. In some embodiments, the ligand is collagen I or collagen IV. In preferred embodiments, the cell is a mammalian cell. Regulation of endosialin expression at the genetic level can be effectuated by any means suitable in the art, such as antisense nucleic acid molecule, double stranded RNA, ribozymes, hammerhead ribozymes, decoy oligonucleotides, and the like. Regulation of endosialin expression can also be accomplished by knocking out the gene encoding endosialin.

In another aspect, the methods comprise physically obstructing endosialin expressed on the surface of an endosialin expressing cell, thereby inhibiting the interaction of the cell with an endosialin ligand. Ligands for endosialin can be extracellular matrix proteins such as collagen (e.g., collagen I or collagen IV) or fibronectin.

Obstruction of cell surface endosialin can be effectuated by any means suitable in the art, such as small molecule inhibitors, polypeptide inhibitors, antibodies that specifically bind to endosialin, antibodies that specifically bind to an endosialin ligand, and the like. In some embodiments, competitive inhibitors are employed to inhibit the interaction of endosialin or an endosialin-expressing cell with a ligand for endosialin. In some embodiments, the competitive inhibitors may be endosialin ligands, endosialin-binding fragments of endosialin ligands, for example, endosialin-binding fragments of collagen or fibronectin. Preferred competitive inhibitors are endosialin-binding fragments of collagen I, collagen IV, or fibronectin. Most preferred competitive inhibitors are the 70 kDa N-terminal fragment of fibronectin, the 45 kDa gelatin binding fragment of fibronectin, and the 30 kDa heparin binding fragment of fibronectin.

Suitable antibodies can be chimeric antibodies, humanized antibodies, fully human antibodies, antigen-binding fragments that specifically bind antigen, and the like. In some embodiments, the affinity of antibody for antigen is preferably less than about $1 \times 10^{-7}$ M, more preferably less than about $1 \times 10^{-8}$ M, even more preferably less than about $1 \times 10^{-9}$ M, and most preferably less than about $1 \times 10^{-10}$ M. In some preferred embodiments, the antibody is an anti-endosialin antibody or an antigen-binding fragment that specifically recognizes endosialin. In some embodiments, the antibody or antigen-binding fragment comprises a heavy chain comprising CDR1, CDR2, and CDR3 of SEQ ID NO:28, 30, and 32, respectively, and a light chain comprising CDR1, CDR2, and CDR3 of SEQ ID NO: 13, 15, and 17, respectively. In some embodiments, the antibodies or antigen-binding fragments can comprise a heavy chain comprising a variable domain of SEQ ID NO: 34 and a light chain comprising a variable domain of SEQ ID NO: 19. In some embodiments, the antibodies or antigen-binding fragments can comprise a heavy chain comprising the amino acid sequence of SEQ ID NO:22 or 26 and a light chain comprising the amino acid sequence of SEQ ID NO:11. Antibodies M4 and M4.1 are humanized antibodies to human endosialin. While antibodies M4 and M4.1 share a light chain sequence, they differ in their heavy chain by a single amino acid sequence shown, for example, at residue 429 of SEQ ID NO:20 relative to residue 429 of SEQ ID NO:24. The amino acid change is the result of a single nucleotide alteration shown, for example, at nucleotide 1286 of SEQ ID NO: 19 relative to nucleotide 1286 of SEQ ID NO:23. In some embodiments, the antibodies that can be used in accordance with the invention are produced by cells having ATCC Access. No. PTA-7554 or ATCC Access. No. PTA-9017.

Inhibition of endosialin interaction with ligands for endosialin can affect pathways, cascades, and downstream effects brought about by the normal interaction. For example, obstructing or inhibiting the interaction of an endosialin-expressing cell with an endosialin ligand can inhibit the activation of integrins, the activation of matrix metalloproteases, and/or the expression of matrix metalloproteases. Cell motility can be inhibited. Most preferably, angiogenesis or neovascularization is inhibited.

In some embodiments, inhibition of the interaction of the endosialin-expressing cell with its ligand inhibits the activation of integrin β1, β2, or β3. In some embodiments, inhibition of the interaction of the endosialin-expressing cell with its ligand inhibits migration of the cell. In some embodiments, inhibition of the interaction of the endosialin-expressing cell with its ligand inhibits the activation or expression of a matrix metalloprotease. In preferred embodiments, the matrix metalloprotease is MMP-9.

The invention also features methods for inhibiting angiogenesis or neovascularization. The methods include in vitro and in vivo inhibition of angiogenesis or neovascularization. In some aspects, the methods comprise administering to a subject a therapeutically effective amount of an antibody or antigen-binding fragment that specifically binds endosialin or composition that obstructs endosialin expressed on the surface of a cell such that the interaction of the cell with an endosialin ligand is inhibited. This inhibition suppresses angiogenesis and/or neovascularization of a tissue, organ, or neoplasm in the subject to which the composition is administered. Ligands for endosialin can be extracellular matrix proteins such as collagen (e.g., collagen I or collagen IV) or fibronectin. The composition can comprise any molecule, such as those described and exemplified herein, that can physically obstruct the interaction of cell surface endosialin with at least one endosialin ligand. Examples of such molecules include, without limitation, small molecule inhibitors, polypeptide inhibitors, antibodies that specifically bind to endosialin, antibodies that specifically bind to an endosialin ligand, antigen-binding fragments, and the like. Suitable antibodies can be chimeric antibodies, humanized antibodies, fully human antibodies, antibody fragments, and the like.

Also featured are assays and methods for identifying agents that enhance ("agonists") or reduce ("antagonists") the interaction of endosialin with an endosialin ligand. In one aspect of methods for identifying such antagonists, the methods comprise contacting endosialin with a test compound, thereby forming an endosialin-test compound complex, contacting the endosialin-test compound complex with a ligand for endosialin, and quantifiably measuring the interaction of endosialin with the ligand in the presence and in the absence of the test compound, wherein a decrease in the level of interaction of endosialin with the ligand in the presence of the test compound indicates that the test compound is an antagonist of the interaction of endosialin with the ligand. In one embodiment, the methods for identifying agonists or antagonists of the interaction of endosialin with a ligand for endosialin comprises contacting endosialin with a ligand for endosialin in the presence and absence of a test compound and quantifiably measuring the interaction of endosialin with the ligand, wherein an increase or a decrease in the level of interaction of endosialin with the ligand in the presence of the test compound indicates that the test compound is an agonist or antagonist, respectively, of the interaction of endosialin with the ligand. In the inventive assays, the endosialin can be bound to a cell membrane, a cell membrane fragment, an artificial lipid bilayer, or a solid support. In some aspects, the ligand can be bound to a solid support. Ligands for endosialin can be extracellular matrix proteins such as collagen or fibronectin.

BRIEF DESCRIPTION OF THE DRAWINGS

FIG. 7 shows endosialin binding to EMP fragments and inhibition thereof by endosialin-EMP inhibitor compounds. The fibronectin fragments are illustrated in FIG. 5.

DETAILED DESCRIPTION OF ILLUSTRATIVE EMBODIMENTS

Figure 1A:
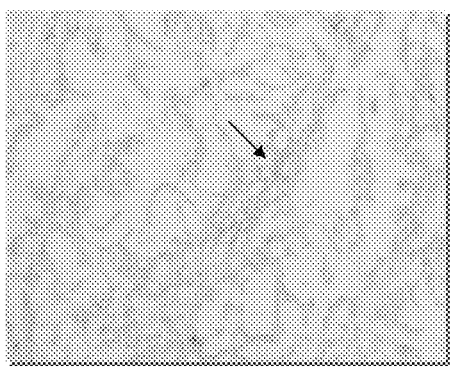
FIGS. 1A and 1B show immunohistochemical analysis of endosialin-positive cells of malignant tissue. Tumors were isolated from patients with colorectal cancer and flash frozen in liquid nitrogen. Samples were thin-sectioned and stained with anti-endosialin or isotype control antibody. As shown, vessels in the tumor (FIG. 1A) stained positive for endosialin while isotype control antibody stained serial section was negative (FIG. 1B).

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a cell" includes a combination of two or more cells, and the like.

Each range recited herein includes all combinations and sub-combinations of ranges, as well as specific numerals contained therein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Endosialin specific assay" (ESA) refers to assays that can be used to identify compounds that can directly or indirectly perturb endosialin expression or biological activity that results in modified direct or indirect binding of endosialin-expressing cells or endosialin to EMPs via endosialin or integrin-mediated mechanisms as well as modify cellular endogenous pathways such as but not limited to matrix metalloprotease (MMPs) and/or cellular proliferation or survival.

"Polynucleotide," synonymously referred to as "nucleic acid" or "nucleic acid molecule," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus to which another nucleic acid segment may be operably inserted so as to bring about the replication or expression of the segment.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides of the invention include conservatively modified variants. One of skill will recognize that substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "express," "expressed," or "expression" of a nucleic acid molecule refers to the biosynthesis of a gene product. The term encompasses the transcription of a gene into RNA. For example, but not by way of limitation, a regulatory gene such as an antisense nucleic acid or interfering nucleic acid can be expressed by transcription as antisense RNA or RNAi or shRNA. The term also encompasses translation of RNA into one or more polypeptides, and encompasses all naturally occurring post-transcriptional and post-translational modifications.

A cell has been "transformed" or "transfected" by exogenous or heterologous nucleic acids such as DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As used herein, "test compound" refers to any purified molecule, substantially purified molecule, molecules that are one or more components of a mixture of compounds, or a mixture of a compound with any other material that can be utilized in the methods of the present invention. Test compounds can be organic or inorganic chemicals, or biomolecules, and all fragments, analogs, homologs, conjugates, and derivatives thereof. "Biomolecules" include proteins, polypeptides, nucleic acids, lipids, monosaccharides, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like.

"Knockdown" refers to a cell or organism having reduced expression of one or more genes. As will be appreciated by those skilled in the art, a knockdown will exhibit at least about a 50% reduction in expression, preferably will exhibit at least about a 67% reduction in expression, and more preferably will exhibit at least about a 75% reduction in expression, although higher reductions are possible, including at least about a 80%, 81%, 82%, 83%, 84%, 85%, 86%, 87%, 88%, 89%, 90%, 91%, 92%, 93%, 94%, 95%, 96%, 97%, 98%, 99%, or more reduction in expression.

"Inhibit" or "inhibition" or "interfere" means to reduce, decrease, block, prevent, delay, suppress, inactivate, desensitize, stop, or downregulate the biological activity or expression of a gene, gene product (e.g., polypeptide), or pathway of interest. In some preferred embodiments of the invention, the inhibition of the expression or biological activity of a protein or pathway of interest, for example, endosialin or cell migration pathway, refers to a decrease (inhibition or downregulation) of greater than from about 50% to about 99%, and more specifically, about 50%, 51%, 52%, 53%, 54%, 55%, 56%, 57%, 58%, 59%, 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more. The inhibition may be direct, i.e., operate on the molecule or pathway of interest itself, or indirect, i.e., operate on a molecule or pathway that affects the molecule or pathway of interest.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Effective amount" and "therapeutically effective amount" are used interchangeably herein, and refer to an amount of an antibody, antigen-binding fragment, or composition, as described herein, effective to achieve a particular biological result such as, but not limited to, biological results disclosed, described, or exemplified herein. Such results may include, but are not limited to, the treatment of disease associated with angiogenesis or neovascularization, as determined by any means suitable in the art.

As used herein, "measure" or "determine" refers to any qualitative or quantitative determinations.

"Endosialin ligand" refers to any chemical, biomolecule, complex, or analog, homolog, or derivative thereof that can bind to, interact with, stimulate, and/or alter expression of endosialin.

Except when noted, "subject" or "patient" are used interchangeably and refer to mammals such as human patients and non-human primates, as well as experimental animals such as rabbits, dogs, cats, rats, mice, and other animals. Accordingly, "subject" or "patient" as used herein means any mammalian patient or subject to which the compositions of the invention can be administered.

"Angiogenesis" refers to the formation of new blood vessels.

"Neovascularization" refers to a pathological proliferation of new blood vessels in a tissue(s) or organ(s) that normally do(es) not contain blood vessels, or a pathological proliferation of blood vessels of a different type or quantity than normal for a particular tissue or organ.

"Epitope" refers to an immunological determinant of an antigen that serves as an antibody-binding site. As used herein, the term "conformational epitope" refers to a discontinuous epitope formed by a spatial relationship between amino acids of an antigen other than an unbroken series of amino acids.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Substantially the same" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity.

It has been discovered in accordance with the present invention that endosialin specifically interacts with extracellular matrix proteins, including fibronectin or collagen. It has also been discovered that this interaction promotes cell migration and further promotes and facilitates angiogenesis. Further to these observations, it has been discovered that disruption of the interaction between endosialin and extracellular matrix proteins can suppress cell migration and can suppress angiogenesis. Accordingly, the invention features methods for inhibiting the interaction of endosialin with endosialin ligands.

In one aspect, the invention features methods for inhibiting the interaction of endosialin expressed by an endosialin-expressing cell with an endosialin ligand. In some preferred embodiments, the methods comprise inhibiting endosialin expression by the cell. Inhibiting the expression of endosialin can occur at the gene level or the protein level. For example, inhibiting the expression of endosialin can comprise targeting the DNA encoding endosialin, or targeting the mRNA transcript of the endosialin gene.

Methods of gene regulation are known and readily practiced in the art, and are all suitable for use in the inventive methods. For example, in cells specifically engineered to express a transgene encoding endosialin (e.g., SEQ ID NO:1, 3, or 5), the transgene can be placed under control of an inducible promoter. Inducible promoters suitable for use in this invention will be known to those of skill in the art.

In some preferred embodiments, genes encoding endosialin can be inhibited through the use of a variety of other post-transcriptional gene silencing (RNA silencing) techniques. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner.

RNA interference (RNAi) is a mechanism of post-transcriptional gene silencing mediated by double-stranded RNA (dsRNA), which is distinct from antisense and ribozyme-based approaches (see Jain, *Pharmacogenomics* (2004) 5:239-42, for a review of RNAi and siRNA). RNA interference is useful in a method for inhibiting the expression of endosialin in a cell or in an animal such as a human by transforming the cell, or by administering to the animal a nucleic acid (e.g., dsRNA) that hybridizes under stringent conditions to a gene encoding endosialin, and attenuates expression of the target gene. RNA interference provides shRNA or siRNA that comprise multiple sequences that target one or more regions of the endosialin gene. Double stranded RNA (dsRNA) molecules (shRNA or siRNA) are believed to direct sequence-specific degradation of mRNA in cells of various types after first undergoing processing by an RNase III-like enzyme called DICER (Bernstein E et al. (2001) Nature 409:363-366) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA), which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. An siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript, meaning that the siRNA hybridizes to the target transcript without a single mismatch. In certain embodiments of the invention in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. RNA interference using siRNA is reviewed in, e.g., Tuschl (2002) *Nat. Biotechnol.* 20:446-8; Yu J-Y et al. (2002) *Proc. Natl. Acad. Sci. USA*, 99:6047-52; Sui G et al. (2002) *Proc. Natl. Acad. Sci. USA*, 99:5515-20; Paddison et al. (2002) *Genes and Dev.*, 16:948-58; Brummelkamp et al. (2002) *Science*, 296:550-3, 2002; Miyagashi et al. (2002) *Nat. Biotechnol.*, 20:497-500; and, Paul et al. (2002) *Nat. Biotechnol.*, 20:505-8. As described in these and other references, the siRNA may consist of two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is thought that intracellular processing (e.g., by DICER) of a variety of different precursors results in production of siRNA capable of effectively mediating gene silencing. Generally it is preferred to target exons rather than introns, and it may also be preferable to select sequences complementary to regions within the 3' portion of the target transcript. Generally it is preferred to select sequences that contain approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. As used herein, siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop (Grishok et al. (2001) *Cell*, 106:23-4; Hutvagner et al. (2001) *Science*, 293: 834-8; Ketting et al. (2001) *Genes Dev.*, 15:2654-9). Endogenous RNAs of this type have been identified in a number of organisms including mammals, suggesting that this mechanism of post-transcriptional gene silencing may be widespread (Lagos-Quintana et al. (2001) *Science*, 294:853-8, 2001; Pasquinelli (2002) *Trends Gen.*, 18:171-3). MicroRNAs have been shown to block translation of target transcripts containing target sites in mammalian cells (Zeng et al. (2002) *Mol. Cell*, 9:1327-33).

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of non-identity (mismatch) need not be symmetrical in the sense that both the target and the mRNA include nonpaired nucleotides. Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (McManus et al. (2002) *RNA* 8:842-50). These hairpin structures, which are based on classical siRNAs consisting of two RNA strands forming a 19 bp duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and siRNAs.

Thus, it is evident that a diverse set of RNA molecules containing duplex structures is able to mediate silencing through various mechanisms. For the purposes of the present invention, any such RNA, one portion of which binds to a target transcript and reduces its expression, whether by triggering degradation, by inhibiting translation, or by other means, is considered to be an siRNA, and any structure that generates such an siRNA (i.e., serves as a precursor to the RNA) is useful in the practice of the present invention.

A further method of RNA interference for use in the present invention is the use of short hairpin RNAs (shRNA). A plasmid containing a DNA sequence encoding for a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression Inhibition of protein expression by transfected siRNAs is a transient phenomenon that does not occur for times periods longer than several days. In some cases, this may be preferable and desired. In cases where longer periods of protein inhibition are necessary, shRNA mediated inhibition is preferable. The use of shRNA is particularly preferred. Typically, siRNA-encoding vectors are constructs comprising a promoter, a sequence of the target gene to be silenced in the "sense" orientation, a spacer, the antisense of the target gene sequence, and a terminator.

Inhibition of the expression of endosialin can also be effectuated by other means that are known and readily practiced in the art. For example, antisense nucleic acids can be used. Antisense RNA transcripts have a base sequence complementary to part or all of any other RNA transcript in the same cell. Such transcripts have been shown to modulate gene expression through a variety of mechanisms including the modulation of RNA splicing, the modulation of RNA transport and the modulation of the translation of mRNA (Denhardt (1992) *Ann. N Y Acad. Sci.,* 660:70-6, 1992; Nellen et al. (1993) *Trends Biochem. Sci.,* 18:419-23; and, Baker et al. (1999) *Biochim. Biophys. Acta.,* 1489: 3-18). Accordingly, in certain embodiments of the invention, inhibition of endosialin in a cell is accomplished by expressing an antisense nucleic acid molecule in the cell.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the function of the target nucleic acid, such as a gene encoding endosialin. For example, antisense oligonucleotides may block transcription when bound to genomic DNA, inhibit translation when bound to mRNA, and/or lead to degradation of the nucleic acid. Inhibition of the expression of endosialin can be achieved by the administration of antisense nucleic acids or peptide nucleic acids comprising sequences complementary to those of the mRNA that encodes the endosialin protein. Antisense technology and its applications are well known in the art and are described in Phillips (ed.) *Antisense Technology, Methods Enzymol.,* 2000, Volumes 313 and 314, Academic Press, San Diego, and references mentioned therein. See also Crooke (ed.) "ANTISENSE DRUG TECHNOLOGY: PRINCIPLES, STRATEGIES, AND APPLICATIONS" ($1^{st}$ Edition) Marcel Dekker and references cited therein.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C) (Wagner (1995) *Nat. Medicine,* 1:1116-8; Varga et al. (1999) *Immun. Lett.,* 69:217-24; Neilsen (1999) *Curr. Opin. Biotech.,* 10:71-5; and Woolf (1990) *Nucleic Acids Res.,* 18:1763-9).

Inhibition of endosialin gene expression can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation (Cotten et al. (1989) *EMBO J.,* 8:861-6; and, Usman et al. (1996) *Curr. Opin. Struct. Biol.,* 1:527-33). Hammerhead ribozymes are also routinely used in gene regulation (Lyngstadaas (2001) *Crit. Rev. Oral Biol. Med.,* 12:469-78).

In preferred aspects of the invention, the cells targeted by the inventive methods can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art, including those described and exemplified herein.

Decoy oligonucleotides are also suitable for regulating the expression of endosialin-encoding genes. Recent clinical trials have tested the ability of decoy oligonucleotides to sequester pathogenic proteins. Decoy oligonucleotides generally contain an enhancer element that can penetrate cells, and once inside cells, the decoy oligonucleotides bind to sequence-specific DNA-binding proteins and interfere with transcription (Fichou et al., (2006) *Trends Biotechnol.,* 24:563-70; Nakamura et al. (2002) *In Vivo,* 16:45-8; Tomita et al. (1997) *Exp. Nephrol.,* 5:429-34).

Genetic regulation of endosialin expression can also be effectuated by knockdown of the gene encoding endosialin. As will be appreciated by those of skill in the art, the sequence of the endosialin gene (from any organism of interest), for example, SEQ ID NO: 1, 3, or 5, can be used to generate nucleic acid molecules and vectors for knockdown expression of the endosialin gene. Considered in terms of their sequences, the nucleic acid molecules that encode regulatory, particularly inhibitory, sequences derived from SEQ ID NOs: 1, 3, and 5, include allelic variants, homologs, and natural mutants of SEQ ID NOs: 1, 3, and 5. Because such variants and homologs are expected to possess certain differences in nucleotide sequence, this invention provides isolated polynucleotides that have at least about 60%, preferably at least about 61%, 62%, 63%, 64%, 65%, 66%, 67%, 68%, 69% or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any knockdown nucleic acid derived from SEQ ID NOs: 1, 3, or 5. Because of the natural sequence variation likely to exist among genes encoding these regulatory sequences in different organisms, one skilled in the art would expect to find this level of variation, while still maintaining the unique properties of the knockdown polynucleotides. Accordingly, such variants and homologs are considered substantially the same as one another and are included within the scope of the present invention.

Knockdown nucleic acid molecules can be prepared by two general methods: (1) they may be synthesized from appropriate nucleotide triphosphates, or (2) they may be isolated from biological sources. Both methods utilize protocols well known in the art.

The availability of nucleotide sequence information such as the entire nucleic acid sequence of endosialin, for example, SEQ ID NOs:1, 3, and 5, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). A synthetic DNA molecule so constructed may then be cloned and amplified in an appropriate vector.

Knockdown nucleic acids may be maintained as DNA in any convenient cloning vector. In some preferred aspects, clones are maintained in plasmid cloning/expression vector, either of which can be propagated in a suitable prokaryotic or eukaryotic host cell.

Knockdown nucleic acid molecules include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention, in particular, SEQ ID NOs: 1, 3, or 5. Such oligonucleotides are useful as probes for detecting genes encoding endosialin, or for the positive or negative regulation of expression of genes encoding endosialin at or before translation of the mRNA into the protein. Methods in which oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR) and ligase chain reaction (LCR).

Also featured in accordance with the present invention are vectors and kits for producing transgenic host cells that comprise a polynucleotide encoding a regulatory sequence for inhibiting the expression of endosialin, or homolog, analog or variant thereof in a sense or antisense orientation, or a construct under control of cell or tissue-specific promoters and/or other regulatory sequences. Such vectors are suitable for modulating, and preferably inhibiting, the expression of endosialin.

Suitable host cells include, but are not limited to, plant cells, bacterial cells, yeast and other fungal cells, insect cells and mammalian cells that express endosialin. The cells can be neoplastically transformed. More preferred are human cells.

Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors.

The coding region of a regulatory sequence can be placed under a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use in the present invention. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. Other promoters are known to those of ordinary skill in the art. In one embodiment, the coding region of the regulatory sequence is placed under an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like. Other suitable inducible promoters will be known to those of skill in the art.

Knockdown vectors can be used to transform various endosialin-expressing cells with regulatory nucleic acid sequences. Numerous techniques are known in the art for the introduction of foreign genes into cells and may be used to construct recombinant cells for purposes of carrying out the inventive methods, in accordance with the various embodiments of the invention. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline (1985) *Pharmac. Ther.*, 29:69-92).

Knockdown cells with inhibited expression of endosialin can be created by inhibiting the translation of mRNA encoding the transport protein by "post-transcriptional gene silencing." The gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. Antisense molecules may be provided in situ by transforming cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example, see Waterhouse et al. (1998) *Proc. Natl. Acad. Sci. U.S.A.*, 95:13959-64). In this regard, dsRNA containing sequences that correspond to part or all of at least one intron have been found particularly effective. In one embodiment, part or all of the coding sequence antisense strand is expressed by a transgene. In another embodiment, hybridizing sense and antisense strands of part or all of the coding sequence for one endosialin are transgenically expressed.

Cells that can be targeted by or otherwise used in the methods of the invention include endosialin-expressing cells that naturally express endosialin or cells transfected with a recombinant plasmid expressing endosialin. Primary endosialin-expressing cells of the invention can be isolated from tissues or purchased from vendors selling endothelial cells, such as but not limited to HMVEC or HMVEC as well as primary and cultured fibroblasts. Transfected cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK cells, mouse sertoli cells, human cervical carcinoma cells, buffalo rat liver cells, human lung cells, human liver cells, mouse mammary tumor cells, TR1 cells, MRC 5 cells, and FS4 cells.

Inhibiting the expression of endosialin inhibits the interaction of endosialin with any endosialin ligand. Endosialin ligands include extracellular matrix proteins such as fibronectin and collagen.

Also featured in accordance with the present invention are methods for inhibiting the interaction of endosialin expressed by an endosialin expressing cell with an endosialin ligand that comprise blocking or obstructing the endosialin expression by the cell. Thus, for example, a physical barrier serves to inhibit, impede, or otherwise hinder the interaction of expressed endosialin with an endosialin ligand. Any chemical or biomolecule can serve to obstruct this interaction. For example, small molecules, polypeptides, antibodies, and antigen-binding fragments thereof that specifically bind to endosialin, or in the alternative, specifically bind to an endosialin ligand can be used in this methods.

In some preferred embodiments, inhibiting the interaction of an endosialin-expressing cell with a ligand for endosialin comprises inhibiting the binding of the endosialin ligand to the expressed endosialin. For example, the interaction between endosialin and its ligand is hindered, blocked, impeded, or otherwise obstructed with a molecular barrier. In this way, access to the cell by the ligand is thus hindered, inhibited, blocked, impeded, obstructed or prevented. Obstruction of the endosialin can occur by any means suitable in the art, such as with a chemical or biomolecule.

For example, chemicals suitable for use in the inventive methods include, but are not limited to, amino acid structures, steroids, cyclines, anthracenes, heavy metals, quinilone, terpenes, phenolics, glycosides, alkyloids, lipids, etc. or mixtures thereof that can exert a biological effect on endosialin-expressing cells. Chemicals can be generated by chemical synthesis or derived from biocatalysis or derived from biological fluids. Chemicals can be derived from human, non-human mammalian, plant, yeast, fungi and/or prokaryotic sources.

In some embodiments, competitive inhibitors are employed to inhibit the interaction of endosialin or an endosialin-expressing cell with a ligand for endosialin. A "competitive inhibitor" competes with the ligand for the binding site to endosialin. In some embodiments, the competitive inhibitors are endosialin ligands, for example, collagen (e.g., collagen I or IV) or fibronectin, or endosialin-binding fragments thereof. Most preferred competitive inhibitors are the 70 kDa N-terminal fragment of fibronectin, the 45 kDa gelatin binding fragment of fibronectin, and the 30 kDa heparin binding fragment of fibronectin.

In highly preferred embodiments, antibodies or antigen-binding fragments thereof are used to obstruct the interaction of expressed endosialin with endosialin ligands. The antibodies or antigen-binding fragments can be specific for an epitope on endosialin, or can be specific for an epitope on an endosialin ligand. Antibodies and antigen-binding fragments thereof specific for endosialin are more preferred. Antibodies to ligands such as fibronectin, collagen, and the like are commercially available.

Suitable antibodies can be polyclonal or monoclonal, or can be derivatives or fragments of antibodies that retain specificity for endosialin or an endosialin ligand. The antibodies can be from any of the five classes of antibodies, i.e., the IgA, IgD, IgE, IgG and IgM isotypes. Suitable antibodies also include the IgY isotype generally found in hen or turkey serum and hen or turkey egg yolk.

Antibody derivatives and antigen-binding fragments are suitable for use in the inventive methods, and such derivatives comprise portions of intact antibodies that retain antigen-binding specificity of the parent antibody molecule. For example, derivatives can comprise at least one variable region (either a heavy chain or light chain variable region). Examples of suitable antibody derivatives and fragments include, without limitation antibodies with polyepitopic specificity, bispecific antibodies, diabodies, and single-chain molecules, as well as Fab, F(ab')2, Fd, Fabc, and Fv molecules, single chain (Sc) antibodies, individual antibody light chains, individual antibody heavy chains, chimeric fusions between antibody chains and other molecules, heavy chain monomers or dimers, light chain monomers or dimers, dimers consisting of one heavy and one light chain, and the like. All antibody isotypes can be used to produce antibody derivatives and fragments. Antibody derivatives and fragments can be recombinantly produced.

Antibodies suitable for use in the inventive methods can be derived from any species. For example, the antibodies can be mouse, rat, goat, horse, swine, bovine, chicken, rabbit, donkey, human, and the like. For use in methods of treatment, or for administration to humans, non-human derived antibodies can be structurally altered to be less antigenic upon administration to a human patient.

Thus, in some embodiments of the invention, the antibodies used in the inventive methods are chimeric antibodies. Chimeric antibodies and methods to produce them are well known and established in the art. For example, a chimeric antibody may comprise a mouse antigen binding domain with a human Fc or other such structural domain.

In some embodiments, the antibodies are humanized antibodies. Humanized antibodies can be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FWR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FWR regions are those of a human immunoglobulin sequence. The humanized antibody optimally also will comprise at least a portion of an immunoglobulin constant region (Fc), typically that of a human immunoglobulin. For further details, see Jones et al. (1986) *Nature,* 321:522-5; Reichmann et al. (1988) *Nature,* 332:323-9; and Presta (1992) *Curr. Op. Struct. Biol.,* 2:593-6.

In preferred aspects of the invention, the antibodies are fully human. This means that the antibody is solely from human origin, or otherwise consists of an amino acid sequence identical to a human form of the antibody.

The antibodies of the invention can be labeled or otherwise conjugated to various chemical or biomolecule moieties, for example, for therapeutic or diagnostic applications. The moieties can be cytotoxic, for example, bacterial toxins, viral toxins, radioisotopes, and the like. The moieties can be detectable labels, for example, fluorescent labels, radiolabels, biotin, and the like. Additional moieties include, but are not limited to glycosylation, acetylation, pegylation, phosphorylation, and amidation. The antibodies useful in the methods of the invention may themselves by derivatized by known protecting/blocking groups, proteolytic cleavage, linkage to a cellular ligand or other proteins, and the like.

Those of skill in the art will recognize that antibody specificity is primarily determined by the six CDR regions, especially H chain CDR3 (Kala et al. (2002) *J. Biochem.,* 132: 535-41; Morea et al. (1998) *J. Mol. Biol.,* 275:269-94; and, Chothia et al. (1987) *J. Mol. Biol.,* 196:901-17). Antibody framework regions, however, can play a role in antigen-antibody interactions (Panka et al. (1988) *Proc. Natl. Acad. Sci. USA,* 85:3080-4), particularly with respect to their role in conformation of CDR loops (Foote et al. (1992) *J. Mol. Biol.,* 224:487-99). Thus, antibodies suitable for use in the inventive methods can comprise any combination of H or L chain CDR or FWR regions that confer antibody specificity for endosialin or endosialin ligands.

In some embodiments, the invention contemplates the use of isolated human antibodies and antigen-binding fragments thereof that specifically bind to endosialin. In some embodiments, suitable antibodies or antigen-binding fragments can comprise a heavy chain comprising CDR1, CDR2, and CDR3 of SEQ ID NO:28, 30, and 32, respectively, and a light chain comprising CDR1, CDR2, and CDR3 of SEQ ID NO: 13, 15, and 17, respectively. In some embodiments, the heavy chain CDR1, CDR2, and CDR3 are encoded by nucleotide sequences of SEQ ID NO:27, 29, and 31, respectively. In some embodiments, the light chain CDR1, CDR2, and CDR3 are encoded by nucleotide sequences of SEQ ID NO:12, 14, and 16, respectively. In some embodiments, the antibodies or antigen-binding fragments can comprise a heavy chain comprising a variable domain of SEQ ID NO: 34 and a light chain comprising a variable domain of SEQ ID NO: 19. In some embodiments, the heavy chain variable domain is encoded by the nucleotide sequence of SEQ ID NO:33. In some embodiments, the light chain variable domain is encoded by the nucleotide sequence of SEQ ID NO:18. In some embodiments, the antibodies or antigen-binding fragments can comprise a heavy chain comprising the amino acid sequence of SEQ ID NO:22 or 26 and a light chain comprising the amino acid sequence of SEQ ID NO:11. In some embodiments, the heavy chain is encoded by the nucleotide sequence of SEQ ID NO:21 or 25 and the light chain is encoded by the nucleotide sequence of SEQ ID NO:10. In some embodiments, the antibodies or antigen-binding fragments comprise a heavy chain comprising SEQ ID NO:20 or 24 and a light chain comprising SEQ ID NO:9. In some embodiments, the antibodies comprise a heavy chain encoded by the nucleic acid sequence of SEQ ID NO:8 or 23. Antibodies or antigen-binding fragments can comprise a light chain encoded by the nucleic acid sequence that comprises SEQ ID NO:7.

Antibody-producing cells producing antibodies that can be used in accordance with the invention have been placed with the Amer. Type Cult. Coll. (10801 University Blvd., Manassas, Va. 20110-2209) on Apr. 24, 2006 and on Mar. 11, 2008 and have been assigned Access. Nos. PTA-7554 and PTA-9017, respectively.

It is to be understood that, because of the natural sequence variation likely to exist among heavy and light chains and the genes encoding them, one skilled in the art would expect to find some level of variation within the amino acid sequences or the genes encoding them, while still maintaining the unique binding properties (e.g., specificity and affinity) of the antibodies of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

Variants having single or multiple amino acid substitutions, deletions, additions, or replacements that retain the biological properties (e.g., binding affinity or immune effector activity) of the antibodies described herein are contemplated for use in the invention. The skilled person can produce variants having single or multiple amino acid substitutions, deletions, additions or replacements. These variants may include, for example: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

The present invention contemplates antibodies, or antigen-binding fragments thereof, having amino acid sequences that are substantially the same as the previously described amino acid sequences. For example, such antibodies or antigen-binding fragments may include those wherein the heavy chain CDR1, CDR2, and CDR3 are at least 90% identical to SEQ ID NO:28, 30, and 32, respectively, and/or wherein the light chain CDR1, CDR2, and CDR3 are at least 90% identical to SEQ ID NO: 13, 15, and 17, respectively. In some embodiments, such antibodies or antigen-binding fragments may include those wherein the heavy chain variable domain is at least 90% identical to SEQ ID NO: 34 and/or wherein the light chain variable domain is at least 90% identical to SEQ ID NO: 19. In some embodiments, the antibodies or antigen-binding fragments may include those wherein the heavy chain is at least 90% identical to SEQ ID NO:22 or 26 and/or wherein the light chain is at least 90% identical to SEQ ID NO:11. In some embodiments, the antibodies or antigen-binding fragments may include those wherein the heavy chain is at least 90% identical to SEQ ID NO:20 or 24 and/or wherein the light chain is at least 90% identical to SEQ ID NO:9. For example, antibodies M4 and M4.1 are humanized antibodies to human endosialin. While antibodies M4 and M4.1 share a light chain sequence, they differ in their heavy chain by a single amino acid sequence shown, for example, at residue 429 of SEQ ID NO:20 relative to residue 429 of SEQ ID NO:24. The invention further contemplates antibodies, or antigen-binding fragments thereof, that compete for binding to endosialin with antibody M4 or M4.1. The invention further contemplates antibodies, or antigen-binding fragments thereof, that bind the same epitope of endosialin as antibody M4 or M4.1.

Antibodies suitable for use in the methods of the invention can have binding affinities for the target antigen, such as endosialin or an endosialin ligand, that include a dissociation constant ($K_D$) of less than $1 \times 10^{-2}$ M. In some embodiments, the $K_D$ is less than $1 \times 10^{-3}$ M. In other embodiments, the $K_D$ is less than $1 \times 10^{-4}$ M. In some embodiments, the $K_D$ is less than $1 \times 10^{-5}$ M. In still other embodiments, the $K_D$ is less than $1 \times 10^{-6}$ M. In other embodiments, the $K_D$ is less than $1 \times 10^{-7}$ M. In other embodiments, the $K_D$ is less than $1 \times 10^{-8}$ M. In other embodiments, the $K_D$ is less than $1 \times 10^{-9}$ M. In other embodiments, the $K_D$ is less than $1 \times 10^{-10}$ M. In still other embodiments, the $K_D$ is less than $1 \times 10^{-11}$ M. In some embodiments, the $K_D$ is less than $1 \times 10^{-12}$ M. In other embodiments, the $K_D$ is less than $1 \times 10^{-13}$ M. In other embodiments, the $K_D$ is less than $1 \times 10^{-14}$ M. In still other embodiments, the $K_D$ is less than $1 \times 10^{-15}$ M.

Specificity and/or affinity of antibodies that bind to endosialin can optionally be optimized by directed evolution of the cells producing the antibody, by using a dominant negative allele of a mismatch repair gene such as PMS1, PMS2, PMS2-134, PMSR2, PMSR3, MLH1, MLH2, MLH3, MLH4, MLH5, MLH6, PMSL9, MSH1, and MSH2 introduced into the antibody-producing cells. Cells containing the dominant negative mutant will become hypermutable and accumulate mutations at a higher rate than untransfected control cells. A pool of the mutating cells may be screened for clones that produce higher affinity/specificity of antibodies or binding proteins, or that produce higher titers of antibodies or binding proteins, or that simply grow faster or better under certain conditions. The technique for generating hypermutable cells using dominant negative alleles of mismatch repair genes is described in U.S. Pat. No. 6,146,894. Alternatively, mismatch repair may be inhibited using the chemical inhibitors of mismatch repair described in WO 02/054856. The technique for enhancing antibodies using the dominant negative alleles of mismatch repair genes or chemical inhibitors of mismatch repair may be applied to mammalian, yeast, plant or prokaryotic expression cells expressing cloned immunoglobulin or protein genes as well. Cells expressing the dominant negative alleles or small molecule can be "cured" in that the dominant negative allele can be turned off, if inducible, eliminated from the cell while the small chemical can be removed from grow culture resulting in cells that are genetically stable once more and no longer accumulate mutations at the abnormally high rate.

Inhibiting the expression of endosialin inhibits the interaction of endosialin with any endosialin ligand. Endosialin ligands include extracellular matrix proteins, such as fibronectin and collagen. Any collagen subtype can serve as a ligand to endosialin. Collagen I and Collagen IV are more preferred.

Inhibiting the interaction of endosialin with endosialin ligands inhibits pathways and cascades that are upregulated or otherwise activated as a result of this interaction. For example, endosialin interaction with endosialin ligands can promote the expression and/or activation of adhesion molecules such as integrins, which mediate cell attachment to the extracellular matrix or to other cells, and which mediate cell signal pathways, among other things.

Integrins tend to exist as heterodimers containing two distinct chains, an α (alpha) and β (beta) subunit. There are approximately 18 α and 8 β subunits that have been characterized. In addition, a number of integrin subunits exist as variants via differential splicing. The various combinations of alpha and beta integrin subunits results in over 24 unique active integrin complexes (Hynes (2002) *Cell,* 110:673). Integrin subunits penetrate the plasma membrane, and in general contain short cytoplasmic domains of about 40-70 amino acids. Outside the cell plasma membrane, the alpha and beta chains lie in close proximity to each other along a length of about 23 nm. The amino-termini of each integrin chain are juxtaposed within 5 nm of each other to form a ligand-binding region for EMP interaction. Integrins are categorized using several criteria. Alpha chains are classified as such because a subset of the a chains have structural elements inserted near the amino-terminus called alpha-A domain because it has a similar structural motif as the A-domains within the von Willebrand factor. Integrins carrying this domain can either bind to collagens (integrin complexes α1β1 and α2β1), or act as cell-cell adhesion molecules with those complexes containing integrins of the β2 family. Two main functions of integrins are attachment of the cell to extracellular matrix proteins and signal transduction mediated from the EMP-integrin binding to the cell. In addition, integrins are also involved in a wide range of other biological activities including binding of viruses, such as adenovirus, Echo viruses, Hanta viruses, foot and mouth disease viruses as well as binding to cells involved in immune patrolling and cell-cell contact for cell migration. Integrins couple EMPs (which depends on the integrin complex) to the cytoskeleton within the cell. Several ligands of integrins have been identified. The more common ligands are fibronectin, vitronectin, collagen, and laminin. The interactions between integrin, an EMP and the microfilaments inside the cell are linked via scaffolding proteins including talin, paxillin and alpha-actinin. These interactions result in regulation of kinases like FAK (focal adhesion kinase) and Src kinase family members to phosphorylate substrates such as p130CAS thereby recruiting signaling adaptors such as Crk for mediating cellular responses including pathway activation, cellular proliferation and/or survival. Any of these integrin-associated functions can be assembled as a screening assay to monitor integrin activity as a function of endosialin activity for assays to identify pharmacologic agents or effective endosialin targeting molecules of this invention. Moreover, in light of the invention disclosed here, targeting integrins with pharmacologic agents to endosialin in endosialin-expressing cells have broad opportunities in suppressing integrin-mediated viral infection and other pathologies.

Thus, inhibiting the interaction of endosialin with an endosialin ligand inhibits the expression and/or activation of integrin molecules on the endosialin-expressing cell. In some preferred embodiments, the expression or activation of integrin β1, β2, or β3 is suppressed by the inhibition.

Other molecules and pathways whose expression and/or activation are affected by the inhibition of endosialin interaction with endosialin ligands include matrix metalloproteinases (MMPs). MMPs are zinc-dependent proteases that play a role in, among other things, degradation of extracellular matrix proteins, cell surface receptors, and the like. MMPs play a role in cell migration, proliferation, and angiogenesis, among other things. The MMP family of enzymes have a common zinc binding motif (HExxHxxGxxH) within their active site, and a conserved methionine following the active site. MMPs are classified by their homology to one another, substrate specificity and partly on their cellular localization. They are broadly grouped into 4 classes: collagenase, stromelysins, gelatinase, and the membrane type MMPs (MT-MMPs). Collagenase-type MMPs are capable of degrading triple-helical fibrillar collagens into distinctive fragments. These collagens are the major components of bone and cartilage, and this class of MMPs are the only known mammalian enzymes capable of degrading them. They include MMP-1 (Interstitial collagenase); MMP-8 (Neutrophil collagenase); MMP-13 (Collagenase 3); and MMP-18. Stromelysin-type MMP enzymes display a broad ability to cleave EMPs but are unable to cleave the triple-helical fibrillar collagens. This class includes MMP-3 (Stromelysin 1); MMP-10 (Stromelysin 2); MMP-11 (Stromelysin 3); MMP-12 (Macrophage metalloelastase); MMP-19 (RASI-1, also referred to as stromelysin-4); and MMP-20 (enamelysin); MMP-22 (C-MMP) and MMP-27. Gelatinase-type MMPs degrade mainly type IV collagen and gelatin, and are distinguished by the presence of an additional domain inserted into the catalytic domain. This gelatin-binding region is positioned immediately before the zinc binding motif, and forms a separate folding unit which does not disrupt the structure of the catalytic domain. This class includes MMP-2 (72 kDa gelatinase, gelatinase-A); MMP-9 (92 kDa gelatinase, gelatinase-B). Finally, the membrane-bound MMPs are those that are attached to the outer cellular membrane. They include: The type-II transmembrane cysteine array MMP-23; the glycosyl phosphatidylinositol-attached MMPs 17 and 25 (MT4-MMP and MT6-MMP respectively); and the type-I transmembrane MMPs 14, 15, 16, 24 (MT1-MMP, MT2-MMP, MT3-MMP, and MT5-MMP respectively). All of these MMPs have a furin cleavage site in the pro-peptide, which is a feature also shared by MMP-11.

Thus, inhibiting the interaction of endosialin with an endosialin ligand inhibits the expression and/or activation of MMPs on the endosialin-expressing cell. In some preferred embodiments, the expression or activation of MMP-1, MMP-2, MMP-8, MMP-9, MMP-12, MMP-13, or MMP-18 is suppressed by the inhibition.

Without intending to be bound to any particular theory or mechanism of operation, it is believed that endosialin functions directly or indirectly in angiogenesis, particularly with respect to neovascularization and diseases such as cancer. Therefore, it is believed that disrupting the binding of endosialin or endosialin-expressing cells to endosialin ligands, or disrupting endosialin-mediated activation of integrins, expression of MMPs and/or cellular proliferation/survival can suppress vascularization associated with neovascular disease.

Accordingly, the invention also features methods for inhibiting angiogenesis. The methods can be carried out in vitro or in vivo. In one aspect, the methods for inhibiting angiogenesis comprise administering to a subject a therapeutically effective amount of a composition that obstructs endosialin expressed on the surface of a cell, wherein said obstruction inhibits the interaction of said cell with a ligand for endosialin, and wherein the inhibiting of said interaction of said cell with said ligand inhibits angiogenesis of a tissue, organ, or neoplasm in the subject.

In another aspect, the methods for inhibiting angiogenesis comprise contacting a cell, cell culture, tissue, or organ with a composition that obstructs endosialin expressed on the surface of a cell, wherein said obstruction inhibits the interaction of said cell with a ligand for endosialin, and wherein the inhibiting of said interaction of said cell with said ligand inhibits angiogenesis by said cell, cell culture, tissue, or organ.

In some preferred embodiments, the composition comprises at least one competitive inhibitor described herein. In some embodiments, the competitive inhibitors are endosialin ligands, for example, collagen, fibronectin, or endosialin-binding fragments thereof. Preferred competitive inhibitors are fragments of collagen I, collagen IV, or fibronectin. Most preferred competitive inhibitors are the 70 kDa N-terminal fragment of fibronectin, the 45 kDa gelatin binding fragment of fibronectin, and the 30 kDa heparin binding fragment of fibronectin.

In preferred embodiments, the composition comprises at least one antibody that specifically binds to endosialin. Such antibodies preferably have an affinity for endosialin that is less than about $1 \times 10^{-7}$ M, more preferably less than about $1 \times 10^{-8}$ M, more preferably less than about $1 \times 10^{-9}$ M, and more preferably less than about $1 \times 10^{-10}$ M. Antibodies that specifically bind to endosialin can include those antibodies whose characteristics are described and exemplified herein. For example, in some preferred aspects, the antibody that specifically binds to endosialin comprises a heavy chain comprising CDR1, CDR2, and CDR3 of SEQ ID NO:28, 30, and 32, respectively, and a light chain comprising CDR1, CDR2, and CDR3 of SEQ ID NO: 13, 15, and 17, respectively. In some embodiments, the heavy chain CDR1, CDR2, and CDR3 are encoded by nucleotide sequences of SEQ ID NO:27, 29, and 31, respectively. In some embodiments, the light chain CDR1, CDR2, and CDR3 are encoded by nucleotide sequences of SEQ ID NO:12, 14, and 16, respectively. In some embodiments, the antibodies can comprise a heavy chain comprising a variable domain of SEQ ID NO: 34 and a light chain comprising a variable domain of SEQ ID NO: 19. In some embodiments, the heavy chain variable domain is encoded by the nucleotide sequence of SEQ ID NO:33. In some embodiments, the light chain variable domain is encoded by the nucleotide sequence of SEQ ID NO:18. In some embodiments, the antibodies can comprise a heavy chain comprising the amino acid sequence of SEQ ID NO:22 or 26 and a light chain comprising the amino acid sequence of SEQ ID NO:11. In some embodiments, the heavy chain is encoded by the nucleotide sequence of SEQ ID NO:21 or 25 and the light chain is encoded by the nucleotide sequence of SEQ ID NO:10. In some embodiments, the antibodies comprise a heavy chain comprising SEQ ID NO:20 or 24 and a light chain comprising SEQ ID NO:9. In some embodiments, the antibodies comprise a heavy chain encoded by the nucleic acid sequence of SEQ ID NO:8 or 23. Antibodies can comprise a light chain encoded by the nucleic acid sequence that comprises SEQ ID NO:7. Antibody-producing cells producing antibodies that can be used in accordance with the invention have been placed with the Amer. Type Cult. Coll. (10801 University Blvd., Manassas, Va. 20110-2209) on Apr. 24, 2006 and on Mar. 11, 2008 and have been assigned Access. Nos. PTA-7554 and PTA-9017, respectively. The antibodies can be polyclonal, monoclonal, antigen-binding fragments, chimeric, humanized, fully human, and the like as described herein.

Inhibiting the expression of endosialin inhibits the interaction of endosialin with any endosialin ligand. Endosialin ligands include extracellular matrix proteins such as fibronectin and collagen.

The invention also features methods for inhibiting neovascularization. The methods can be carried out in vitro or in vivo. In one aspect, the methods for inhibiting neovascularization comprise administering to a subject a therapeutically effective amount of a composition that obstructs endosialin expressed on the surface of a cell, wherein said obstruction inhibits the interaction of said cell with a ligand for endosialin, and wherein the inhibiting of said interaction of said cell with said ligand inhibits neovascularization of a tissue, organ, or neoplasm in the subject.

In another aspect, the methods for inhibiting neovascularization comprise contacting a cell, cell culture, tissue, or organ with a composition that obstructs endosialin expressed on the surface of a cell, wherein said obstruction inhibits the interaction of said cell with a ligand for endosialin, and wherein the inhibiting of said interaction of said cell with said ligand inhibits neovascularization of said cell, cell culture, tissue, or organ.

In some preferred embodiments, the composition comprises at least one competitive inhibitor described herein. In some embodiments, the competitive inhibitors are endosialin ligands, for example, collagen, fibronectin, or endosialin-binding fragments thereof. Preferred competitive inhibitors are fragments of collagen I, collagen IV, or fibronectin. Most preferred competitive inhibitors are the 70 kDa N-terminal fragment of fibronectin, the 45 kDa gelatin binding fragment of fibronectin, and the 30 kDa heparin binding fragment of fibronectin.

In preferred embodiments, the composition comprises at least one antibody that specifically binds to endosialin. Such antibodies preferably have an affinity for endosialin that is less than about $1\times10^{-7}$ M, more preferably less than about $1\times10^{-8}$ M, more preferably less than about $1\times10^{-9}$ M, and more preferably less than about $1\times10^{-10}$ M. Antibodies that specifically bind to endosialin can include those antibodies whose characteristics are described and exemplified herein. For example, in some preferred aspects, the antibody that specifically binds to endosialin comprises a heavy chain comprising CDR1, CDR2, and CDR3 of SEQ ID NO:28, 30, and 32, respectively, and a light chain comprising CDR1, CDR2, and CDR3 of SEQ ID NO: 13, 15, and 17, respectively. In some embodiments, the heavy chain CDR1, CDR2, and CDR3 are encoded by nucleotide sequences of SEQ ID NO:27, 29, and 31, respectively. In some embodiments, the light chain CDR1, CDR2, and CDR3 are encoded by nucleotide sequences of SEQ ID NO:12, 14, and 16, respectively. In some embodiments, the antibodies can comprise a heavy chain comprising a variable domain of SEQ ID NO: 34 and a light chain comprising a variable domain of SEQ ID NO: 19. In some embodiments, the heavy chain variable domain is encoded by the nucleotide sequence of SEQ ID NO:33. In some embodiments, the light chain variable domain is encoded by the nucleotide sequence of SEQ ID NO:18. In some embodiments, the antibodies can comprise a heavy chain comprising the amino acid sequence of SEQ ID NO:22 or 26 and a light chain comprising the amino acid sequence of SEQ ID NO:11. In some embodiments, the heavy chain is encoded by the nucleotide sequence of SEQ ID NO:21 or 25 and the light chain is encoded by the nucleotide sequence of SEQ ID NO:10. In some embodiments, the antibodies comprise a heavy chain comprising SEQ ID NO:20 or 24 and a light chain comprising SEQ ID NO:9. In some embodiments, the antibodies comprise a heavy chain encoded by the nucleic acid sequence of SEQ ID NO:8 or 23. Antibodies can comprise a light chain encoded by the nucleic acid sequence that comprises SEQ ID NO:7. Antibody-producing cells producing antibodies that can be used in accordance with the invention have been placed with the Amer. Cult. Coll. (10801 University Blvd., Manassas, Va. 20110-2209) on Apr. 24, 2006 and Mar. 11, 2008 and have been assigned Access. No. PTA-7554 and Access. No. PTA-9017, respectively. The antibodies can be polyclonal, monoclonal, antigen-binding fragments, chimeric, humanized, fully human, and the like as described herein.

Inhibiting the expression of endosialin inhibits the interaction of endosialin with any endosialin ligand. Endosialin ligands include extracellular matrix proteins such as fibronectin, for example, human fibronectin (SEQ ID NO:35) and collagen.

The invention also features assays and methods for identifying agonists and antagonists of the interaction of endosialin with a ligand for endosialin. In some embodiments, the methods comprise contacting endosialin with a test compound, contacting the endosialin-test compound complex with a ligand for endosialin, and quantifiably measuring the interaction of endosialin with the ligand in the presence and in the absence of the test compound. An increase or decrease in the level of interaction of endosialin with ligand in the presence of the test compound indicates that the test compound is an agonist or antagonist, respectively, of the interaction of endosialin with the ligand.

In some embodiments, the methods comprise contacting an endosialin-expressing cell with a test compound, contacting the endosialin expressing cell with a ligand for endosialin, and quantifiably measuring the expression or activation of integrin molecules such as integrin $\beta1$, $\beta2$, or $\beta3$ on the cell in the presence and in the absence of the test compound. An increase or decrease in the level of expression or activation of the integrin molecules on the cell in the presence of the test compound indicates that the test compound is an agonist or antagonist, respectively, of the interaction of endosialin with said ligand.

In some embodiments, the methods comprise contacting an endosialin-expressing cell with a test compound, contacting the endosialin expressing cell with a ligand for endosialin, and quantifiably measuring the expression or activation of MMPs such as MMP-1, MMP-2, MMP-8, MMP-9, MMP-12, MMP-13, or MMP-18 on the cell in the presence and in the absence of the test compound. An increase or decrease in the level of expression or activation of the MMP molecules on the cell in the presence of the test compound indicates that the test compound is an agonist or antagonist, respectively, of the interaction of endosialin with said ligand.

In the inventive assays, the endosialin can be bound to a cell membrane, preferably a mammalian cell membrane, a cell membrane fragment, an artificial lipid bilayer, or to a suitable solid support. The endosialin ligand can be an extracellular matrix protein, including without limitation fibronectin or collagen.

One strategy for generating test compounds with potential biologic activity against endosialin or endosialin-expressing cells, i.e., potential interaction with endosialin, involves but is not limited to screening phage libraries producing phage coat peptides that can be screened to identify polypeptides in a library that can potentially serve to inhibit the interaction between endosialin and an endosialin ligand.

The following examples are provided to describe the invention in greater detail. They are intended to illustrate, not to limit, the invention.

Example 1

Immunohistochemistry Analysis of Endosialin Expression on Malignant Tissue

Use of antibodies to detect endosialin-expressing cells was shown by immunohistochemistry of malignant tissues. The anti-endosialin or normal IgG antibody was applied to freshly frozen human colorectal cancer tissues at two concentrations (0.5 µg/mL and 2.5 µg/mL). Phosphate-buffered saline [PBS (0.15M NaCl, pH 7.2)]+1% bovine serum albumin served as the diluent for the primary antibodies. Tissues were embedded in Tissue-Tek® O.C.T. medium, frozen on dry ice, and stored in sealed plastic bags below −70° C. Tissues were sectioned at approximately 5 µm, and fixed for 10 minutes in room temperature acetone. Slides were stored below −70° C. until staining Just prior to staining, slides were fixed for 10 seconds in 10% neutral-buffered formalin.

Figure 1B:

Cryosections were rinsed twice in phosphate-buffered saline (PBS [0.15M NaCl, pH 7.2]). Endogenous peroxidase was blocked by incubating the slides with the peroxidase solution provided in the Dako EnVision™ Kit for 5 minutes and rinsing twice in PBS (0.15M NaCl, pH 7.2). Next, the slides were treated with a protein block designed to reduce nonspecific binding for 20 minutes. The protein block was prepared as follows: PBS (0.15M NaCl, pH 7.2); 0.5% casein; 1% bovine serum albumin (BSA); and 1.5% normal goat serum. Following the protein block, the primary antibody (test article M4, negative control antibody, or none [buffer alone as the assay control]) was applied at room temperature for one hour. Next, the slides were rinsed two times with PBS (0.15M NaCl, pH 7.2), treated with the peroxidase-labeled goat anti-IgG polymer supplied in the Dako EnVision™ Kit for 30 minutes (EnVision™ polymer used at the concentration provided by manufacturer), rinsed two times with PBS (0.15M NaCl, pH 7.2), and treated with the substrate-chromogen (DAB) solution supplied in the Dako EnVision™ Kit for 8 minutes. All slides were rinsed in water, counterstained with hematoxylin, dehydrated and coverslipped for interpretation. As shown, vessels in the tumor (FIG. 1A) stained positive for endosialin while isotype control antibody stained serial section was negative (FIG. 1B).

Example 2

Immunohistochemistry Analysis of Endosialin Expression on Healthy Tissue

Figure 2A:
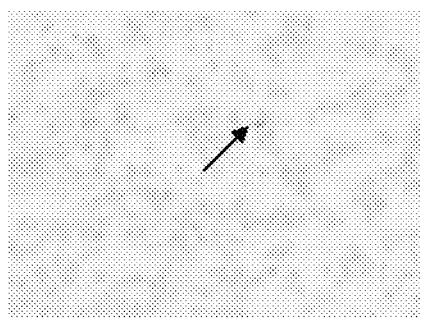
FIGS. 2A and 2B show immunohistochemical analysis of endosialin-positive cells of normal tissue. Normal tissues were isolated from patients by biopsy and flash frozen in liquid nitrogen. Samples were thin-sectioned and stained with anti-endosialin or isotype control antibody. As shown, normal tissue contained few EPCs (arrow, FIG. 2A) while isotype control antibody stained serial section were negative (FIG. 2B). Many normal tissues tested had a few EPCs as determined by in situ or antibody staining.
Figure 2B:
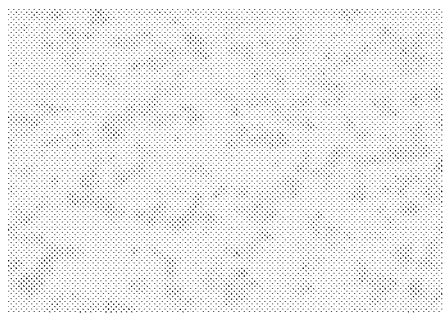

Use of antibodies to detect endosialin-expressing cells was shown by immunohistochemistry of normal tissues. Briefly, normal tissue specimens were sectioned by cryostat and analyzed for endosialin expression as described above. Normal tissues contained very few fibroblast/dendritic-like cells that expressed endosialin albeit not as robustly or homogenously as was observed in the vessels within tumors (FIGS. 2A and B). These cells are useful to study the effects of neovascularization and can be isolated for gene expression to study profiles of cell growth, differentiation, migration or signature identification. They can be studied in vivo, ex vivo or in vitro using methods known by those skilled in the art as well as those listed below.

Example 3

Isolation and Enrichment of Endosialin-Expressing Cells

To demonstrate that proteins that can bind to endosialin serve as an effective way to enrich for endothelial or fibroblast-like endosialin-expressing cells, Human Microvascular Endothelial Cells (HMVECs) were panned using an antibody that can bind to endosialin to isolate an enriched population of endosialin-expressing cells from a starting pool containing 5-10% endosialin-expressing cells. Not wanting to be bound by the method or specific reagents below, this example demonstrates the use of endosialin antibodies that can isolate endosialin expressing cells.

Briefly, 96-well plates were coated in sterile conditions with goat anti human IgG Fcγ. Next, 20 µg/ml of a human anti-endosialin antibody M4 was added to the plates and three wells (A, B, C) as controls without the antibody and incubated for 1 hr at 4° C. HMVECs were harvested from 10 cm petri dish cultures with DPBS/EDTA rather than trypsin to avoid any damage to the cell membranes, thereby leaving the endosialin cell surface proteins intact. Pooled cells were plated at two different concentrations, either 100,000 cells/well or 50,000 cells/well in the 96-well plates after aspirating and washing off any unbound anti-endosialin antibody. Cells were incubated in plates for one hour at 4° C. Plates were then washed with DPBS/FBS four times (until control wells A, B, and C showed no cells within the wells). The 50,000 cells/well plate showed very few cells while the 100,000 cells/well wells contained a number of cells attached to plate. Cells were then incubated for three days in appropriate growth media. The control B and C wells were picked from the 100,000 cells/well plates for immunostaining Calcein, AM dye was used to stain the cells for visualization using a Nikon® Eclipse TS100 Fluorescence Microscope. Positive panned cultures were expanded for growth and further analysis for homogeneous endosialin expression as described below.

To further determine the ability to isolate endosialin-expressing cells, anti-endosialin-antibody panned HMVEC cells and non-panned HMVEC cultures were prepared for immunostaining using a fluorescent anti-endosialin antibody or fluorescent α-β1-integrin antibody as control. As expected, greater than 90% of the cells stained positive for α-β1-integrin from panned and non-panned cultures (not shown), while greater than 90% of cells stained positive for endosialin from panned cultures while only 5-7% of cells stained positive for endosialin in unpanned HMVEC cultures. These data demonstrate the ability to isolate and enrich viable endosialin-expressing cells using endosialin-binding proteins such as antibodies.

Figure 3:
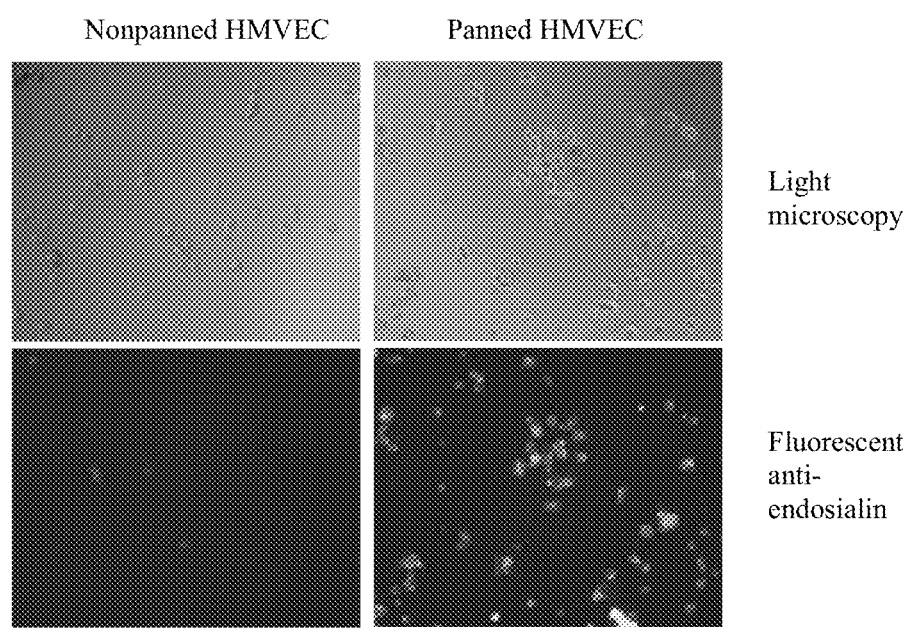
FIG. 3 shows isolation of endosialin-positive cells from primary endothelial cultures. HMVEC cultures were enriched for EPCs by panning Endosialin-panned cultures were then compared to HMVEC parental cultures for percentage of endosialin-expressing cells. As shown, the panned culture had a much higher number of endosialin-positive cells as compared to the non-panned parental culture as determined by immunostaining via anti-endosialin antibody followed by a fluorescent conjugated secondary antibody. Cell number of each field was determined by light microscopy.

As shown in FIG. 3, the panned culture had a much higher number of endosialin-positive cells as compared to the non-panned parental culture as determined by immunostaining via anti-endosialin antibody followed by a fluorescent conjugated secondary antibody. Cell number of each field was determined by light microscopy.

Example 4

Endosialin Interaction with Extracellular Matrix Proteins

Construction of TEM1 and Fc-TEM-1 Expression Plasmids.

PCR was used to amplify a DNA fragment representing amino acids 1-685 of the TEM1 open reading frame (GenBank #AF279142) from LA1-5S genomic DNA. The resulting amplicons were digested with EcoRI and XbaI and ligated into pEF6-V5-HisA (Invitrogen). To generate Fc-TEM-1, the extracellular region of TEM1 was fused to monomeric murine $IgG2_b$ $Fc_\gamma$ domain and ligated into the derivative pEF6-EK-Mm-IgG2b-Fcγ-ND vector which contains an enterokinase recognition region (DDDD) followed by a modified murine $IgG2_b$ $Fc_\gamma$ (hinge through CH3) domain. To prevent dimerization, the four cysteine residues responsible for inter-heavy chain disulfide bonding were changed to serine. The resulting monomeric, secreted fusion protein consists of the full-length TEM1 extracellular domain and the murine $IgG2_b$ $Fc_\gamma$. The integrity of all plasmid sequences was verified using Beckman® DTCS chemistry (Beckman Coulter, Fullerton, Calif.). Raw data were acquired with a CEQ 8000 DNA sequencer and analyzed using Vector NTI® software (Invitrogen).

Purification of Fc-TEM-1.

CHO-TEM1-Fcγ cells were cultured at 25 L scale in IS-CHO-CD medium (Irvine Scientific, Santa Ana, Calif.), supplemented with 2 mM L-glutamine, 1× Penicillin/Streptomycin, 6 g/L soybean hydrolysate and 2.2 g/L sodium bicarbonate (Irvine Scientific), on a Wave20/50EH platform fitted with a Cellbag50® (GE Healthcare, Piscataway, N.J.), until the viability of the culture reached 50-70%. Conditioned extra-cellular medium was clarified using a Flexstand® Benchtop Pilot Hollow Fiber System (GE Healthcare) equipped with a 0.2 μm hollow fiber cartridge (GE Healthcare) until 0.5 L of culture remained in the holding vessel. At this point, the concentrated cell mass was washed with 4 L of phosphate-buffered saline (PBS, 20 mM K Phosphate, 150 mM NaCl pH 7.2), to recover remaining extra-cellular fluid. The 4 L wash was pooled with the clarified feedstock. The clarified culture medium was then concentrated twelve-fold (29 L to 2.5 L); using a Prep/Scale® Spiral Wound 2.5 ft$^2$ 100 k ultrafiltration cartridge set in a Prep/Scale® holder (Millipore, Billerica, Mass.), and driven by a peristaltic pump at an inlet pressure of 20 PSI, and a recirculation rate of approximately 400 mL/min. The resulting concentrated feedstock was filter-sterilized through bottle top filters equipped with a 0.2 μm membrane (Nalgene). TEM1-Fcγ was captured by protein A affinity chromatography, over a 10×100 mm ProSep-vA® (Millipore) column, and eluted by addition of 5 column volumes of elution buffer (100 mM citrate/10 mM acetate pH 3.0). Eluted material was dialyzed against buffer QA (20 mM Tris-Cl pH 8.0), and further purified by ion-exchange chromatography over a 5 mL HiTrap® Q-FF column (GE Healthcare). Bound proteins were washed with 15% buffer QB (20 mM Tris-Cl, 1 M NaCl pH 8.0), followed by elution of bound Fc-TEM-1 using 35% buffer QB. Eluted proteins were concentrated by ultra-filtration in a Model 8400 positive pressure ultra-filtration module (Millipore) fitted with a 100 kDa MWCO membrane (Millipore), to a final volume of approximately 5 mL. Concentrated Fc-TEM-1 was purified by preparative size exclusion chromatography on a Sephacryl® S-300HR 26×60 column (GE Healthcare), equilibrated with PBS. Fractions containing purified Fc-TEM-1 were pooled, concentrated to a nominal range between 0.1-1 mg/mL by ultra-filtration using a 100 kDa MWCO membrane and stored in single-use aliquots at −80° C.

Purified Fc-TEM-1 (2.9 μg) was loaded onto a 4-12% Bis-Tris gel (Invitrogen, Inc.), and electrophoresed in MOPS Running Buffer (50 mM MOPS, 50 mM Tris, 3.5 mM SDS, 1 mM EDTA pH 7.7), for 40 minutes. For staining, the gel was fixed for 15 minutes in Fix solution (50% methanol, 10% acetic acid), washed twice for 10 minutes in deionized water, and stained for at least one hour using GelCode Blue colloidal Coomassie Blue stain (Pierce). The gel was de-stained by repeated washing with deionized water.

Pre-coated Fibronectin (FN), Collagen I (Col I), Collagen IV (Col IV), Laminin (LN) (BD Biosciences, San Diego Calif.), Vitronectin (VN), or Gelatin (Gel) (Chemicon Intl.) 96-well plates were used to assess Fc-TEM-1 binding. The binding of TEM1 to Col I, Col IV, and FN was not due to trace contaminants in the purified protein from human plasma since neither Col I nor Col IV was detected in FN by anti-Col antibody ELISA, nor was FN detected in Col (data not shown). All plates were blocked with assay buffer (0.5% BSA, 0.5% Tween-20 in PBS) for 2 h prior to the addition of Fc-TEM-1 fusion protein, a soluble endosialin generated by fusion of the N-terminal leader sequence and the entire extracellular domain of endosialin to a murine gamma heavy chain. Following 1 h incubation at room temperature, the plates were washed and the HRP-goat anti-human IgG (H+L) antibody (Jackson Immunoresearch Laboratories, West Grove, Pa.) was added for 1 h. Color development was assessed using the SureBlue™ TMB Peroxidase Substrate (KPL, Gaithersburg, Md.). Both BSA and a human isotype control antibody were used as negative controls. Fc-TEM-1 did not bind BSA, nor did the human isotype bind any of the ECM proteins (data not shown).

Figure 4A:
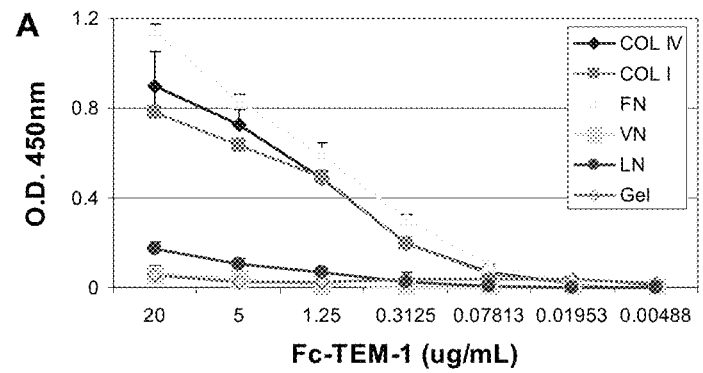
As shown in FIG. 4A, the Fc-TEM1 bound to FN and COL robustly while weak binding was observed with LM, VN, or Gel. For FIG. 4B, an ELISA plate was pre-coated overnight with the following antigens: *Staphylococcus* enterotoxin B (STEB), ovalbumin (OVA), bovine gamma globulin (BGG), tumor-associated 90-kD glycoprotein antigen expressed on most melanoma cells (TA90), hen egg lysozyme (HEL), tetanus toxoid (TT), 1% BSA, human mesothelin, human GM-CSF, goat IgG, and mouse IgG. Fc-TEM1 was added at increasing amounts (5, 10, 50 ug/ml) and allowed to adhere for 2 hours. Plates were then washed and HRP-conjugated goat-anti-mouse antibody was added to detect bound Fc-TEM1.

As shown in FIG. 4A, the Fc-TEM1 bound to fibronectin and collagen I and IV in a dose dependent manner while no binding was observed within the entire dose range to LN or VN. Interestingly, while Fc-TEM1 bound collagen, no detectable binding to gelatin (heat-denatured collagen) was observed. None of four murine isotype IgG antibodies tested could bind to any of the ECM proteins, ruling out the possibility that the interactions were mediated by murine Fc backbone of the Fc-TEM1 fusion protein (data not shown). A fusion protein containing the murine gamma heavy chain and only the lectin domain of endosialin also binds FN (data not shown).

Figure 4B:
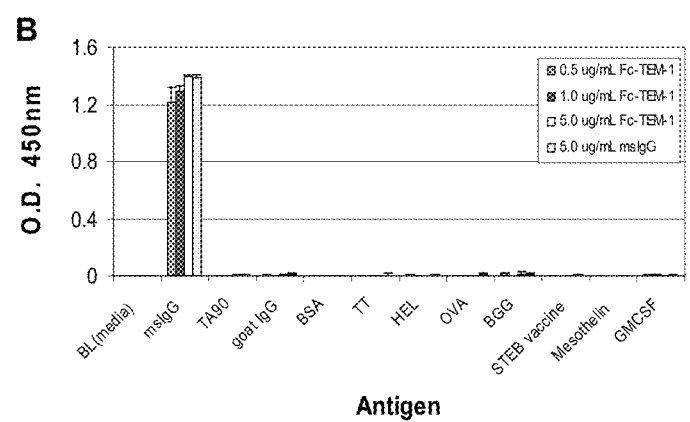
FIG. 4 shows that recombinant endosialin (Fc-TEM1) binds to extracellular matrix proteins (EMPs). ELISA plates, precoated with EMP fibronectin (FN), collagen (COL; including collagen type I (COLI) and collagen type IV (COL IV)), vitronectin (VN), laminin (LN), or gelatin (Gel), were blocked with ELISA assay buffer prior to addition of purified Fc-TEM1 protein at increasing concentrations. Following a two hour incubation, the plates were washed and assayed for binding using a HRP-linked goat-anti-mouse secondary mAb specific for the Fc tail using standard ELISA conditions. Plates were washed and developed and then assayed using a plate reader at OD 450 nm.
Figure 5:
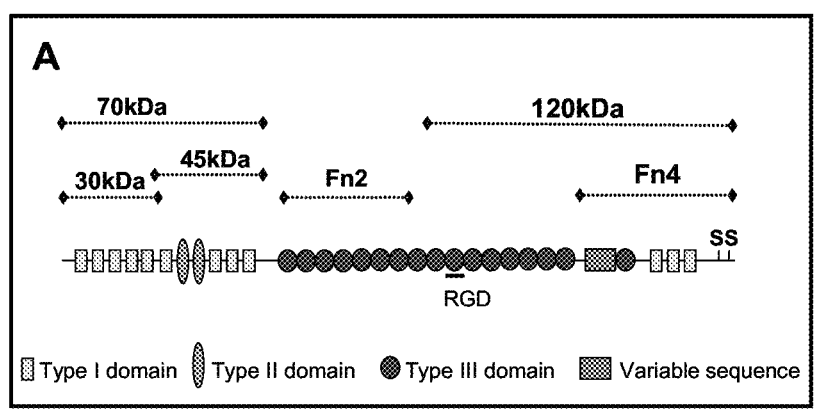
FIG. 5 shows mapping of fibronectin (FN) binding domains to endosialin. Proteolytic and recombinant fragments derived from fibronectin (FN) were assessed for the ability to support TEM-1 binding. FN fragments evaluated include: the N-terminal 70 kDa fragment (Sigma Cat. No. F0287) (obtained by cathepsin D digestion of fibronectin); the 30 kDa heparin binding fragment (Sigma Cat. No. F9911); the 45 kDa gelatin binding fragment (Sigma Cat. No. F0162) (both obtained from trypsin digestion of the 70 kDa fragment); the 120 kDa fragment containing the cell attachment domain ("the 120 kDa fragment"); and two recombinant fragments: Fn2, which contains the first 7 FN type III domains, and Fn4, which contains the site of interchain disulfide bonds and $\alpha 4\beta 1$ integrin binding domain. The diagram of FN structure was adapted from Wierzbicka-Patynowski et al. (2003) *J. Cell Sci.*, 116:3269-76.

To confirm selectivity of the Fc-TEM1 and ECM protein interaction, Fc-TEM1 was applied to ELISA plates coated with different purified proteins. Antigen-specific ELISAs were performed by coating TP Immunomini ELISA plates with 1 ug/ml STEB (Staphylococcus enterotoxin B vaccine), 2 ug/ml bovine gamma globulin, 2 ug/ml tumor-associated 90 kD glycoprotein antigen expressed on most melanoma cells (TA90), 2 ug/ml hen egg lysozyme, 1:500 dilution of tetanus toxoid, 1% BSA, 0.2 ug/ml human mesothelin, 2 ug/ml ovalbumin (OVA), 1 ug/ml human GM-CSF, 2 ug/ml goat IgG, 2 ug/ml mouse IgG dissolved in bicarbonate coating buffer (pH 9.6) (Sigma) overnight at 4° C. The plates were washed three times with washing buffer (containing 0.5% TWEEN-20) blocked with 1× assay buffer for 2 hours at room temperature and ELISA was performed as described above. As shown in FIG. 4B, Fc-TEM1 did not bind to any of the proteins tested except for the anti-mouse Fc used as a positive control.

Example 5

Figure 6:
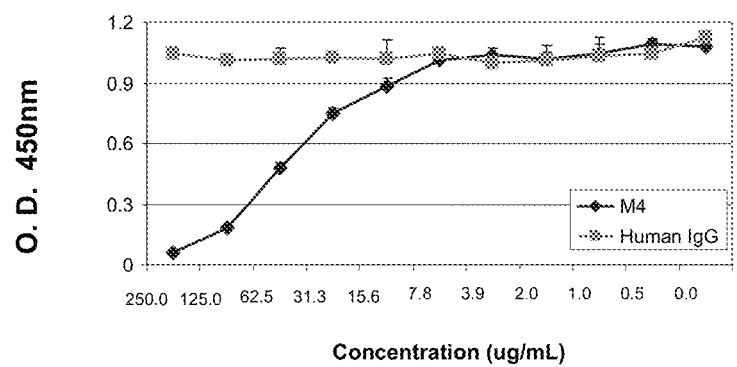
FIG. 6 shows recombinant Fc-TEM1 binding to EMP and fibronectin in the presence of inhibitors. M4 is a humanized antibody to human endosialin, while rbtTEM1 is a rabbit antibody to human endosialin. The assay was performed as described in FIG. 4, except that antibodies were added to measure the ability to perturb or block Fc-TEM1 to bind to FN. As shown in this figure, M4 was able to inhibit Fc-TEM1 binding to FN while a non-specific control (HuIgG) was not.

Inhibition of TEM1 Binding to Human Plasma Fibronectin 96-well plates were pre-coated with Fibronectin (FN), and the ability of anti-TEM-1 antibodies to block Fc-TEM-1 mediated adhesion was assessed by ELISA. Briefly, the FN-coated plate was blocked with assay buffer (0.5% BSA, 0.5% Tween-20 in PBS) for 2 h prior to the addition of fusion proteins. Fc-TEM-1 was pre-incubated for 1 h at 4° C. with the antibodies M4 (a humanized anti-endosialin antibody described as ES1 in U.S. Pat. Publication No. 20060239911), human isotype (HuIgG), or anti-TEM-1 antibody raised in rabbits (RbtTEM1). M4 does not bind to species homologs of endosialin with the exception of nonhuman primates. The binding epitope for M4 has been mapped to the extracellular lectin domain of endosialin. The protein/antibody complex was added to the FN-coated plate and allowed to adhere for 1 h at room temperature at which time the plates were washed and the HRP-goat anti-human IgG (H+L) antibody (Jackson Immunoresearch Laboratories, West Grove, Pa.) was added for 1 h. Color development was assessed using the SureBlue™ TMB Peroxidase Substrate (KPL, Gaithersburg, Md.). As shown in FIG. 6, M4 suppressed Fc-TEM1 binding to fibronectin, whereas a non-specific control (HuIgG) did not suppress binding. RbtTEM1 also suppressed Fc-TEM1 binding to fibronectin (data not shown).

Example 6

Endosialin Mediates Adhesion to Fibronectin

CHO-TEM1 cells stably expressing endosialin (verified by FACS with M4 antibody; data not shown) were generated. CHO-K1 cells were maintained in RPMI supplemented with L-glutamine, 1% minimal essential amino acids, Sodium pyruvate, Non-Essential amino acids, and 10% heat-inactivated FBS (Invitrogen, Carlsbad, Calif.). CHO-K1 cells (3E6) (ATCC, Manassas, Va.) were electroporated with 10 ug linearized plasmid DNA in a 0.4 mm electroporation cuvette. A pulse of 170V/1000 uF was delivered using a GENE PULSER (BioRad, Hercules, Calif.). Electroporated cells were allowed to recover for 24 hours after which Blasticidin (5 ug/ml)-resistant clones were selected. Endosialin expression was verified by FACS and cells were sorted for high expression.

Figure 9A:
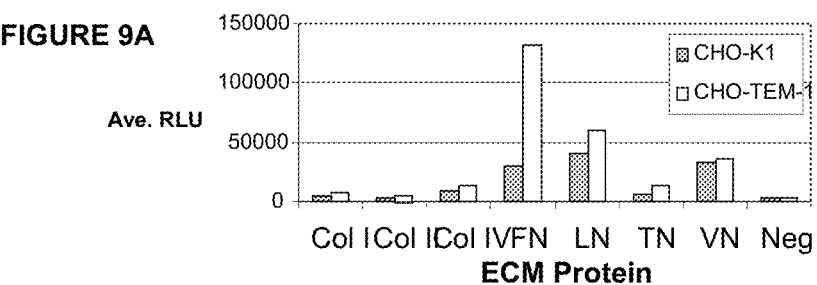
As shown in FIG. 9A, the number of adherent CHO-TEM1 cells was 6-fold higher than the number of parental CHO-K1 cells in wells coated with FN. No significant differences in adhesion between CHO-K1 and CHO-TEM1 on surfaces coated with laminin or vitronectin were observed, while adhesion to collagens and tenascin was too weak to assess any valuable differences (FIG. 9A). Pretreatment of CHO-TEM1 cells with M4 antibody resulted in 50% reduction of TEM1-FN-dependent cell adhesion, while IgG control antibody had no effect (FIG. 9B). M4 antibody treatment did not affect FN-dependent, endosialin-independent cell adhesion (baseline adhesion) of parental CHO-K1 cells. CHO-TEM1 cells showed a 3- to 5-fold increased adhesion to FN, 70 kDa, and 30 kDa fragments compared to parental CHO-K1 cells, whereas no significant adhesion was seen to 45 kDa or Fn2 fragments. CHO-TEM1 cells bound MATRIGEL five times better than CHO-K1 (FIG. 9C).
Figure 9B:
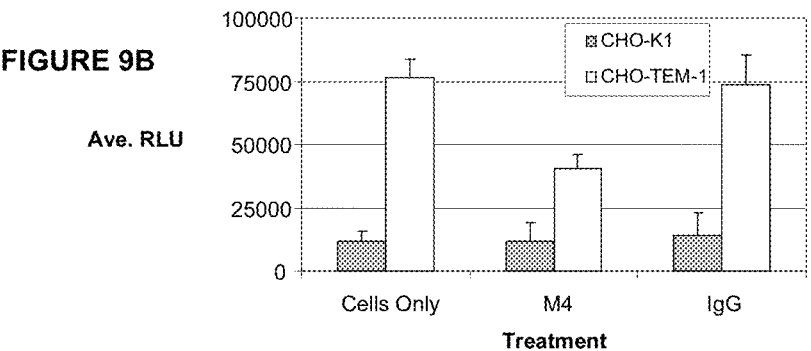
FIG. 9B demonstrates that anti-endosialin antibody M4 reduces endosialin-mediated cell adhesion to FN. Cells (1.5E5) were preincubated for 1 hour at 4° C. with antibody M4 (100 ug/ml) or an IgG isotype control antibody (100 ug/ml). For FIG. 9C, cells were tested for the ability to bind full length FN or fibronectin fragments.

Cells ($1.5 \times 10^5$ cells/well) were washed and suspended in PBS containing $Mg^{2+}/Ca^{2+}$, and added in quadruplicate to a 96-well-plate coated with Fibronectin and allowed to adhere for 1 h. Where indicated, cells were pre-incubated with antibody (100 ug/mL) M4 or human isotype (IgG) for 1 h prior to the start of the assays. After the cells were allowed to adhere the plate was washed 5 times with PBS and viability was measured using CellTiter-Glo® (Promega, Madison, Wis.). FIG. 9B shows that over-expression of endosialin results in increased cell binding to fibronectin, which can be blocked by endosialin inhibitors such as antibody M4, in contrast to controls such as nonspecific IgG.

Example 7

Endosialin Binding to Fibronectin and Fibronectin Fragments

Fibronectin is a large complex glycoprotein that exists as a dimer covalently linked by a disulfide bridge at the C-terminus of the protein (Ruoslahti et al. (1981) *J. Biol. Chem.*, 256:7277-7281; Wierzbicka-Patynowski & Schwarzbauer (2003) *J. Cell Sci.*, 116:3269-3276; Magnusson & Mosher (1998) *Arterioscler. Thromb. Vasc. Biol.*, 18:1363-1370). Fibronectin fragments either derived from enzymatic degradation or alternative splicing have been reported to be associated with certain disease states and possess distinct biological functions (Magnusson & Mosher (1998) *Arterioscler. Thromb. Vasc. Biol.*, 18:1363-1370; Labat-Robert (2002) *Semin. Cancer Biol.*, 12:187-195; Homandberg (1999) *Front Biosci.*, 4:D713-730).

The ability of Fc-TEM-1 to bind to different fibronectin fragments was assessed. Equimolar amounts of proteins were diluted in coating buffer (50 mM Carbonate-bicarbonate, pH9.4), added to an ELISA plate (Greiner Bio-one, Monroe, N.C.) and incubated overnight at 4° C. All plates were blocked with assay buffer (0.5% BSA, 0.5% Tween-20 in PBS) for 2 h prior to the addition of Fc-TEM-1. Following 1 h incubation at room temperature, the plates were washed and the HRP-goat anti-human IgG (H+L) antibody (Jackson Immunoresearch Laboratories, West Grove, Pa.) was added for 1 h. Color development was assessed using the SureBlue™ TMB Peroxidase Substrate (KPL, Gaithersburg, Md.). To assess the integrity of coated fibronectin proteins, the rabbit polyclonal antibody directed against fibronectin (FN Ab) was used to detect that all FN fragments were recognizable and coated evenly.

The full length human plasma purified Fibronectin and 120 kDa cell attachment FN-fragment proteins were purchased from Chemicon Intl. (Temucula, Calif.), proteolytic 30 kDa, 45 kDa, 70 kDa fragments from Sigma (St. Louis, Mo.), and the recombinant human fibronectin fragments 2 and 4 (FN2 and FN4, respectively) from R&D Systems (Minneapolis, Minn.).

Figure 7A:
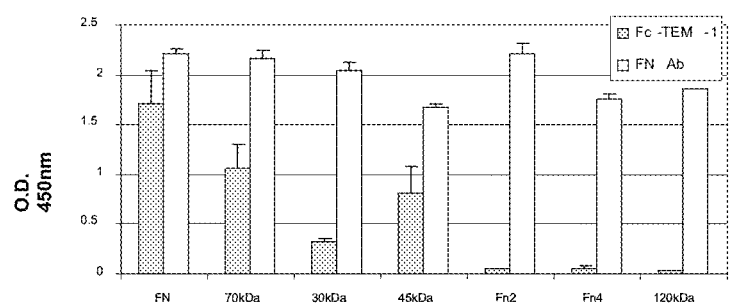
FIG. 7A shows binding to protein fragments derived from native FN.
Figure 7B:
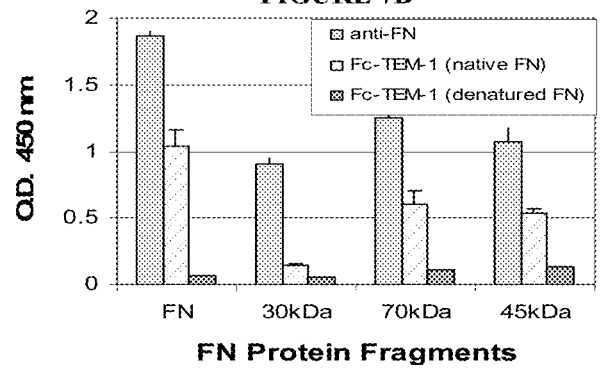
FIG. 7B shows binding to protein fragments derived from denatured FN. For FIGS. 7A and 7B, FN fragment was coated on an ELISA plate at the indicated concentrations. An anti-FN polyclonal antibody followed by addition of HRP-conjugated goat-anti-rabbit secondary antibody was used to detect intact bound proteins. Fc-TEM1 (1.25 ug/ml) was added and allowed to bind for 2 hours. Plates were then washed and HRP-conjugated goat-anti-mouse antibody was added to detect bound Fc-TEM1. The hatched bar (Fc-TEM1-native) in FIG. 7B represents Fc-TEM1 binding to nondenatured FN. As shown, endosialin binds to the N-terminal region of fibronectin, as little or no binding was detected for binding to fragments FN-2, FN-4, or 120 kDa. Polyclonal antibodies to fibronectin bound to all fragments.
Figure 7C:
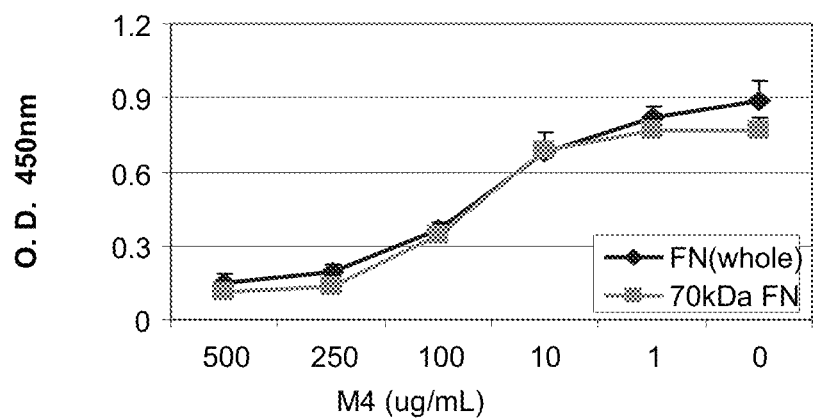
FIGS. 7C and 7D show binding of Fc-TEM1 to the 70 kDa fragment of FN and inhibition of the interaction by endosialin-EMP inhibitor compounds. Whole FN and the 70 kDa FN protein were coated onto an ELISA plate at a fixed concentration of ~15 nmol/well for both proteins. Fc-TEM1 (1.25 ug/ml) was pre-incubated at 4° C. for 1 hour with increasing amounts of anti-endosialin antibody M4 or isotype control IgG. Fc-TEM1/M4 (FIG. 7C) or Fc-TEM1/IgG (FIG. 7D) complexes were added to FN- and 70 kDa-coated wells and incubated for 2 hours at room temperature. Bound Fc-TEM1 protein was detected by the addition of HRP-conjugated goat-anti-mouse secondary antibody.
Figure 7D:
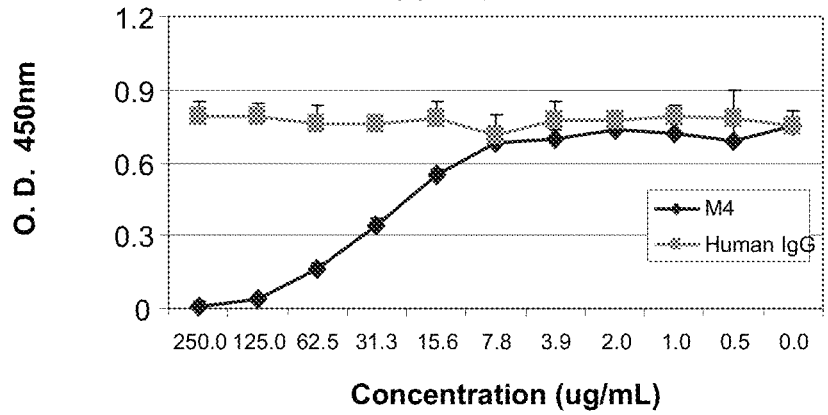

As shown in FIG. 7A, Fc-TEM1 binds the amino terminal 70 kDa fragment of FN and its proteolytic cleavage products (45 kDa and 30 kDa fragments). The extent of binding varied among the different fragments and was less than that seen with whole FN. In contrast, Fc-TEM1 did not bind the 120 kDa FN fragment or the recombinant fragments Fn2 or Fn4. This lack of binding was unlikely due to uneven coating or degradation since all FN fragments were strongly detected by an anti-FN polyclonal antibody. This is evidence that the FN domain involved in interaction with endosialin resides within the 70 kDa amino terminal portion. To determine whether the reduced binding capacity upon further digestion of the 70 kDa fragment indicates that Fc-TEM1 binds to a region located in close proximity to the proteolytic cleavage site or that TEM1 recognizes conformationally dependent epitopes within the amino terminus of FN that is altered after further digestion, the ability of Fc-TEM1 to bind reduced forms of FN proteins was examined. While anti-FN antibody was able to recognize reduced FN, indicating equivalent coating, the binding of Fc-TEM1 was completely ablated as shown in FIG. 7B. Similar to whole FN, anti-endosialin antibody M4 blocked Fc-TEM1 binding to the 70 kDa fragment in a dose-dependent manner (FIG. 7C), while an isotype control antibody had no effect (FIG. 7D). These results indicate that Fc-TEM1 recognizes conformationally dependent epitopes located within the amino terminus of FN that can be impaired upon further proteolytic degradation.

Example 8

Association of Cell Surface Fibronectin with Endosialin

CHO-TEM1 cells stably expressing endosialin (verified by FACS with M4 antibody; data not shown) were generated. CHO-K1 cells were maintained in RPMI supplemented with L-glutamine, 1% minimal essential amino acids, Sodium pyruvate, Non-Essential amino acids, and 10% heat-inactivated FBS (Invitrogen, Carlsbad, Calif.). CHO-K1 cells (3E6) (ATCC, Manassas, Va.) were electroporated with 10 ug linearized plasmid DNA in a 0.4 mm electroporation cuvette. A pulse of 170V/1000 uF was delivered using a GENE PULSER (BioRad, Hercules, Calif.). Electroporated cells were allowed to recover for 24 hours after which Blasticidin (5 ug/ml)-resistant clones were selected. Endosialin expression was verified by FACS and cells were sorted for high expression.

The level of cell surface FN was examined by flow cytometry in parental CHO-K1 and CHO-TEM1 cells using a polyclonal anti-FN antibody. Cells were harvested in Cell Dissociation Buffer (Invitrogen, Carlsbad, Calif.), washed, and resuspended in ice-cold PBS+1% FBS. Cells were incubated for 1 hour on ice with primary antibody, M4 (10 ug/ml), washed, and incubated with FITC-conjugated goat-anti-human secondary antibody (Southern Biotech, Birmingham, Ala.) and analyzed on an EASYCYTE Flow Cytometer (Guava Technologies, Hayward, Calif.). 15-20% higher levels of surface FN in CHO-TEM1 cells compared to CHO-K1 cells were observed constantly (data not shown). Association of cell surface FN with endosialin was examined.

Using an anti-FN antibody, FN was immunoprecipitated from both CHO-K1 and CHO-TEM1 lysates, followed by Western blot using the same antibody or an anti-TEM1 antibody (M4). Cells (10E7) were lysed in radioimmunoprecipiation (RIPA) buffer (50 mM Tris-HCl, pH 7.4, 1% NP-40, 0.5% sodium deoxycholate, 150 mM NaCl, 0.1% sodium dodecyl sulfate [SDS]) supplemented with Complete Mini Protease Inhibitor Cocktail (Roche Diagnostics, Indianapolis, Ind.) and centrifuged at 13,000 rpm for 15 min to remove debris. Protein G Sepharose 6 Fast Flow Beads (Amersham Biosciences, Piscataway, N.J.) were washed 3 times with PBS and anti-FN antibody (1 ug) was captured by gentle rocking at 4° C. Equal amounts of protein per sample were pre-cleared by the addition of unbound Protein G. After 2 hours of incubation, the Protein G was removed and the supernatant was added to the antibody-Sepharose complex and incubated overnight at 4° C. After extensive washing with RIPA buffer, the bound protein was removed by boiling for 10 minutes in NuPAGE® LDS sample buffer (Invitrogen) containing 5% β-mercaptoethanol. Proteins were separated using SDS-polyacrylamide gel electrophoresis on a 4-12% Bis-Tris gel (Invitrogen) and transferred to PVDF membrane. Immunoblotting was conducted using rabbit polyclonal antibodies specific for fibronectin (Abcam, Cambridge, Mass.) or endosialin (Morphotek, Inc., Exton, Pa.), detected with a goat-anti-rabbit HRP-conjugated antibody, and visualized using SUPERSIGNAL West Pico chemiluminescent substrate (Pierce, Rockford, Ill.). The integrity and purity of soluble Fc-TEM1 was also monitored by Western blot. Protein (5 ug) was boiled for 5 min in 4× NUPAGE LDS Sample Buffer (Invitrogen) containing 5% β-mercaptoethanol, subjected to electrophoresis on a NUPAGE 4-12% Bis-Tris gel (Invitrogen), and transferred to PVDF membrane and immunoblotting was performed as described above.

It was found that FN can immunoprecipitate endosialin from CHO-TEM1 lysates (data not shown). In contrast, in cell lysates immunoprecipitated with a normal IgG that did not pull down FN, no endosialin could be detected (data not shown). At least two different approaches (ELISA and coimmunoprecipitation) provide strong evidence of FN and endosialin interaction. Similar results were obtained using HEK-293T cells ectopically expressing endosialin (data not shown).

Example 9

Cells Expressing Endosialin Cultured on MATRIGEL Form Web-Like Structures

Figure 8:
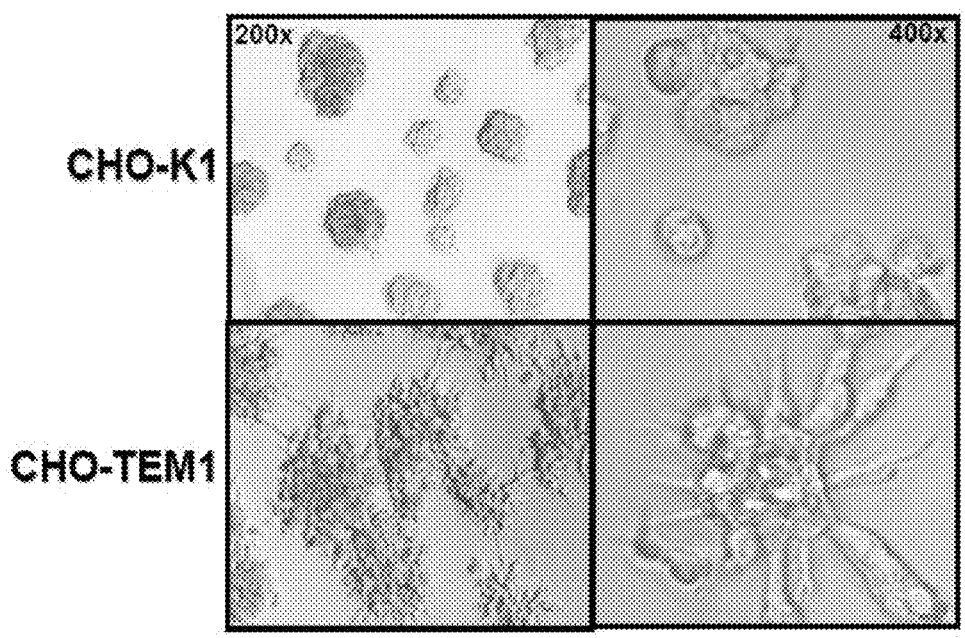
FIG. 8 illustrates a change in cell morphology on a gelatinous protein mixture sold under the trade name MATRIGEL (BD Biosciences) upon expression of endosialin. 8E4 cells of either CHO-K1 or CHO-TEM1 were seeded onto a 96-well-plate coated with MATRIGEL and incubated at 37° C. Following overnight incubation, the cells were photographed for macroscopic examination of tubule formation.

While no differences in growth or survival were observed between parental CHO-K1 and CHO-TEM1 cells cultured on plastic surface, a drastically different morphology was observed when these cells were cultured on MATRIGEL. Parental CHO-K1 cells grew into isolated cell clusters with minimal protrusions after 2 days of culturing (FIG. 8, top panels), while CHO-TEM1 cells grew into clusters forming a web-like network (FIG. 8, bottom left panel). In addition, CHO-TEM1 cells within the cluster exhibited protrusions reaching out to other clusters (FIG. 8, bottom right panel). Over time, CHO-TEM1 cells but not CHO-K1 cells moved closer to each other to form larger clusters (data not shown).

Example 10

Endosialin Expression Increases Cell Adhesion to Fibronectin, and the 70 kD or 30 kD N-Terminus of Fibronectin To assess adhesion to FN fragments, equimolar amounts of protein fragments were pre-coated overnight and then blocked for 2 h with PBS containing 10 mg/mL BSA. MATRIGEL served as a positive control. CHO-K1 or CHO-TEM1 cells ($1.5 \times 10^5$ cells/well) harvested in cell dissociation buffer were washed and suspended in PBS containing $Mg^{2+}$/$Ca^{2+}$, and added in quadruplicate to an ECM Cell Adhesion Array Kit (Millipore) or plated on individually coated FN, LN, Gel, and Col I plates (BD Biosciences) and allowed to adhere for 1 h. Following incubation, each well was washed 5 times with PBS and viability was measured using CellTiter-Glo®. Where indicated, cells were pre-incubated with antibody for 1 hour prior to the start of the assay. As shown in FIG. 9A, the number of adherent CHO-TEM1 cells was 6-fold higher than the number of parental CHO-K1 cells in wells coated with FN. No significant differences in adhesion between CHO-K1 and CHO-TEM1 on surfaces coated with laminin or vitronectin were observed, while adhesion to collagens and tenascin was too weak to assess any valuable differences (FIG. 9A). Pretreatment of CHO-TEM1 cells with M4 antibody resulted in 50% reduction of TEM1-FNdependent cell adhesion, while IgG control antibody had no effect (FIG. 9B). M4 antibody treatment did not affect FN-dependent, endosialin-independent cell adhesion (baseline adhesion) of parental CHO-K1 cells.

Figure 9C:
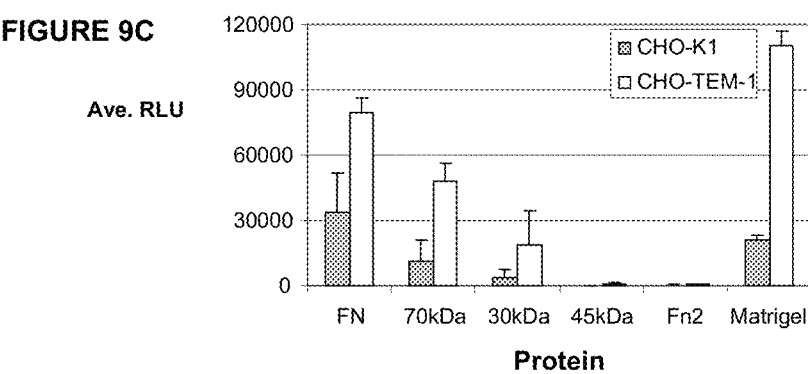
FIG. 9 shows endosialin-mediated cellular binding to EMP fragments. CHO cells were transfected with a vector expressing endosialin or mock cDNA. Cells were confirmed to express cell surface endosialin (CHOTEM1) while those transfected with mock (CHOK1) did not. For FIG. 9A, Chinese Hamster Ovary (CHO) cells were added to a pre-coated 96-well plate containing various ECM proteins. The cells were allowed to adhere for 1 hour at 37° C. and wells were washed extensively to remove any loosely bound cells. The number of attached cells was determined using the CELLTITER-GLO Luminescent Cell Viability Assay. Abbreviations: Col, Collagen; FN, fibronectin; LN, laminin; TN, tenascin; VN, vitronectin; Neg, bovine serum albumin. For FIG. 9B, Chinese Hamster Ovary (CHO) cells were transfected with a vector expressing endosialin or mock cDNA. Cells were confirmed by FACS analysis to express cell surface endosialin (CHOTEM1) while those transfected with mock (CHOK1) did not. Cells were then tested for the ability to bind EMP fibronectin alone or in combination with anti-endosialin antibody M4 or control IgG.

Plates were precoated with equimolar amounts of whole FN, FN proteolytic fragments, and MATRIGEL. CHO-TEM1 cells showed a 3- to 5-fold increased adhesion to FN, 70 kDa, and 30 kDa fragments compared to parental CHO-K1 cells, whereas no significant adhesion was seen to 45 kDa or Fn2 fragments. CHO-TEM1 cells bound MATRIGEL five times better than CHO-K1 (FIG. 9C). These data indicate that endosialin enhances the adhesion of cells to extracellular matrices and that the amino terminus of FN is involved with these interactions.

Example 11

Endosialin Binds to Collagen I and M4 Inhibits this Binding

Figure 10:
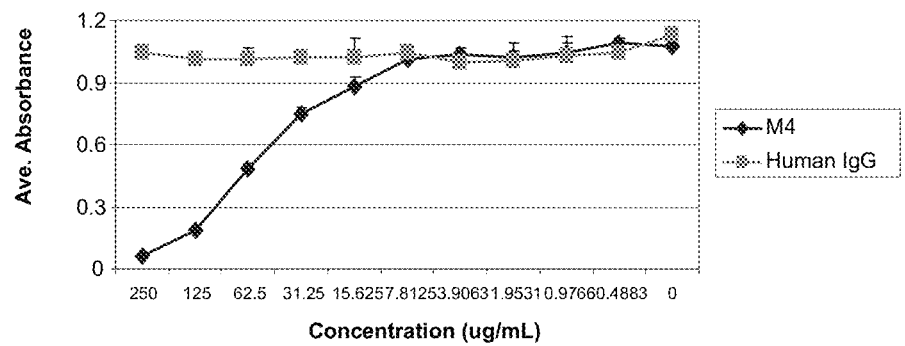
FIG. 10 shows identification of endosialin-EMP collagen inhibitor compounds. CHO cells were transfected with a vector expressing endosialin or mock cDNA. Cells were confirmed to express cell surface endosialin (CHOTEM1) while those transfected with mock (CHOK1) did not. Cells were then tested for the ability to bind EMP Collagen Type I (COL I) alone or in combination with anti-endosialin antibody M4 or control IgG. As shown, over-expression of endosialin results in increased cell binding to COL I which can be blocked by endosialin inhibitors such as M4 in contrast to control molecule (IgG). RbtTEM1 also suppressed Fc-TEM1 binding to COL I (data not shown).

A 96-well plate pre-coated with Collagen I was used to assess M4 ability to block Fc-TEM-1 binding. The plate was blocked with assay buffer (0.5% BSA, 0.5% Tween-20 in PBS) for 2 h prior to the addition of protein at the indicated concentration (μg/mL). Fc-TEM-1 was pre-incubated for 1 h at 4 C with the antibodies M4 or human isotype (Human IgG). The protein/antibody complex was then added to the Col I-coated plate and allowed to adhere for 1 h at room temperature at which time the plates were washed and the HRP-goat anti-human IgG (H+L) antibody (Jackson Immunoresearch Laboratories, West Grove, Pa.) was added for 1 h. Color development was assessed using the SureBlue™ TMB Peroxidase Substrate (KPL, Gaithersburg, Md.). As shown in FIG. 10, over-expression of endosialin results in increased cell binding to COL I, which can be blocked by endosialin inhibitors such as M4, in contrast to controls such as nonspecific IgG. RbtTEM1 also suppressed Fc-TEM1 binding to Col I (data not shown).

Example 12

Endosialin Increases Cell Adhesion to Collagen

Figure 11:
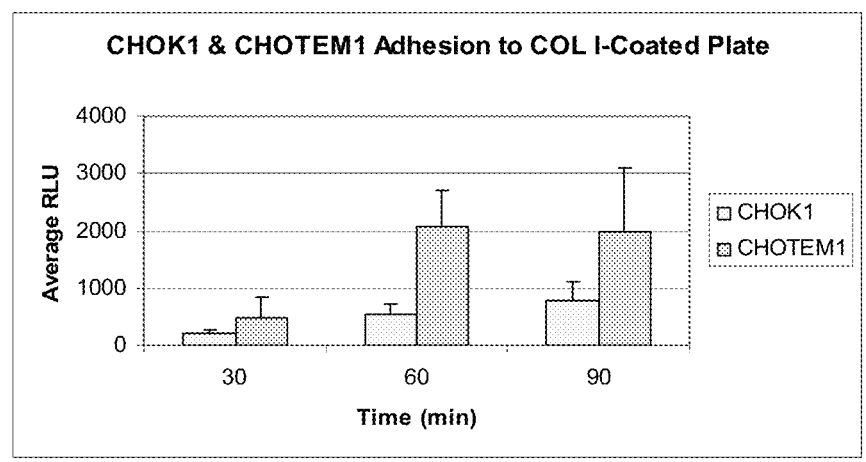
FIG. 11 shows endosialin-mediated cellular binding to EMP collagen. CHO cells were transfected with a vector expressing endosialin or mock cDNA. Cells were confirmed to express cell surface endosialin (CHOTEM1) while those transfected with mock (CHOK1) did not. Cells were then tested for the ability to bind EMP collagen type I. As shown, over-expression of endosialin results in increased cell binding to COL I.

CHO-K1 or CHO-TEM1 cells ($1.5 \times 10^5$ cells/well) were washed and suspended in PBS containing $Mg^{2+}/Ca^{2+}$, and added in quadruplicate to a 96-well plate coated with Collagen I and allowed to adhere for the indicated time points. After the cells were allowed to adhere the plate was washed 5 times with PBS and viability was measured using CellTiter-Glo®. As shown in FIG. 11, over-expression of endosialin results in increased cell binding to COL I.

Example 13

Cell Migration Assay

The BD BioCoat Tumor Invasion System™ (BD Bioscience) and Human Fibronectin Cell Culture inserts (BD Bioscience) were used to assess TEM1-mediated migration of cells. Cells were harvested with nonenzymatic cell dissociation buffer and diluted to a concentration of 4E5 cells/ml in growth media supplemented with 2% fetal bovine serum (FBS), and 500 ul of cell suspension was added to the top chamber of the membrane insert. To create a gradient, growth media containing 20% FBS was added to the bottom chamber. Cells were incubated for 48 hours, after which the insert was removed and cells that had migrated through the coated membrane were counted using CELLTITER-GLO (Promega). Cells were pretreated with antibody as indicated in the description of FIG. 12 and migration was assessed in the continual presence of antibody. To examine the formation of tubules on MATRIGEL, cells (8E4 cells/well) were added to a 96-well plate coated with MATRIGEL (BD Bioscience), incubated overnight and photographed at 200-400× magnification.

Figure 12A:
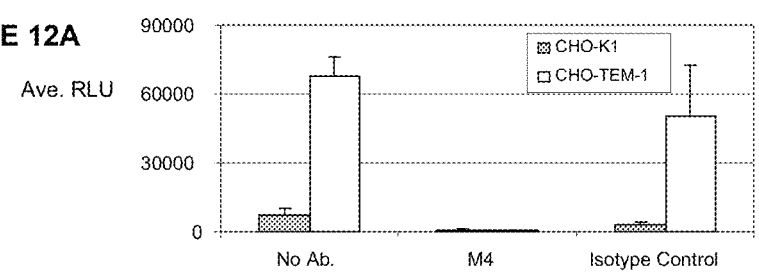
As shown in FIG. 12A, CHO-K1 cells exhibited modest cell migration, whereas CHO-TEM1 cells showed >10-fold enhanced migration. M4 antibody treatment, but not control IgG, abolished CHO-TEM1 cell migration. Similar results were observed in migration experiments using transwell chambers coated with FN (FIG. 12B).
Figure 12B:
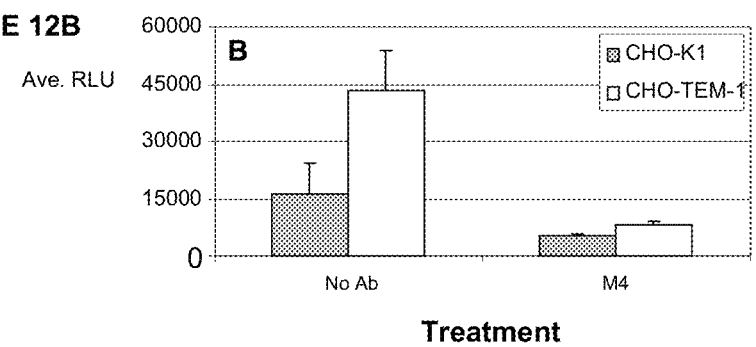
FIG. 12 shows mediation of cell migration by endosialin and inhibition thereof by anti-endosialin antibody M4. The ability of M4 to inhibit the migration of CHO-TEM1 and CHO-K1 cells through MATRIGEL- (FIG. 12A) or FN- (FIG. 12B) coated membranes was determined. Cells were added to the top chamber and allowed to migrate for 48 hours at 37° C. The membrane was removed and the number of migrated cells was determined using the CELLTITER-GLO Luminescence Cell Viability Assay. Where indicated, cells were treated with M4 or IgG isotype control for the duration of experiment.

As shown in FIG. 12A, CHO-K1 cells exhibited modest cell migration, whereas CHO-TEM1 cells showed >10-fold enhanced migration. M4 antibody treatment, but not control IgG, abolished CHO-TEM1 cell migration. Similar results were observed in migration experiments using transwell chambers coated with FN (FIG. 12B).

Example 14

Endosialin Increases MMP-9 Activity

Figure 13:
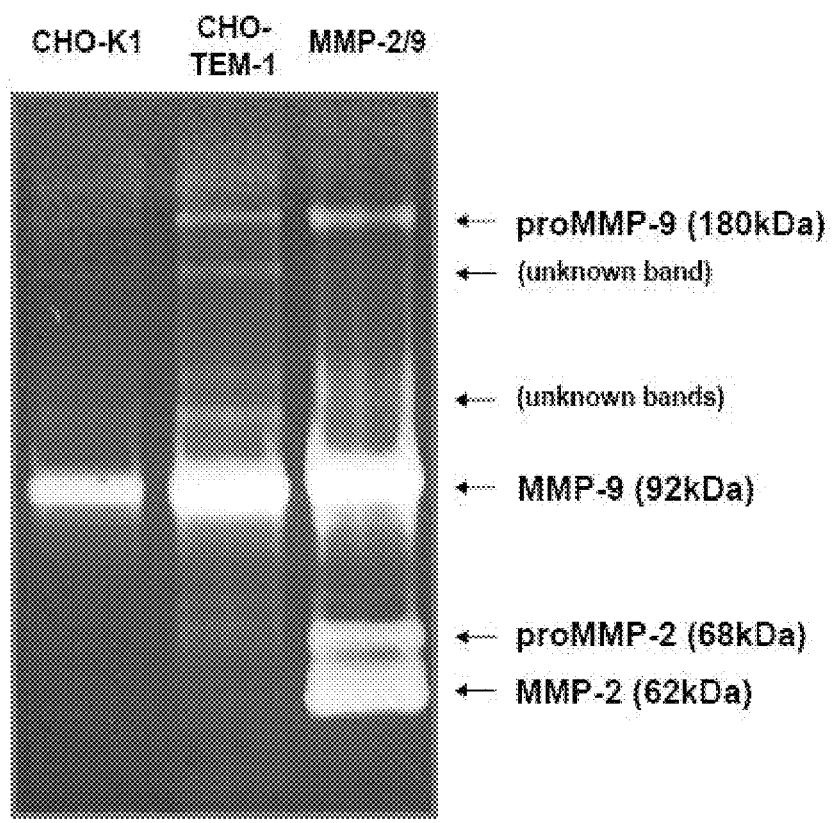
FIG. 13 shows endosialin enhancement of cellular pathways. CHO cells were transfected with a vector expressing endosialin or mock cDNA. Cells were confirmed to express cell surface endosialin (CHOTEM1) while those transfected with mock (CHOK1) did not. Cells were then tested for the ability to upregulate cellular pathways. One such pathway is the MMP9 pathway, which plays a role in cellular migration. As shown, over-expression of endosialin results in increased MMP-9 activity in contrast to control cells.

Endosialin, MMP-2, and COL IV have been shown to colocalize in tissue areas characterized by finger-like protrusions of early angiogenic processes (Virgintino et al. (2007) *Angiogenesis*, 10:35-45). To assess MMP activity, cells were seeded in a 6-well plate and serum starved for 48 h. The culture supernatant was collected and clarified by centrifugation (13,000 rpm, 15 min.) at 4° C. to remove any debris. Equal amounts of protein were subjected to gelatin and casein zymography under nonreducing conditions (Invitrogen) according to the manufacturer's protocol. Positive controls human MMP-2 and 9 (Chemicon, International) were used to indicate the migration of MMP-2 and MMP-9 and used as a reference for our CHOK1 and CHO-TEM-1 supernatants. As shown in FIG. 13, MMP-9 activity was significantly enhanced in CHO-TEM1 cells compared to parental CHO-K1 cells. The enhanced MMP-9 activity correlated with increased secretion of MMP-9 protein in the supernatant of CHO-TEM1 cells as measured by a MMP-specific ELISA (data not shown). These data indicate that induced MMP-9 secretion contributes to the enhanced migration capability of CHO-TEM1 cells through MATRIGEL and FN-coated transwells demonstrated herein.

Example 15

Endosialin Increases β-Integrin Activity

Integrins (e.g., α4β1, α5β1) are well-characterized receptors that mediate FN-dependent cell adhesion (Wierzbicka-Patynowski & Schwarzbauer 2003; Magnusson & Mosher 1998). In addition, an unidentified cellular receptor has been functionally described that binds the N-terminal 70 kDa region of FN (McKeown-Longo & Mosher (1983) *J. Cell Biol.*, 97:466-472) and is required to expose the cryptic integrin-binding site (RGD motif) of soluble FN involved with FN-integrin and FN-FN interactions (Tomasini-Johansson et al. (2006) *Matrix Biol.*, 25:282-293; McKeown-Longo & Mosher (1985) *J. Cell Biol.*, 100:364-374). Endosialin is identified herein as a novel receptor that interacts with the N-terminal 70 kDa FN region and enhances FN-dependent cell adhesion. The enhanced FN binding measured in these cellular systems in vitro could be the result of sequential interaction with endosialin and integrins.

Figure 14A:
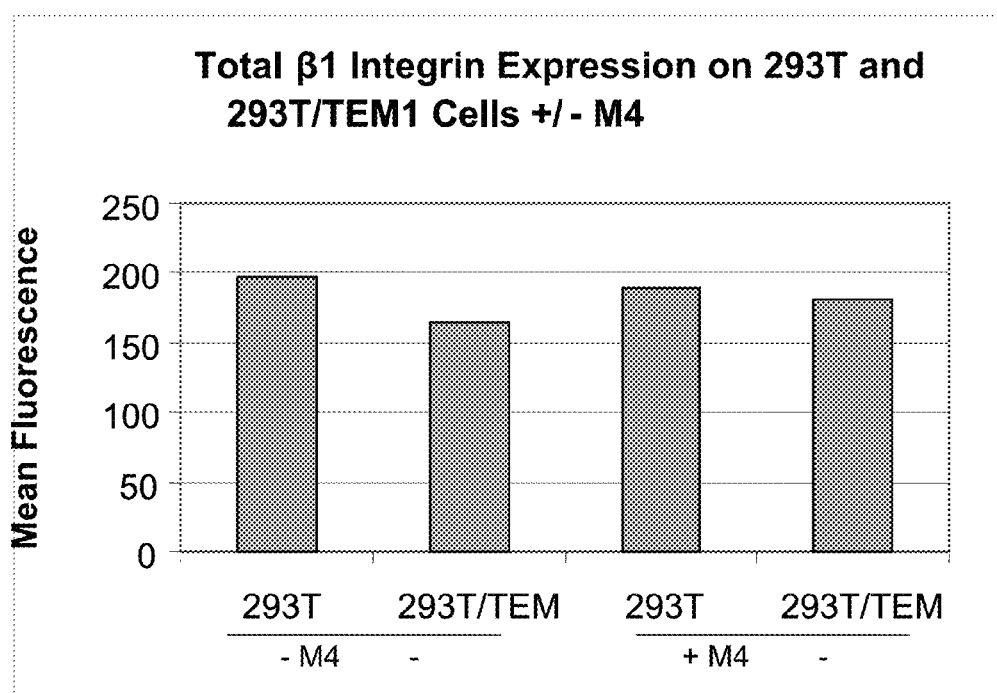
FIG. 14 shows the effect of blocking endosialin on β integrin activation. Human embryonic kidney 293 (HEK293) cells were transfected with a vector expressing endosialin or mock cDNA. Cells were confirmed to express cell surface endosialin (293TEM1) while those transfected with mock (293T) did not. Cells were then tested for the ability to upregulate cellular pathways. One such pathway is the integrin pathway which plays a role in cellular migration. As shown, over-expression of endosialin results in increased integrin β1 activity (FIG. 14B) in contrast to control cells while direct effect on cell surface β1 expression is not changed (FIG. 14A). Treatment of cells with the endosialin inhibitor M4 resulted in suppressed integrin activity while no effect on cell surface levels were observed (FIG. 14B). These data show the ability to use endosialin inhibitors to suppress integrin function in endosialin-expressing cells.
Figure 14B:
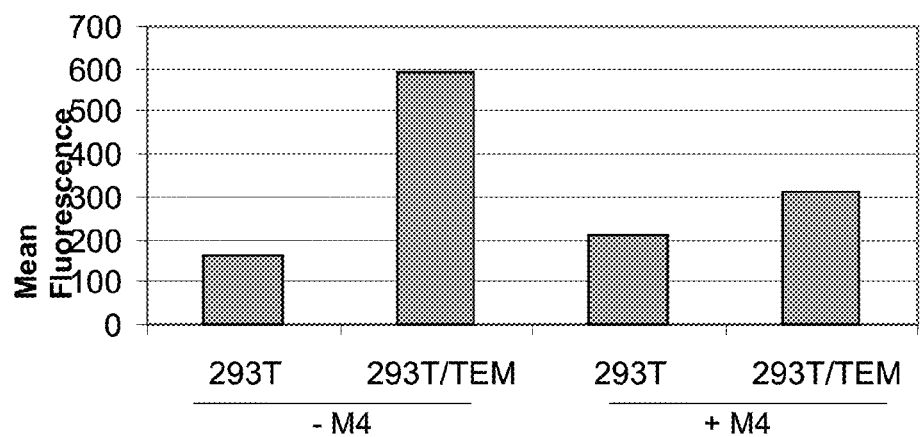

Human embryonic kidney 293 (HEK293) cells were transfected with a vector expressing endosialin or mock cDNA. Cells were confirmed to express cell surface endosialin (293TEM1) while those transfected with mock (293T) did not. Cells were the tested for the ability to upregulate integrin expression and activity in the presence of antibody M4. FIG. 14B shows that over-expression of endosialin results in increased integrin β1 activity relative to control cells. FIG. 14A shows that cell surface integrin β1 expression is not changed. Treatment of cells with the endosialin inhibitor M4 resulted in suppressed integrin activity while no effect on cell surface levels were observed (FIG. 14B). While not wishing to be bound to any one theory, the interaction between endosialin and the N-terminal 70 kDa fragment of soluble FN may be responsible for initiating the assembly of FN into a multimeric high affinity form able to bind integrins.

Example 16

M4.1 Recognizes Unreduced Human TEM-1 but not Murine TEM-1

CHO-TEM-1 cells, mouse 2H11 cells, parental CHO-K1 cells, mouse NS0 cells, and mouse MS1 cells were cultured in complete RPMI1640 (RPMI1640; sodium pyruvate; nonessential amino acids; L-glutamine, and FBS; Invitrogen Corp.). Human primary pericytes were cultured in Perciyte Medium (500 ml of basal medium (Cat #1201), 10 ml (2%) of fetal bovine serum (FBS, Cat. No. 0025), 5 ml of pericyte growth supplement (PGS, Cat. No. 1252) and 5 ml of penicillin/streptomycin solution (P/S, Cat. No. 0503); Invitrogen Corp.). Cells were grown at 37° C. and 5% $CO_2$ in a humidified incubator. Cells were deadhered with TrypLE™ Select (Invitrogen Corp., catalog no. 12563-011), washed, and counted. Cells were lysed at $2\times10^7$ cells in RIPA Lysis buffer containing protease inhibitors and incubated on ice for 10 minutes. Insoluble material was pelleted at 10,000×G for 10 minutes at 4° C., and supernatants were transferred to fresh tubes. Aliquots were mixed with an equal volume of 2× protein loading buffer with or without 10% 2-mercaptoethanol (reducing agent). 15 μL ($1.5\times10^5$ cells) of lysate were loaded onto a 15 well 4-12% Bis/Tris SDS-PAGE gel and electrophoresed for 30 minutes at 200V in MES running buffer. The gel was electroblotted onto PVDF, then blocked for 1 hour at room temperature with rocking in 5% milk-TBST (5% M-TBST). M4.1 blots were probed with M4.1 in 5% M-TBST at 3.3 ug/mL overnight at 4° C.

Rabbit anti-tem-1 polyclonal antibody blots were probed with a 1:300 dilution (4.5 mg/ml stock Lot #: NB487-76) of antibody in 5% M-TBST overnight at 4° C. Antibody M4.1, like antibody M4, is a humanized antibody to human endosialin. Membranes were washed 5 times for 5 minutes each with 30 mL TBST at room temperature. HRP-conjugated goat anti-human IgG (H+L) (Jackson Immuno, 1 mg/mL stock) was diluted 1:20,000 in 5% M-TBST as a secondary antibody for probing the M4.1 blots for 30 minutes at room temperature. HRP-conjugated goat anti-rabbit (H+L) secondary antibody was used to blot the polyclonal anti-TEM-1 blots for 30 minutes at room temperature. Membranes were washed 5 times for 5 minutes each with 30 mL TBST at room temperature. Signal was detected by chemiluminescence using the Femto Western Blot Detection System (Pierce) as per manual.

Figure 15:
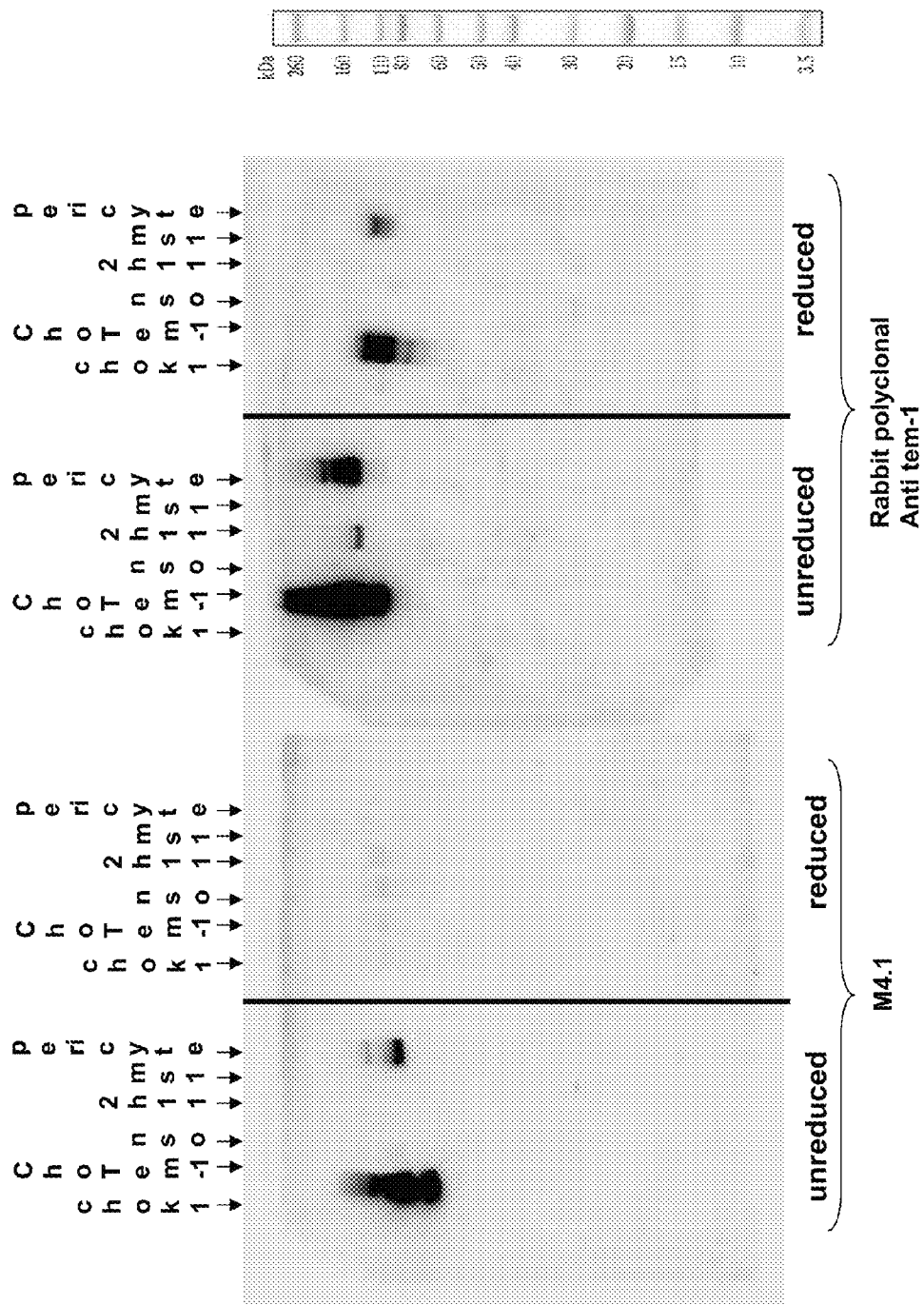
FIG. 15 illustrates that antibody M4.1 recognizes unreduced human TEM-1 in CHO-TEM-1 cells and human primary pericytes but not murine TEM-1 in mouse 2H11 cells. Rabbit polyclonal against human TEM-1 (rabPAb TEM-1) recognizes human TEM-1 in CHO-TEM-1 cells and human pericytes, but also murine TEM-1 in mouse 2H11 cells. Neither M4.1 nor rabPAb TEM-1 reacted against lysates from parental CHO-K1 cells or mouse NS0 and MS1 cells due to lack of TEM-1 expression in these cells. Only rabPAb TEM-1 reacted with reduced human TEM-1, albeit to a lesser extent when compared to unreduced TEM-1.

As illustrated in FIG. 15, M4.1 recognizes unreduced human TEM-1 in CHO-TEM-1 cells and human primary pericytes but not murine TEM-1 (SEQ ID NO:2) in mouse 2H11 cells (FIG. 15). Rabbit polyclonal against human TEM-1 (rabPAb TEM-1) recognizes human TEM-1 in CHO-TEM-1 cells and human pericytes, but also murine TEM-1 in mouse 2H11 cells. Neither M4.1 nor rabPAb TEM-1 reacted against lysates from parental CHO-K1 cells or mouse NS0 and MS1 cells due to lack of TEM-1 expression in these cells. Only rabPAb TEM-1 reacted with reduced human TEM-1, albeit to a lesser extent when compared to unreduced TEM-1.

The present invention is not limited to the embodiments described and exemplified above, but is capable of variation and modification within the scope of the appended claims.

What is claimed:

1. A method for inhibiting the interaction of an endosialin-expressing cell with collagen or fibronectin, comprising contacting said endosialin-expressing cell with an antibody produced by cells having ATCC Access. No. PTA-9017, wherein binding of said antibody to endosialin expressed on the surface of the endosialin-expressing cell inhibits the interaction of said endosialin-expressing cell with said collagen or fibronectin.

2. The method of claim 1, wherein inhibiting the interaction of said endosialin-expressing cell with said collagen or fibronectin inhibits migration of the endosialin-expressing cell.

3. The method of claim 1, wherein inhibiting the interaction of said endosialin-expressing cell with said collagen or fibronectin inhibits the activation of a matrix metalloprotease.

4. The method of claim 3 wherein the matrix metalloprotease is MMP-9.

5. The method of claim 1, wherein inhibiting the interaction of said endosialin-expressing cell with said collagen or fibronectin inhibits the expression of a matrix metalloprotease.

6. The method of claim 5 wherein the matrix metalloprotease is MMP-9.

7. The method of claim 1 wherein inhibiting the interaction of said endosialin-expressing cell with said collagen or fibronectin inhibits the activation of integrin $\beta1$, $\beta2$, or $\beta3$.

8. The method of claim 1 wherein said endosialin-expressing cell is a mammalian cell.

9. The method of claim 1, wherein said endosialin-expressing cell is a neoplastic cell.

10. A method for inhibiting neovascularization in a subject comprising administering to the subject a therapeutically effective amount of an antibody produced by cells having ATCC Access. No. PTA-9017, wherein said antibody inhibits the interaction of endosialin expressed on the surface of a cell with collagen or fibronectin, and wherein inhibiting said interaction of endosialin expressed on the surface of said cell with said collagen or fibronectin inhibits neovascularization of a tissue, organ, or neoplasm in the subject.

11. The method of claim 10, wherein inhibiting said interaction of endosialin expressed on the surface of said cell with said collagen or fibronectin inhibits migration of the cell.

12. The method of claim 10, wherein inhibiting said interaction of endosialin expressed on the surface of said cell with said collagen or fibronectin inhibits the activation of a matrix metalloprotease.

13. The method of claim 12, wherein the matrix metalloprotease is MMP-9.

14. The method of claim 10, wherein inhibiting said interaction of endosialin expressed on the surface of said cell with said collagen or fibronectin inhibits the expression of a matrix metalloprotease.

15. The method of claim 14, wherein the matrix metalloprotease is MMP-9.

16. The method of claim 10, wherein inhibiting said interaction of endosialin expressed on the surface of said cell with said collagen or fibronectin inhibits the activation of integrin $\beta1$, $\beta2$, or $\beta3$.

17. The method of claim 10, wherein said cell is a mammalian cell.

18. The method of claim 10, wherein said cell is a neoplastic cell.

19. A method for inhibiting angiogenesis in a subject comprising administering to the subject a therapeutically effective amount of an antibody produced by cells having ATCC Access. No. PTA-9017, wherein said antibody inhibits the interaction of endosialin expressed on the surface of a cell with collagen or fibronectin, and wherein inhibiting said interaction of endosialin expressed on the surface of said cell with said collagen or fibronectin inhibits angiogenesis of a tissue, organ, or neoplasm in the subject.

20. The method of claim 19, wherein inhibiting said interaction of endosialin expressed on the surface of said cell with said collagen or fibronectin inhibits migration of the cell.

21. The method of claim 19, wherein inhibiting said interaction of endosialin expressed on the surface of said cell with said collagen or fibronectin inhibits the activation of a matrix metalloprotease.

22. The method of claim 21, wherein the matrix metalloprotease is MMP-9.

23. The method of claim 19, wherein inhibiting said interaction of endosialin expressed on the surface of said cell with said collagen or fibronectin inhibits the expression of a matrix metalloprotease.

24. The method of claim 23, wherein the matrix metalloprotease is MMP-9.

25. The method of claim 19, wherein inhibiting said interaction of endosialin expressed on the surface of said cell with said collagen or fibronectin inhibits the activation of integrin $\beta1$, $\beta2$, or $\beta3$.

26. The method of claim 19, wherein said cell is a mammalian cell.

27. The method of claim 19, wherein said cell is a neoplastic cell.

28. A method for inhibiting the interaction of an endosialin-expressing cell with collagen or fibronectin, comprising obstructing endosialin expressed on the surface of said cell, wherein said obstructing inhibits the interaction of said cell with said collagen or fibronectin, wherein said obstructing comprises contacting said cell with an antibody produced by cells having ATCC Access. No. PTA-9017.

* * * * *